(12) United States Patent
Hirano et al.

(10) Patent No.: US 7,955,845 B2
(45) Date of Patent: Jun. 7, 2011

(54) MODIFIED ANTIGEN-PRESENTING CELLS

(75) Inventors: Naoto Hirano, Brookline, MA (US); Marcus Butler, Jamaica Plain, MA (US); Lee M. Nadler, Newton, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 10/850,294

(22) Filed: May 20, 2004

(65) Prior Publication Data

US 2005/0003484 A1    Jan. 6, 2005

Related U.S. Application Data

(63) Continuation-in-part of application No. PCT/US02/37123, filed on Nov. 20, 2002.

(51) Int. Cl.
*C12N 5/071* (2010.01)
*C12N 5/00* (2010.01)
*C12N 5/02* (2010.01)
*C12N 15/00* (2010.01)

(52) U.S. Cl. .......... 435/325; 435/455; 435/366

(58) Field of Classification Search .......... None
See application file for complete search history.

(56) References Cited

U.S. PATENT DOCUMENTS

| 5,858,776 A * | 1/1999 | Ostrand-Rosenberg et al. ............ 435/325 |
| 5,962,320 A * | 10/1999 | Robinson ............ 435/366 |
| 6,187,307 B1 | 2/2001 | Cohen ............ 424/93.21 |
| 6,194,205 B1 | 2/2001 | Staege et al. ............ 435/373 |
| 6,251,627 B1 | 6/2001 | Cai et al. ............ 435/69.1 |
| 6,319,709 B1 * | 11/2001 | Ostrand-Rosenberg et al. ............ 435/325 |
| 6,620,912 B2 * | 9/2003 | Young et al. ............ 530/350 |
| 7,001,733 B1 * | 2/2006 | Ferrick et al. ............ 435/7.2 |

FOREIGN PATENT DOCUMENTS

| WO | WO 9529236 A2 * | 11/1995 |
| WO | WO 96/27392 | 9/1996 |
| WO | WO 97/29183 | 8/1997 |

OTHER PUBLICATIONS

Ginsberg, 1996, The ups and downs of adenovirus vectors. Bull NY Acad. Med. vol. 73:53-8.*
Latouche et al., 2000, Induction of human cytotoxic T lymphocytes by artificial antigen-presenting cells. Nature Biotech. vol. 18:405-409.*
Zoeten et al., 1998, Resistance to Melanoma in Mice immunized with semiallogeneic fibroblasts transfected with DNA from mouse melanoma cells. J. Immunol. vol. 160: 2915-22.*
Hood et al., 1983, Genes of the major histocompatibility complex of the mouse. Ann. Rev. Immunol. vol. 1:529-68.*
Auffray et al., 1986, Molecular genetics of the human major histocompatibility complex, Adv. Hum. Genet. vol. 15:197-247.*
Scholler et al., 2001, J. Immunol. vol. 166: 3865-72.*
Janeway and Travers, 1997, Immunobiology, p. 4:7.*
Lohmann et al., 2000, Cancer Gene Therapy, vol. 7: 605-614.*
Stauss, et al.; "Induction of cytotoxic T lymphocytes with peptides in vitro: Identification of candidate T-cell epitopes in human papilloma virus"; *Proc. Natl. Acad. Sci. USA*; (1992); 89: 7871-7875.
Carbone, et al.; "Induction of Cytotoxic T Lymphocytes by Primary in vitro Stimulation with Peptides"; *J. Exp. Med.*; (1988); 167: 1767-1779.
Trowsdale & Campbell; "Complexity in the Major Histocompatibility Complex"; *Euro. J. Immunogenetics*; (1993); 19: 45-55.
Speiser, et al.; "Discrepancy between in vitro Measurable and in vivo Virus Neutralizing Cytotoxic T Cell Reactivities"; *J. Immunol.*; (1992); 149: 972-80.
Braciale; "Antigen processing for presentation by MHC class I molecules"; *Curr. Opin. Immunol.*; (1992); 4: 59-62.
Lehner and Trowsdale; "Antigen presentation: Coming out Gracefully"; *Curr. Biol.* (1998); 8: R605-R608.
Wick & Ljunggren; "Processing of bacterial antigens for peptide presentation on MHC class I molecules"; *Immunol. Rev.*; (1999); 172: 153-62.

* cited by examiner

*Primary Examiner* — Amy E Juedes
(74) *Attorney, Agent, or Firm* — Edwards Angell Palmer & Dodge LLP; Elizabeth Spar; Kathleen Williams

(57) ABSTRACT

The invention relates to antigen-presenting cells having specificity against a selected antigen and methods for making the cells. The invention also relates to a method of selecting efficient antigen-presenting cells using reporter fusion constructs. The highly efficient antigen-presenting cells of the invention will provide a therapeutic strategy of modulating immune responses for a variety of diseases.

33 Claims, 20 Drawing Sheets

Structure of EGFP-antigenic Peptide Fusion Proteins

Figure 12. Expression of trausduced genes in MEA1
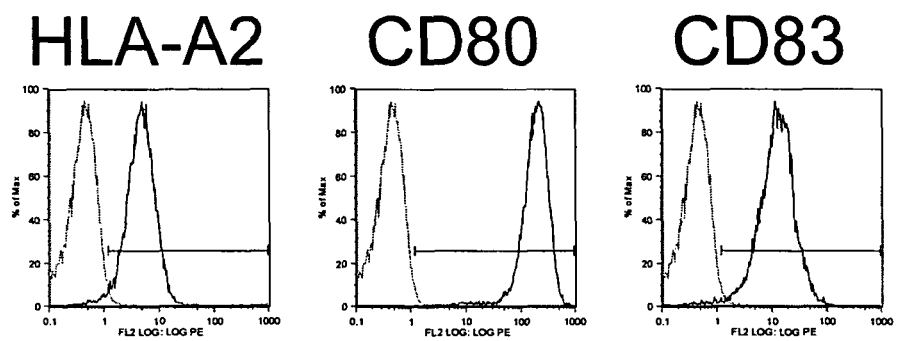

Figure 13. Scheme for CTL Generation by MEA1
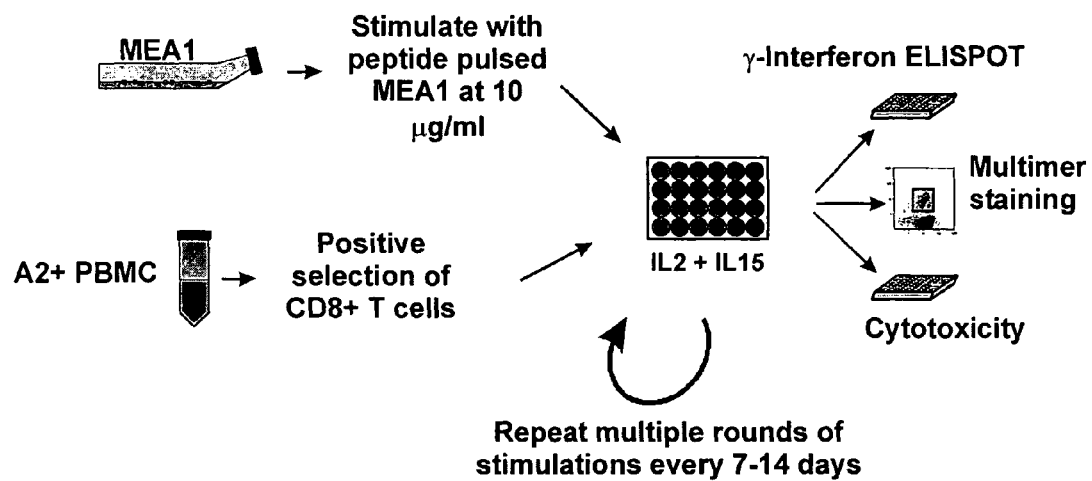

Figure 14. Stimulation of Flu, MP58, Specific T Cells
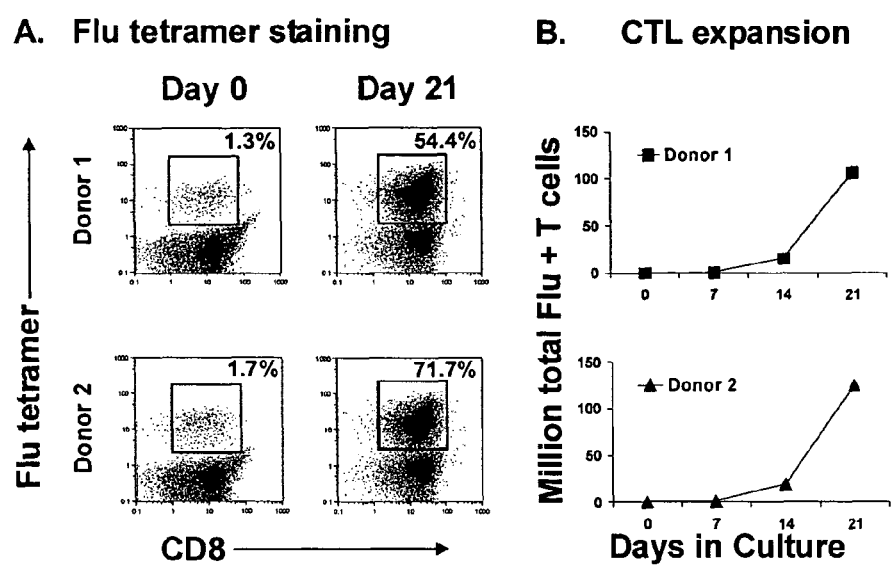

Figure 15. Stimulation of MART-1, M27, Specific T Cells
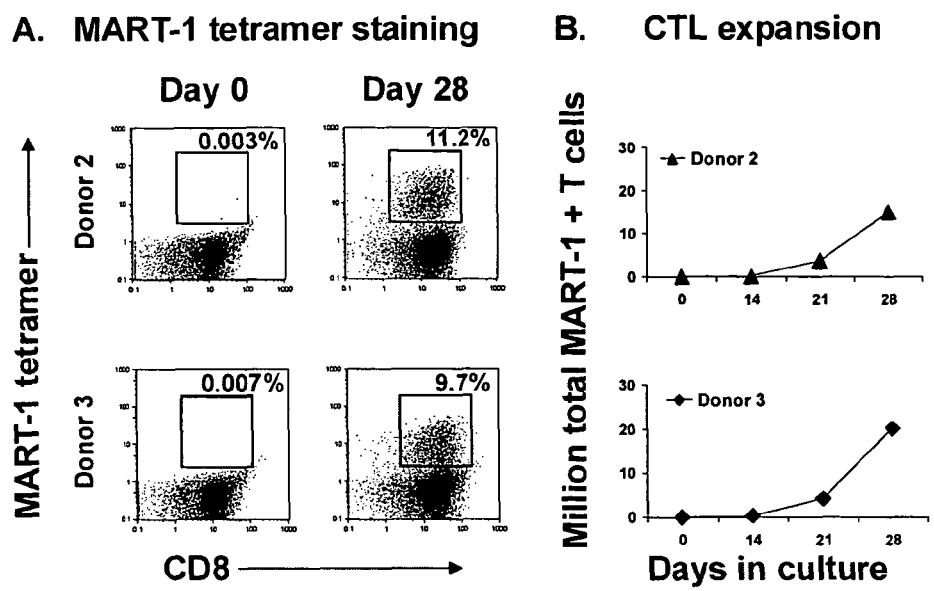

Figure 16. Cytotoxicity of Peptide Pulsed T2 Targets
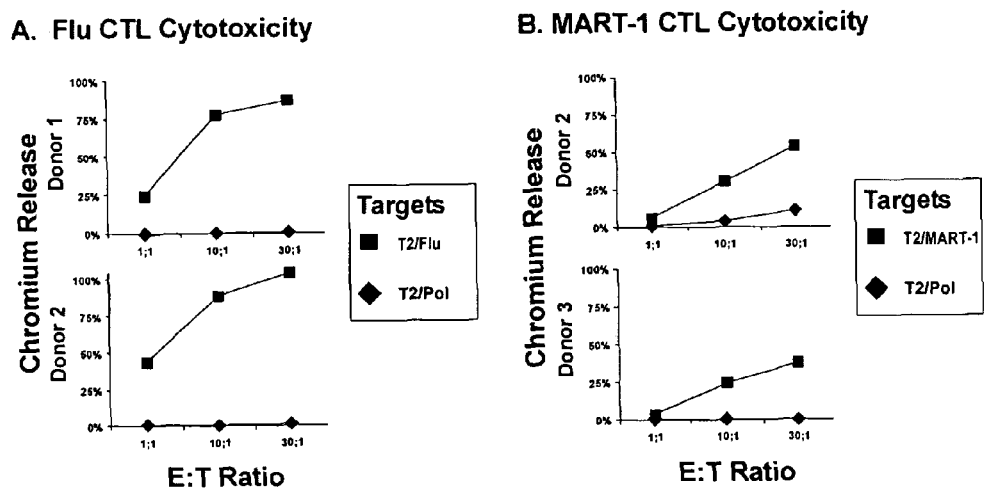

Figure 17. γ-Interferon Secretion as Measured by ELISPOT
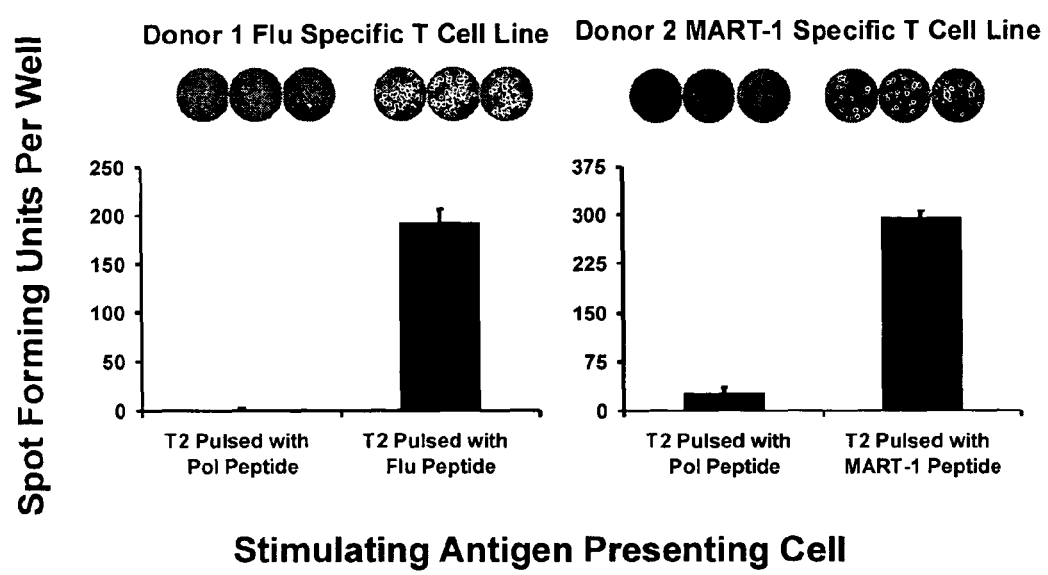

Figure 18. Phenotype of Multimer Stained "Young" CTL
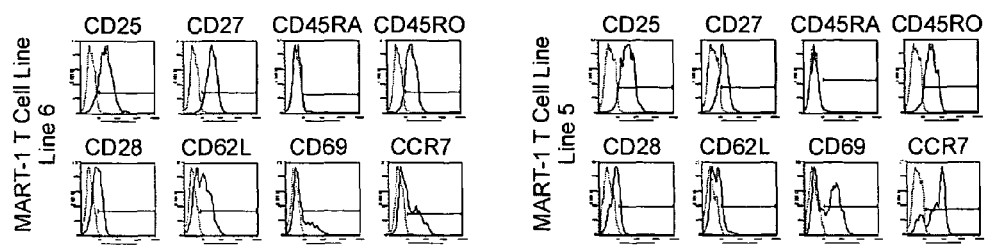

Figure 19. NY-ESO-1 Line Cultured for >1 Year and HER-2/neu Line Cultured for >6 Months
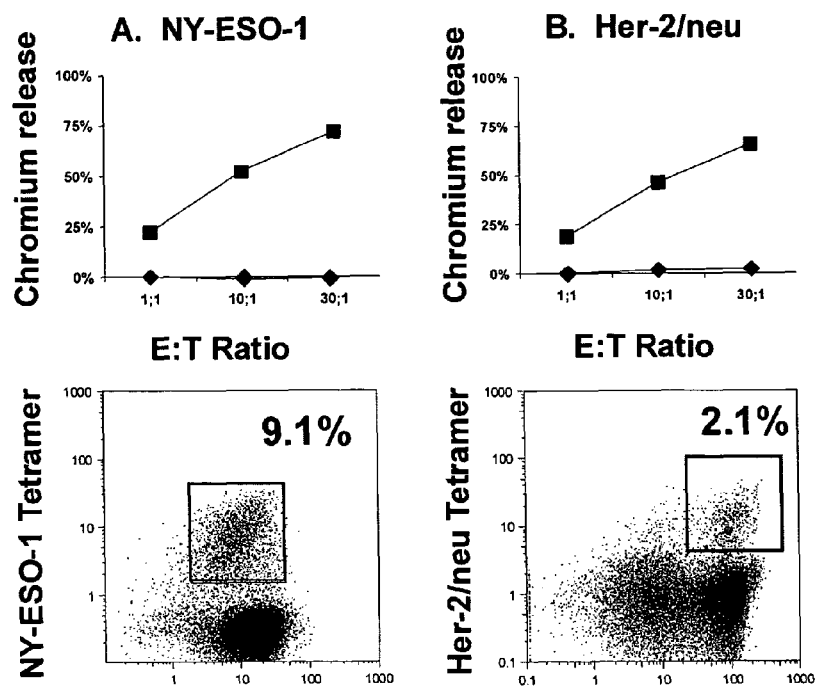

Figure 20. Vβ Subtyping: All Long Lived NY-ESO-1 Multimer+ Cells are Vβ 17+
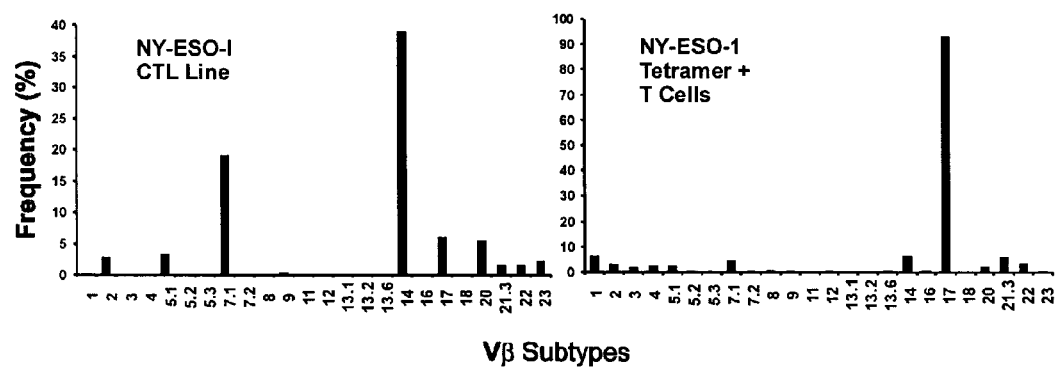

Figure 21. Phenotype of Long Lived (>1 Year) NY-ESO-1 Multimer + T Cells
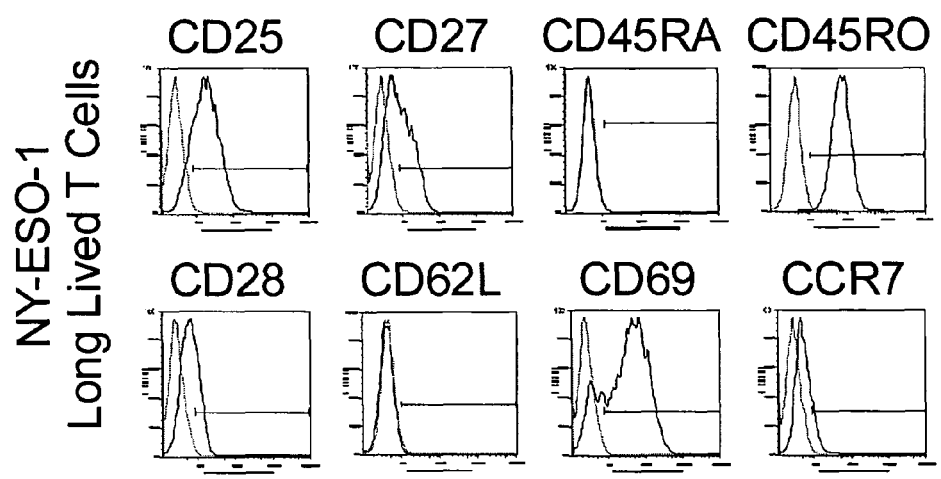

SEQUENCE LISTING

```
<160> NUMBER OF SEQ ID NOS: 34

<210> SEQ ID NO 1
<211> LENGTH: 10
<212> TYPE: PRT
<213> ORGANISM: Artificial
<220> FEATURE:
<223> OTHER INFORMATION: MART-1, M27 peptide fragment

<400> SEQUENCE: 1

Glu Ala Ala Gly Ile Gly Ile Leu Thr Val
1               5                   10

<210> SEQ ID NO 2
<211> LENGTH: 9
<212> TYPE: PRT
<213> ORGANISM: Artificial
<220> FEATURE:
<223> OTHER INFORMATION: S9C, NY-ESP-1 peptide fragment

<400> SEQUENCE: 2

Ser Leu Leu Met Trp Ile Thr Gln Cys
1               5

<210> SEQ ID NO 3
<211> LENGTH: 9
<212> TYPE: PRT
<213> ORGANISM: Artificial
<220> FEATURE:
<223> OTHER INFORMATION: Htert, 1540 peptide fragment

<400> SEQUENCE: 3

Ile Leu Ala Lys Phe Leu His Trp Leu
1               5

<210> SEQ ID NO 4
<211> LENGTH: 9
<212> TYPE: PRT
<213> ORGANISM: Artificial
<220> FEATURE:
<223> OTHER INFORMATION: Her2/neu, E75 peptide fragment

<400> SEQUENCE: 4

Lys Ile Phe Gly Ser Leu Ala Phe Leu
1               5

<210> SEQ ID NO 5
<211> LENGTH: 9
<212> TYPE: PRT
<213> ORGANISM: Artificial
<220> FEATURE:
```

<223> OTHER INFORMATION: HIV, pol peptide fragment

<400> SEQUENCE: 5

Ile Leu Lys Glu Pro Val His Gly Val
1               5

<210> SEQ ID NO 6
<211> LENGTH: 9
<212> TYPE: PRT
<213> ORGANISM: Artificial
<220> FEATURE:
<223> OTHER INFORMATION: influenze, MP58 peptide fragment

<400> SEQUENCE: 6

Gly Ile Leu Gly Phe Val Phe Thr Leu
1               5

<210> SEQ ID NO 7
<211> LENGTH: 10
<212> TYPE: PRT
<213> ORGANISM: Artificial
<220> FEATURE:
<223> OTHER INFORMATION: MART-1 heteroclytic peptide, A27L

<400> SEQUENCE: 7

Glu Leu Ala Gly Ile Gly Ile Leu Thr Val
1               5                   10

<210> SEQ ID NO 8
<211> LENGTH: 4
<212> TYPE: PRT
<213> ORGANISM: homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 8

Arg Xaa Lys Arg
1

<210> SEQ ID NO 9
<211> LENGTH: 12
<212> TYPE: DNA
<213> ORGANISM: Homo sapiens
<220> FEATURE:
<221> NAME/KEY: misc_feature
<222> LOCATION: (4)..(6)
<223> OTHER INFORMATION: n = any nucleotide

<400> SEQUENCE: 9
cgcnnnaagc gc                                                           12

<210> SEQ ID NO 10
<211> LENGTH: 6
<212> TYPE: PRT
<213> ORGANISM: Homo sapiens

<400> SEQUENCE: 10

Pro Leu Gly Leu Trp Ala
1               5

<210> SEQ ID NO 11
<211> LENGTH: 18
<212> TYPE: DNA
<213> ORGANISM: Homo sapiens

<400> SEQUENCE: 11

```
cccctgggcc tgtgggcc                                                    18
```

<210> SEQ ID NO 12
<211> LENGTH: 6
<212> TYPE: PRT
<213> ORGANISM: Homo sapiens

<400> SEQUENCE: 12

Tyr Glu Val Asp Gly Glu
1               5

<210> SEQ ID NO 13
<211> LENGTH: 18
<212> TYPE: DNA
<213> ORGANISM: Homo sapiens

<400> SEQUENCE: 13

```
tacgaggtgg acggctgg                                                    18
```

<210> SEQ ID NO 14
<211> LENGTH: 7
<212> TYPE: PRT
<213> ORGANISM: Homo sapiens

<400> SEQUENCE: 14

Val Asp Val Ala Asp Gly Trp
1               5

<210> SEQ ID NO 15
<211> LENGTH: 21
<212> TYPE: DNA
<213> ORGANISM: Homo sapiens

<400> SEQUENCE: 15

```
gtggacgtgg ccgacggctg g                                                21
```

<210> SEQ ID NO 16
<211> LENGTH: 7
<212> TYPE: PRT
<213> ORGANISM: Homo sapiens

<400> SEQUENCE: 16

Val Asp Gln Met Asp Gly Trp
1               5

<210> SEQ ID NO 17
<211> LENGTH: 21
<212> TYPE: DNA
<213> ORGANISM: Homo sapiens

<400> SEQUENCE: 17

```
gtggaccaga tggacggctg g                                                21
```

<210> SEQ ID NO 18
<211> LENGTH: 6
<212> TYPE: PRT
<213> ORGANISM: Homo sapiens

<400> SEQUENCE: 18

Leu Glu Val Asp Gly Trp
1               5

<210> SEQ ID NO 19
<211> LENGTH: 18

```
<212> TYPE: DNA
<213> ORGANISM: Homo sapiens

<400> SEQUENCE: 19
ctggaggtgg acggctgg                                                 18

<210> SEQ ID NO 20
<211> LENGTH: 6
<212> TYPE: PRT
<213> ORGANISM: Homo sapiens

<400> SEQUENCE: 20

Val Gln Val Asp Gly Trp
1               5

<210> SEQ ID NO 21
<211> LENGTH: 18
<212> TYPE: DNA
<213> ORGANISM: Homo sapiens

<400> SEQUENCE: 21
gtgcaggtgg acggctgg                                                 18

<210> SEQ ID NO 22
<211> LENGTH: 7
<212> TYPE: PRT
<213> ORGANISM: Homo sapiens

<400> SEQUENCE: 22

Val Asp Gln Val Asp Gly Trp
1               5

<210> SEQ ID NO 23
<211> LENGTH: 21
<212> TYPE: DNA
<213> ORGANISM: Homo sapiens

<400> SEQUENCE: 23
gtggaccagg tggacggctg g                                             21

<210> SEQ ID NO 24
<211> LENGTH: 4
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: X = any amino acid

<400> SEQUENCE: 24

Asp Xaa Xaa Asp
1

<210> SEQ ID NO 25
<211> LENGTH: 12
<212> TYPE: DNA
<213> ORGANISM: Homo sapiens
<220> FEATURE:
<221> NAME/KEY: misc_feature
<222> LOCATION: (4)..(9)
<223> OTHER INFORMATION: n = any nucleotide

<400> SEQUENCE: 25
gacnnnnnng ac                                                       12

<210> SEQ ID NO 26
```

-continued

```
<211> LENGTH: 4
<212> TYPE: PRT
<213> ORGANISM: Homo sapiens

<400> SEQUENCE: 26

Arg Gly Leu Thr
1

<210> SEQ ID NO 27
<211> LENGTH: 12
<212> TYPE: DNA
<213> ORGANISM: Homo sapiens

<400> SEQUENCE: 27
cgcggcctga cc                                                             12

<210> SEQ ID NO 28
<211> LENGTH: 17
<212> TYPE: PRT
<213> ORGANISM: Homo sapiens

<400> SEQUENCE: 28

Asn Phe Asp Leu Leu Lys Leu Ala Gly Asp Val Glu Ser Asn Pro Gly
1               5                   10                  15

Pro

<210> SEQ ID NO 29
<211> LENGTH: 51
<212> TYPE: DNA
<213> ORGANISM: Homo sapiens

<400> SEQUENCE: 29
acctccgacc tgctgaagct ggccggcgac gtggagagca accccggccc c                   51

<210> SEQ ID NO 30
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (4)..(2)
<223> OTHER INFORMATION: X = any amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 30

Ala Xaa Ala Xaa
1

<210> SEQ ID NO 31
<211> LENGTH: 12
<212> TYPE: DNA
<213> ORGANISM: Homo sapiens
<220> FEATURE:
<221> NAME/KEY: misc_feature
<222> LOCATION: (4)..(6)
<223> OTHER INFORMATION: n = any nucleotide
<220> FEATURE:
<221> NAME/KEY: misc_feature
<222> LOCATION: (10)..(12)
<223> OTHER INFORMATION: n = any nucleotide

<400> SEQUENCE: 31
```

```
gccnnngccn nn                                                            12

<210> SEQ ID NO 32
<211> LENGTH: 9
<212> TYPE: PRT
<213> ORGANISM: Homo sapiens

<400> SEQUENCE: 32

Gly Gly Phe Leu Arg Lys Val Gly Gln
1               5

<210> SEQ ID NO 33
<211> LENGTH: 27
<212> TYPE: DNA
<213> ORGANISM: Homo sapiens

<400> SEQUENCE: 33
ggcggcttcc tgcgcaaggt gggccag                                            27

<210> SEQ ID NO 34
<211> LENGTH: 17
<212> TYPE: PRT
<213> ORGANISM: Foot-and-mouth disease virus

<400> SEQUENCE: 34

Asn Phe Asp Leu Leu Lys Leu Ala Gly Asp Val Glu Ser Asn Pro Gly
1               5                   10                  15

Pro
```

MODIFIED ANTIGEN-PRESENTING CELLS

RELATED APPLICATION

This application is a Continuation-in-Part of International Application PCT/US02/37123, with an international filing date of Nov. 20, 2002. The entire teaching of the above application is incorporated herein by reference.

FIELD OF THE INVENTION

The invention relates to compositions and methods comprising modified antigen-presenting cells for modulating an antigen-specific immune response.

BACKGROUND

Antigen molecules are recognized by the immune system after internal processing by antigen-presenting cells (APCs) (Lanzavecchia, 1996, Curr. Opin. Immunol., 8:348-54). In order to present an antigen, the antigen is broken down into small peptidic fragments by enzymes contained in vesicles in the cytoplasm of the antigen-presenting cells (for reviews, see: Wick, et al., 1999, Immunol. Rev., 172:153-62; Lehner, et al., 1998, Curr. Biol., 8: R605-8; Braciale, 1992, Curr. Opin. Immunol., 4:59-62). The enzymes are part of a complex of proteolytic enzymes called a proteosome. Most cells have several different types of proteosomes with differing combinations of specificities, which they use to recycle their intracellular proteins. The peptides produced by the proteosomes are generated in the cytosol and must be transported into the Golgi compartment in order to associate with newly synthesized class I molecules. This is accomplished by a heterodimeric protein called TAP (for transporter associated with antigen processing) (Townsend, et al., 1993, Eur. J. Immunogenetics, 19:45-55), which is associated with the ER and actively transports peptides into the Golgi, where they are linked to cellular major histocompatibility complex (MHC) molecules (known as HLA in human).

There are two types of MHC molecules used for antigen presentation, class I and class II molecules. MHC class I molecules are expressed on the surface of all cells and MHC class II are expressed on the surface of a specialized class of cells called professional antigen-presenting cells. MHC class II molecules bind primarily to peptides derived from proteins made outside of an antigen-presenting cell, but can present self (endogenous) antigens. In contrast, MHC class I molecules bind to peptides derived from proteins made inside a cell, including proteins expressed by an infectious agent (e.g., such as a virus) in the cell and by a tumor cell. When the MHC class I proteins reach the surface of the cell these molecules will thus display any one of many peptides derived from the cytosolic proteins of that cell, along with normal "self" peptides being synthesized by the cell. Peptides presented in this way are recognized by T-cell receptors which engage T-lymphocytes in an immune response against the antigens (cellular immunity).

Antigen binding also requires the interaction of a number of co-receptor/ligand molecules that interact with ligand/receptors on the T cell. CD4 and CD8 act as co-receptors (one type only present per T cell) that interact with the TCR on the appropriate T cell to form a receptor/co-receptor complex. The receptor/co-receptor complex binds to the relevant MHC molecules on the APC. CD4 binds to class II molecules and CD8 binds to class I molecules. Various adhesion molecules (e.g., LFA-1, LFA2 (CD2), LFA3 (CD58), ICAM1, ICAM2, ICAM3), costimulatory molecules (e.g., CD80: B7-1 and B7-2) and accessory molecules (e.g., CD83) are also involved in facilitating T cell binding to APCs.

Conventional immunization techniques, such as those using killed or attenuated viruses, often fail to elicit an appropriate CTL response which is effective against an intracellular infection. Thus, there remains a need for the development of vaccines that stimulate appropriate responses (i.e., cell-mediated as well as antibody-mediated immune responses), in order to prevent disease.

Induction of primary MHC class I restricted CTL by pure soluble antigenic proteins in vitro has not been reported. The most common tool for ex vivo induction of primary CTL are small (8-11-mer) synthetic peptides (Stauss, et al., 1992, Proc. Natl. Acad. Sci. U.S.A., 89:7871-5); Carbone, et al., 1988, J. Exp. Med., 167:1767-79). These synthetic peptides associate with class I molecules on the cell surface without the requirement for endogenous processing. When presented on the surface of an appropriate APC (such as a dendritic cell) they can then induce a primary CTL response. However, frequently these CTL do not protect against challenge with pathogens that endogenously synthesize the protein from which the peptide was derived because of their low T-cell receptor avidity (Speiser, et al., 1992, J. Immunol., 149:972-80) and because they induce reactivity with a single epitope of the target antigen.

Another way of activating an efficient immune response against a specific antigen is to stimulate T cells with APCs engineered to express a specific antigen. U.S. Pat. Nos. 5,962,320, 6,187,307, 6,194,205 and patent publication WO 97/29183 disclose a method of making engineered APCs by transfecting professional or non-professional APCs with selected antigens to regulate the immune response of a subject.

WO 96/27392, U.S. Pat. Nos. 5,225,042, 6,251,627 and 5,962,320 disclose engineered APCs transfected with MHC molecules.

SUMMARY OF THE INVENTION

The present invention provides modified antigen-presenting cells (APCs) expressing one or more selected antigens for generating or enhancing an antigen-specific immune response, and methods for making such APCs. The selected antigens are highly expressed on the surface of the cells. The APCs can also be modified to express one or more other immunomodulatory molecules. The APCs of the invention can be used in the treatment of a variety of diseases including microbe infections, cancers and pathologies associated with transplantation.

In one embodiment, the invention provides an animal cell comprising a nucleic acid encoding an exogenous antigen-presenting molecule (e.g., a class I or a class II molecule) and a nucleic acid encoding an antigen fused in frame at its N-terminus to a heterologous reporter polypeptide, wherein the animal cell functions as a professional APC. The heterologous polypeptide aids in the efficient presentation of the antigen on the surface of the cell. In a preferred embodiment, the antigen is fused to the heterologous polypeptide through a linker polypeptide which is cleavable by a cell-associated protease, separating the antigen from the heterologous polypeptide. The cell-associated protease can be an endogenous protease (e.g., such as trypsin) or an exogenous protease (not naturally expressed by the cell) which is expressed by a nucleic acid encoding the exogenous protease which is introduced into the cell. The linker itself can encode a protease (i.e., the linker can be a self-cleaving linker). Most preferably, the C-terminus of the antigen-heterologous polypeptide fusion, or antigen-linker-heterologous polypeptide fusion, is the C-terminus of a minimal antigen sequence, i.e., the C-terminus of the smallest peptide which binds to an antigen-presenting molecule and which upon binding elicits an immune response (e.g., such as an antigen-specific cytotoxic T cell response).

The heterologous polypeptide can be used to provide a selectable marker enabling selection and purification of cells comprising the antigen-encoding nucleic acid. In one aspect, the heterologous polypeptide is a reporter polypeptide such as Green Fluorescent Protein (GFP) or Enhanced Green Fluorescent Protein (EGFP). In another aspect, the heterologous polypeptide comprises a portion of a cell surface protein which is expressed on the surface of a cell, enabling cells which comprise the nucleic acid to be selected for by screening for cells which bind to an antibody specific for the portion of the cell surface protein. The heterologous polypeptide also can provide a function (e.g., such as G418 resistance) which enables cells to survive in a particular type of selection medium (e.g., G418). While "function" in the sense of a reporter or selectable molecule is desirable, the primary function of the heterologous fusion polypeptide that is fused N-terminal to the antigen sequence is to aid in the efficient presentation of the antigen at the cell surface in association with a class I molecule. Thus, cells comprising the nucleic acid can be identified and selected based on their ability to function as APCs (e.g., generating an antigen-specific immune response).

The APC in the above embodiment further can comprise a nucleic acid encoding an exogenous immunoregulatory molecule.

In another embodiment, the invention provides an animal cell comprising a nucleic acid encoding an exogenous immunoregulatory molecule and a nucleic acid encoding an antigen which is expressed on the surface of the cell. The animal cell functions as a professional APC. Preferably, as above, sequence of the antigen is fused in frame at its N-terminus with a heterologous polypeptide and aids in the efficient presentation of the antigen at the cell surface in association with a class I molecule. In one aspect, the heterologous polypeptide is a reporter polypeptide. Preferably, the C-terminus of the antigen is the C-terminus of the antigen-heterologous polypeptide fusion.

Preferably, the immunoregulatory molecule is selected from the group consisting of a costimulatory molecule, an accessory molecule, a cytokine, a chemokine, an adhesion molecule, and combinations thereof. More preferably, the costimulatory molecule is CD80. Still more preferably, the accessory molecule is CD83.

The APC in the above embodiment further may comprise a nucleic acid encoding an antigen-presenting molecule such as a class I or class II molecule. In one aspect, the nucleic acid encodes an exogenous antigen-presenting molecule (e.g., an antigen-presenting molecule not naturally found in the cell).

In one embodiment, antigen-presenting molecule is a class I molecule which is an HLA molecule. In another embodiment, the class I molecule is an H-2 molecule.

Preferably, the antigen presented by the APC is a tumor-specific antigen.

The APC can be a dendritic cell, a macrophage, a B cell, a mast cell, a parenchymal cell, a kupffer cell, or a fibroblast cell. Preferably, the APC is an immortalized cell. Most preferably, the APC is a human cell.

The invention also provides a method for producing a modified APC comprising contacting a population of animal cells with a nucleic acid encoding an antigen which is efficiently presented on the surface of a cell, and selecting a cell which comprises the nucleic acid, presents the antigen on its surface; and functions as a professional APC.

In one aspect, the antigen is fused in frame to a heterologous polypeptide (such as a reporter polypeptide), preferably via a linking polypeptide which is cleavable by a cell-associated protease, as described above. In a preferred aspect, the population of cells also is contacted with a nucleic acid encoding an exogenous antigen-presenting molecule (e.g., a class I or class II molecule not naturally expressed by the cell).

In another embodiment, the invention provides a method for producing a modified APC comprising contacting a population of animal cells with a nucleic acid encoding an exogenous immunoregulatory molecule and a nucleic acid encoding an antigen which is presented on the surface of a cell, and selecting a cell which comprises the nucleic acid encoding the antigen and the nucleic acid encoding the immunoregulatory molecule, presents the antigen on its surface and which functions as a professional APC.

As above, the antigen can be fused in frame to a heterologous polypeptide such as a reporter polypeptide and is preferably linked to the heterologous polypeptide by a linker polypeptide cleavable by a cell-associated protease, such as trypsin. The method further may comprise contacting the population of cells with a nucleic acid encoding an exogenous antigen-presenting molecule such as a class I or class II molecule and selecting one or more cells which express the exogenous immunoregulatory molecule, the antigen, and the antigen-presenting molecule.

Preferably, the immunoregulatory molecule is selected from the group consisting of a costimulatory molecule, an accessory molecule, a cytokine, a chemokine, an adhesion molecule, and combinations thereof.

The contacting in step may be performed by providing the nucleic acids in any of: a viral particle (e.g., an adenovirus or retrovirus), a liposome, and a particle comprising a ligand specific for a receptor expressed by the cells. The nucleic acids also can be provided as naked nucleic acids. Cells can be contacted with the nucleic acid encoding the immunoregulatory molecule, the nucleic acid encoding the exogenous antigen-presenting molecule, and the nucleic acid encoding the antigen simultaneously or sequentially in any order.

In a preferred embodiment, the method for producing a modified APC further comprises establishing clonal populations of the one or more selected cells, exposing the populations to cytotoxic T cells which specifically recognize the antigen and monitoring cell death in the populations.

One embodiment of the invention provides a method for activating an immune effector cell against a selected peptide comprising providing any of the modified APCs described above, and contacting the APCs with an immune effector cell, thereby activating the immune effector cell. Preferably, the immune effector cell is selected from the group consisting of lymphocytes, macrophages, and neutrophils.

The invention also provides a method for modulating an immune response in a subject comprising administering a therapeutically effective amount of any of the modified APCs described above to the subject. In one aspect, the method comprises contacting an immune effector cell with any of the modified APCs described above, thereby activating the immune effector cell, and transplanting the immune effector cell to the subject. The immune effector cell can be obtained from the same subject who is to receive the modified APC or from a different subject. In one aspect, when immune effector cells are obtained from a different subject, the different subject has an antigen-presenting molecule which matches that of the first subject (e.g., the subject has a matching MHC class I determinant). Preferably, the APCs comprise human cells.

The invention further provides kits comprising a plurality of different APCs expressing the same antigen-heterologous polypeptide fusion or antigen-linker-heterologous polypeptide fusion, but each cell expressing a different antigen-presenting molecule. Alternatively, the kit can comprise a plurality of different APCs, each cell expressing a different antigen-presenting molecule and at least one nucleic acid encoding an antigen-heterologous polypeptide fusion or antigen-linker-polypeptide fusion for introducing into the cell. The kit also can comprise one or more nucleic acid molecules encoding one or more immunoregulatory molecules, or antigen-presenting molecules.

BRIEF DESCRIPTION OF DRAWINGS

The objects and features of the invention can be better understood with reference to the following detailed description and accompanying drawings.

FIG. 12 shows the expression of transduced HLA-A2, CD80 and CD83 genes in MEA1 cells.

FIG. 13 shows a schema for CTL generation according to the invention.

FIG. 14 shows the expansion of antigen specific T cells; specific for the Flu, MP58 antigen.

FIG. 15 shows the expansion of antigen specific T cells, specific for the MART-1, M27 antigen.

FIG. 16 shows the cytotoxicity of peptide pusled T2 targets.

FIG. 17 shows the results of ELISPOT measurements of γ-interferon secretion.

FIG. 18 shows the phenotype of multimer stained "young" CTL cells.

FIG. 19 shows the retention of long term effector function of the NY-ESO-1 and Her-2/neu CTL cell lines.

FIG. 20 shows the results from Vβ subtyping, indicating that for the NY-ESO-1 long lived cell line, a single Vβ subtype, Vβ 17 is identified.

FIG. 21 presents the phenotype of long lived NY-ESO-1 multimer$^+$ T cells.

DETAILED DESCRIPTION OF THE INVENTION

Figure 1:
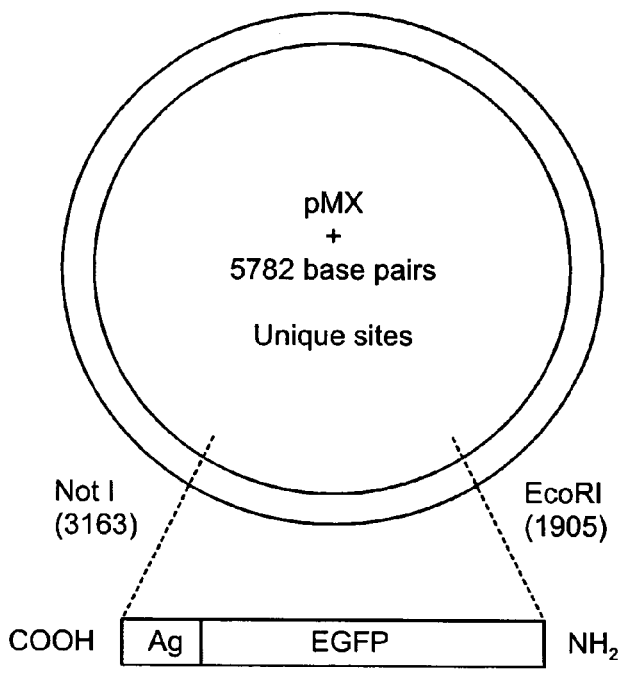
FIG. 1 shows a schematic diagram of a cloning vector for generating GFP-antigen fusions according to one aspect of the invention.
Figure 2:
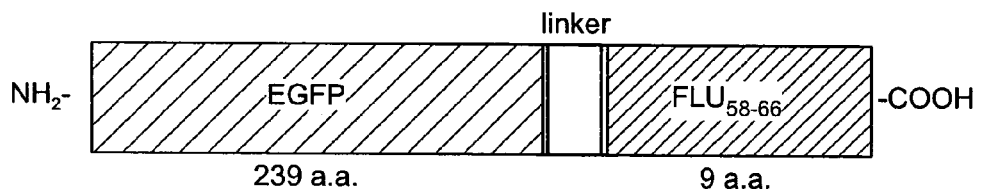
FIG. 2 shows schematic diagrams of two exemplary embodiments of antigen-heterologous fusion polypeptides for generating antigen presenting cells as described herein, relative to a control construct (bottom). "EGFP" refers to the enhanced GFP polypeptide. "Flu$_{58-66}$" and "Mart1$_{27-35}$" refer to nonapeptide antigen sequences corresponding to amino acids 58-66 of Influenza virus MP1 antigen and amino acids 27-35 of the MART1 melanoma-associated tumor antigen, respectively.
Figure 2:
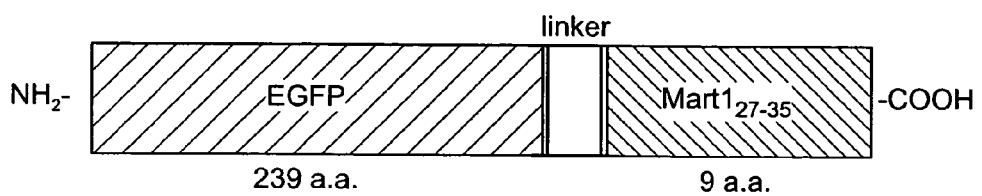
Figure 2:
Figure 3:
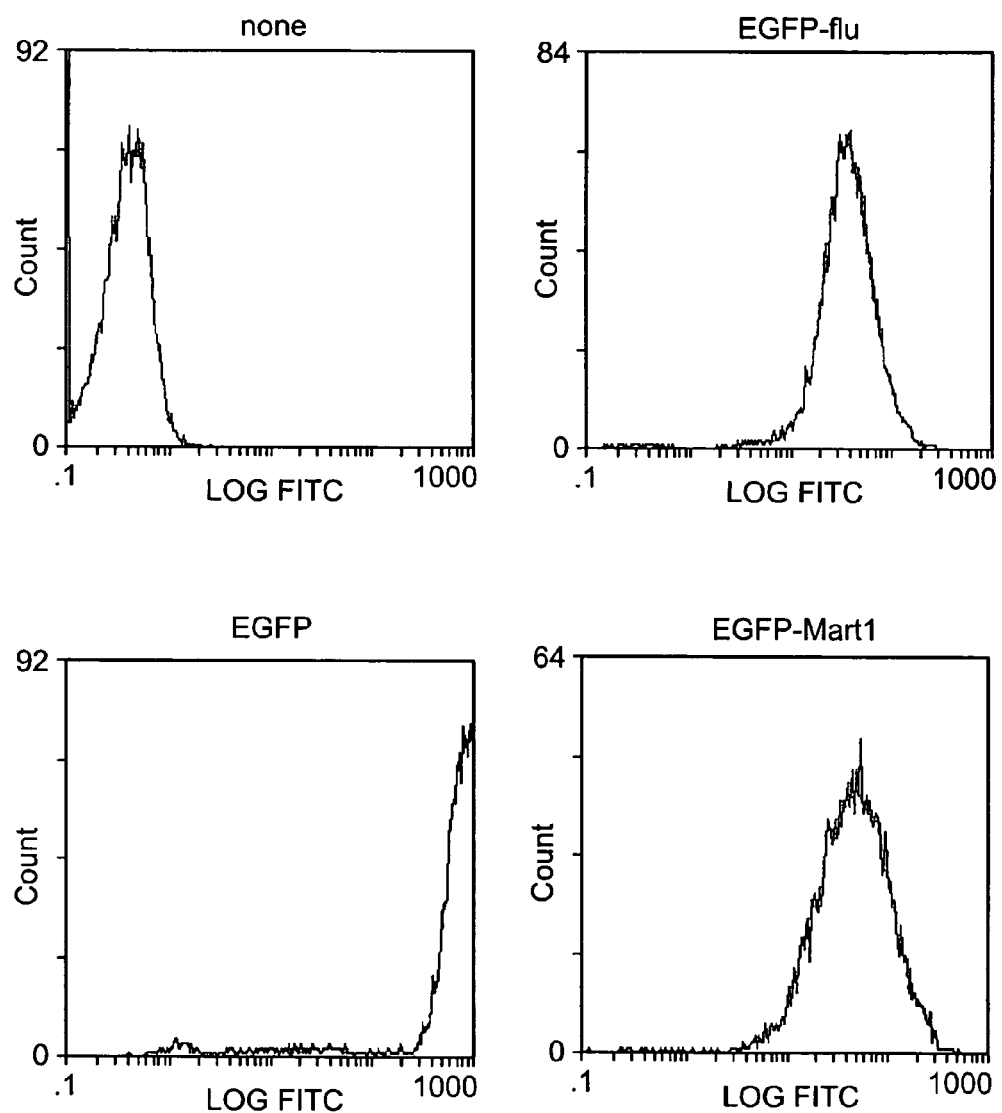
FIG. 3 shows the expression of the polypeptides shown schematically in FIG. 2, as measured by fluorescence of the EGFP fusion partner.
Figure 4:
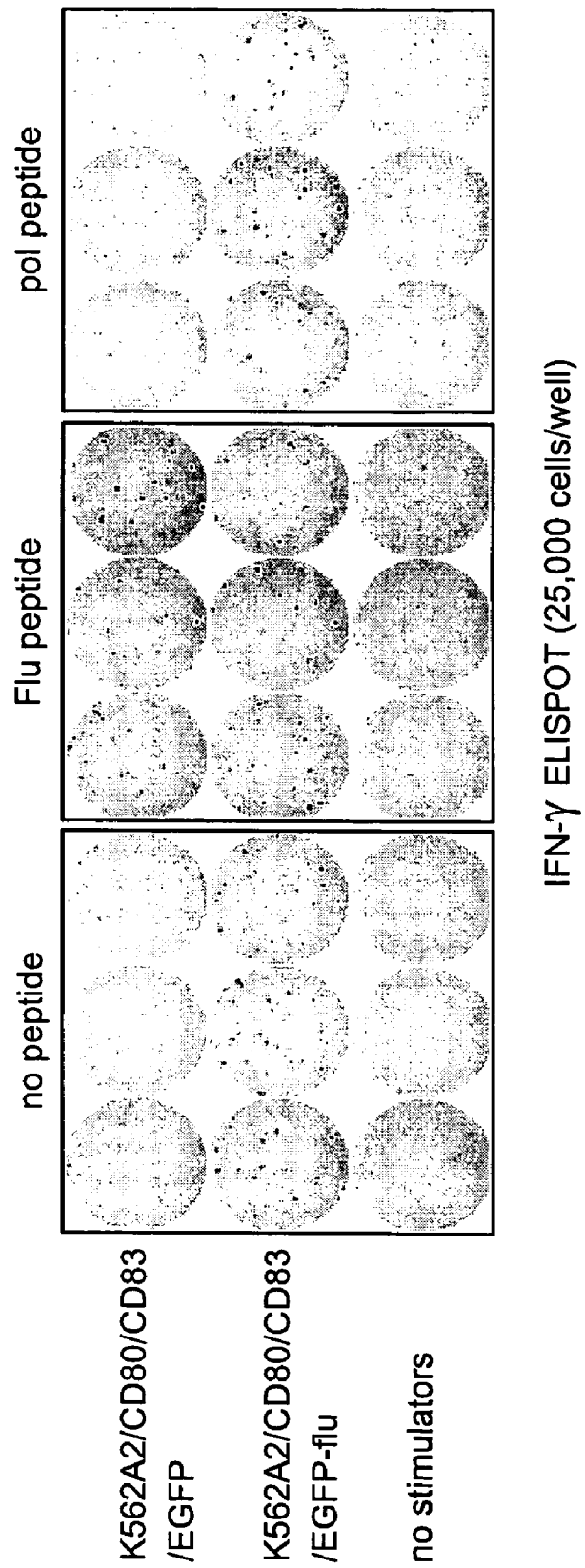
FIG. 4 shows that EGFP-flu is expressed, processed and presented in the leukemia cell line K562/A2 that expresses CD80 and CD83, as measured by T-cell activation assay (induction of IFN-γ secretion).
Figure 5:
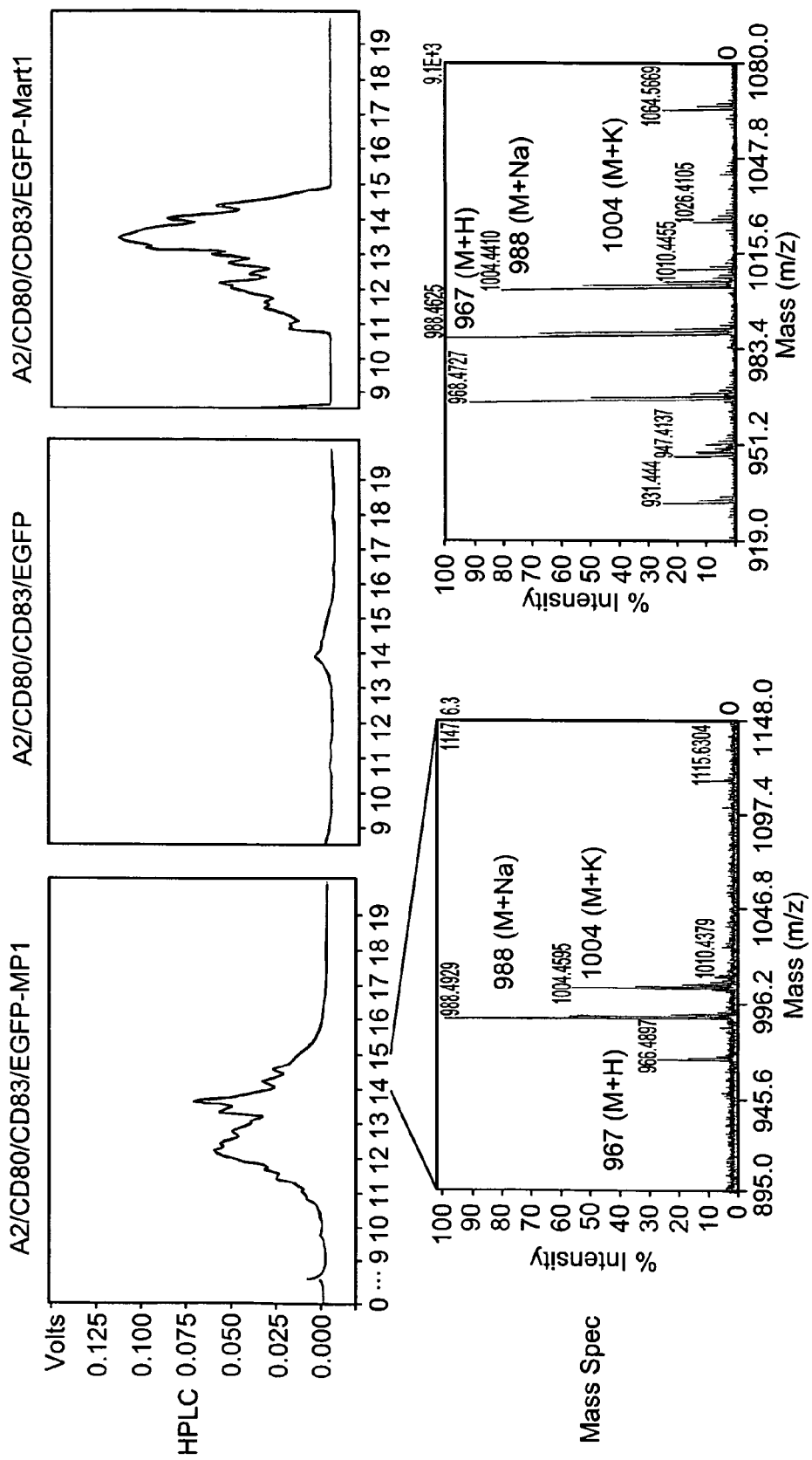
FIG. 5 shows HPLC analyses of eluted antigenic peptides expressed on the surface of K562/A2/CD80/CD83 cells expressing the EGFP-Flu (MP1), EGFP and EGFP-Mart1 constructs shown in FIG. 2, and mass spectroscopy comparison of the eluted influenza virus MP$_{58-66}$ antigen versus synthetic MP$_{58-66}$. The transduced and processed peptide expressed on the transduced cells has a similar mass spectroscopy spectrum to the synthetic antigenic peptide.
Figure 6:
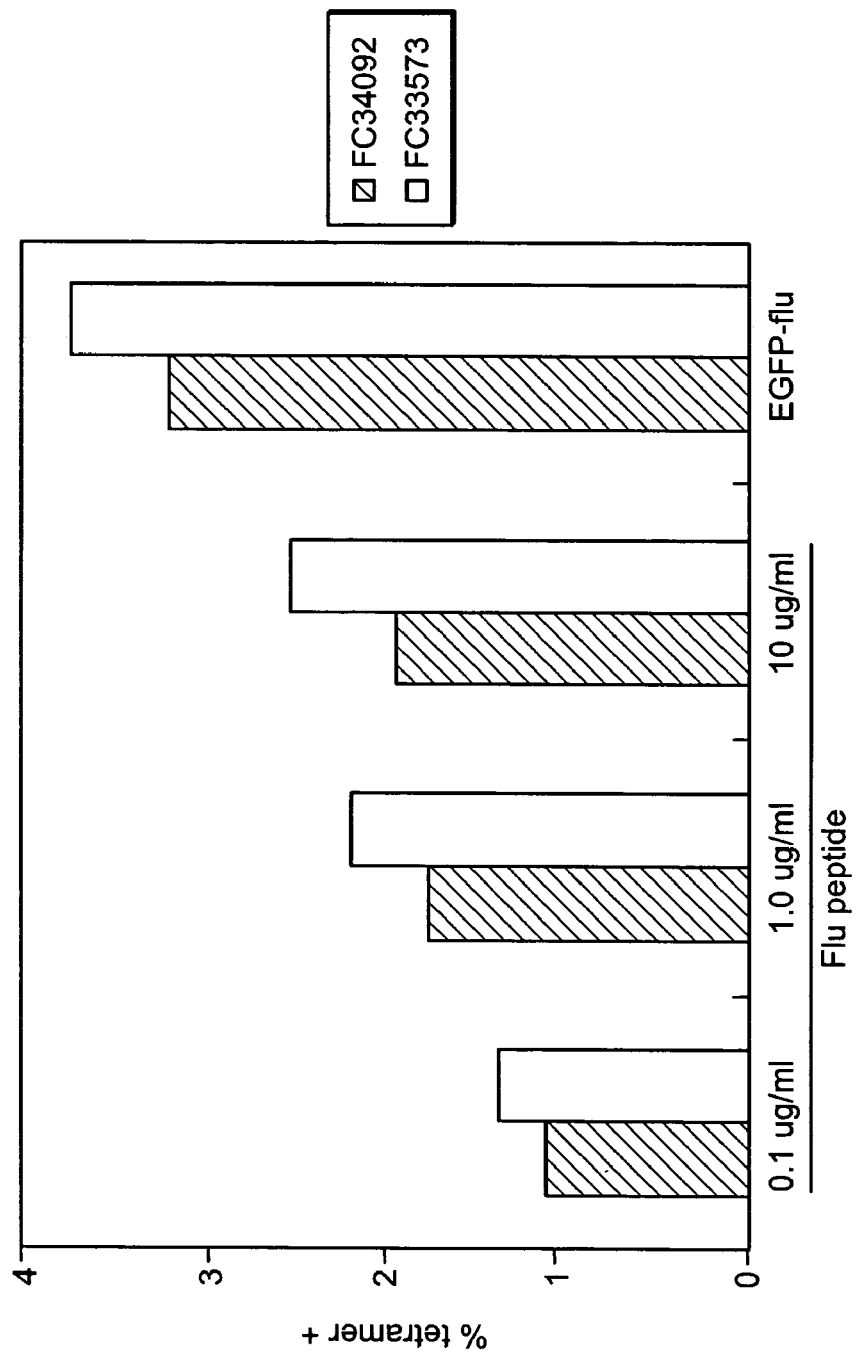
FIG. 6 shows the results of a comparison of memory CD8 T cell activation by two populations of K562/A2/CD80/CD83 antigen presenting cells that were each either pulse-loaded with influenza MP1 peptide (58-66) (at doses of 0.1 μg/ml, 1.0 μg/ml and 10 μg/ml) or transduced with an EGFP-flu$_{58-66}$ construct. The cells transduced with the EGFP-flu construct were stimulated more potently by the cells expressing the EGFP-flu construct than by any of the peptide-pulsed cells.
Figure 7:
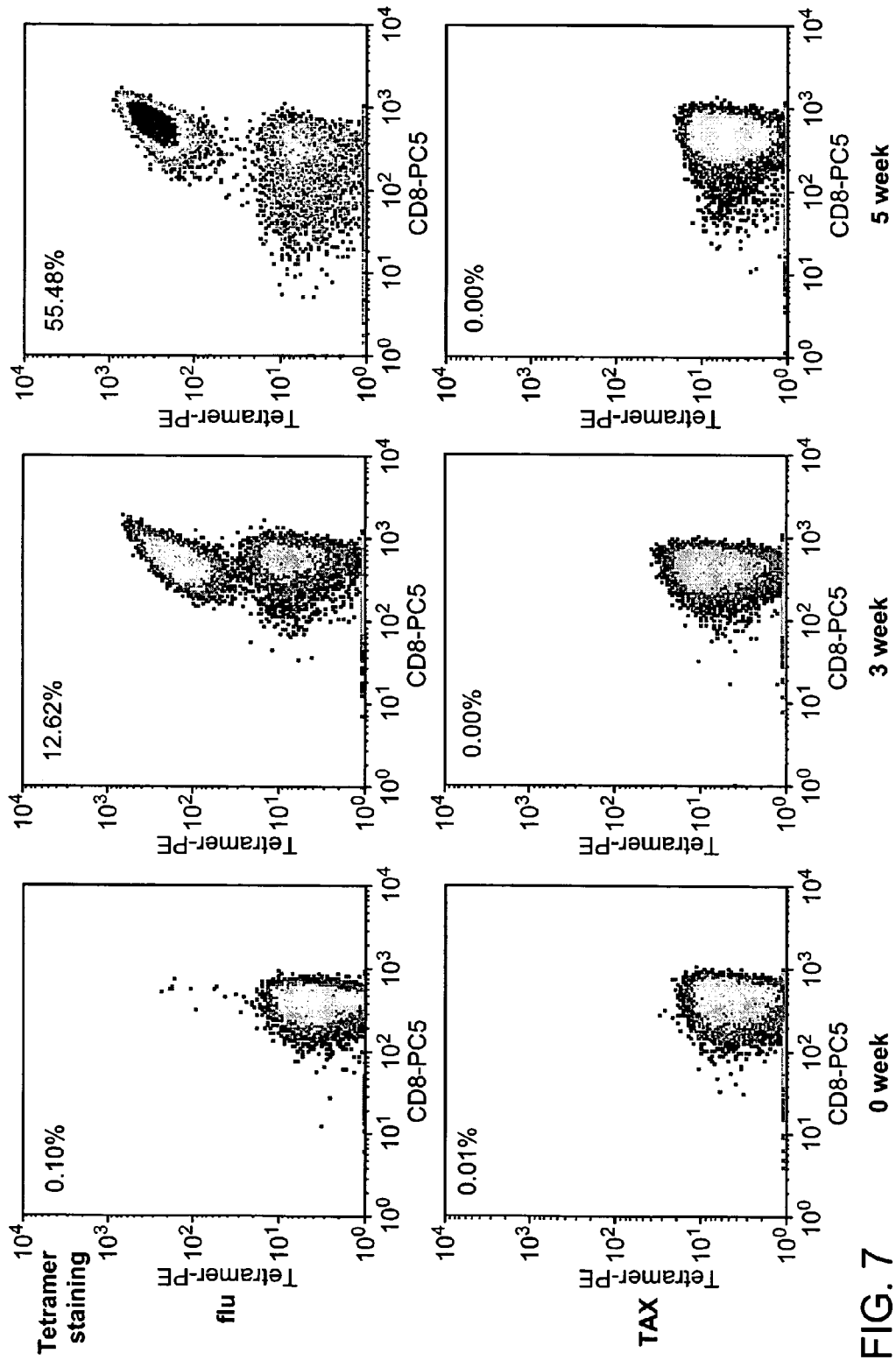
FIG. 7 shows the results of flow sorting of memory cytotoxic T lymphocytes stimulated by K562/A2/CD80/CD83 cells transduced with EGFP-flu. The population of Flu-specific CTLs is dramatically induced by the transduced EGFP-flu, relative to the induction of CTLs specific for a control antigen.
Figure 8:
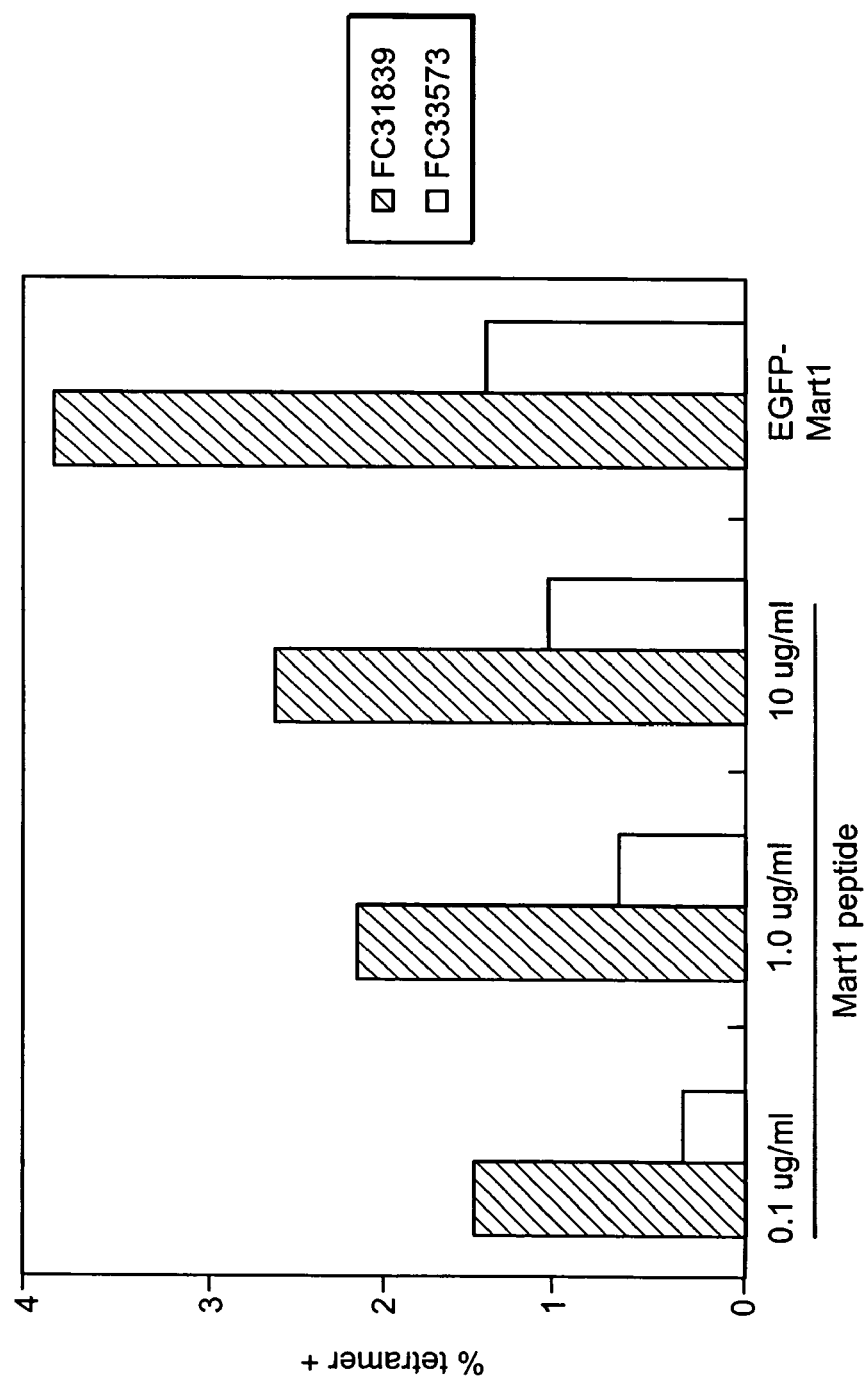
FIG. 8 shows the results of a comparison of naive CD8 T cell activation by two populations of K562/A2/CD80/CD83 antigen presenting cells that were each either pulse-loaded with Mart1 peptide (27-35) (at doses of 0.1 μg/ml, 1.0 μg/ml and 10 μg/ml) or transduced with an EGFP-Mart1$_{27-35}$ construct. In each case, the cells transduced with the EGFP-Mart1$_{27-35}$ construct were stimulated more potently by the cells expressing the EGFP-Mart1$_{27-35}$ construct than by any of the peptide-pulsed cells.
Figure 9:
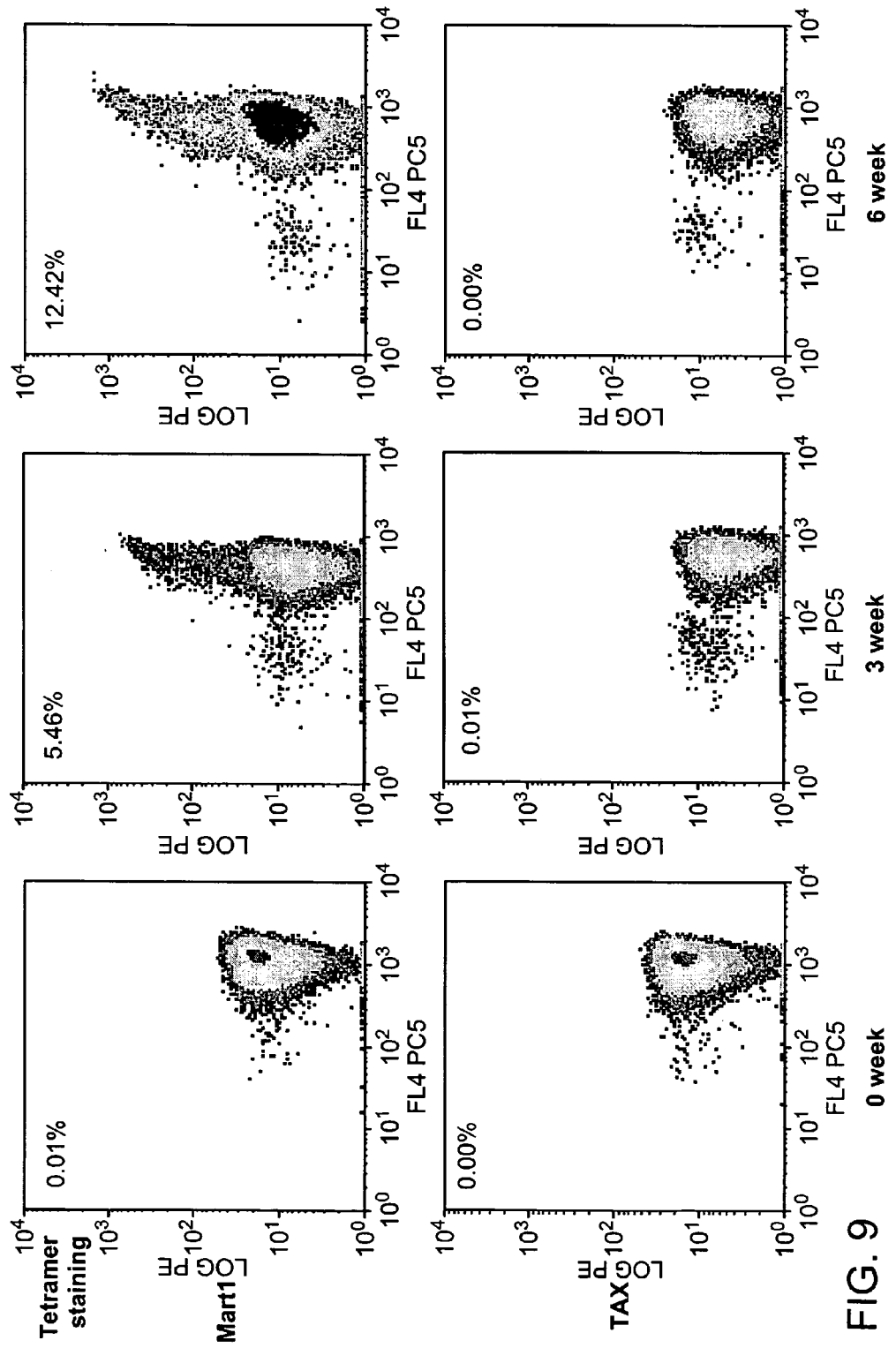
FIG. 9 shows the results of flow sorting of naive cytotoxic T lymphocytes stimulated by K562/A2/CD80/CD83 cells transduced with EGFP-Mart1$_{27-35}$. The population of Mart1$_{27-35}$-specific CTLs is dramatically induced by the transduced EGFP-Mart1$_{27-35}$, relative to the induction of CTLs specific for a control antigen.
Figure 10:
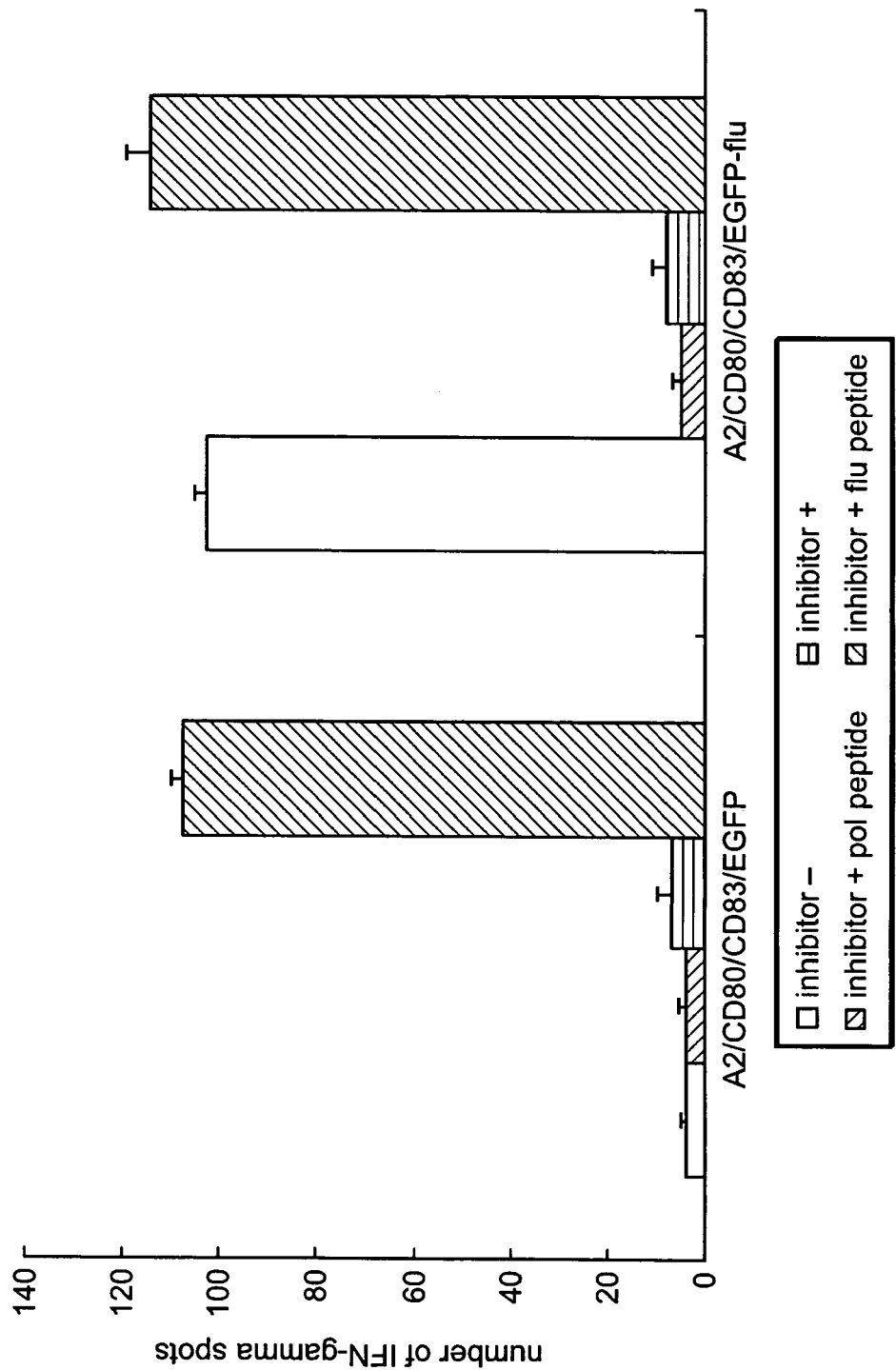
FIG. 10 shows the results of experiments examining the proteasome-dependency of the processing and presentation of Flu peptide by K562/A2/CD80/CD83/EGFP and/EGFP-flu cells. K562/A2/CD80/CD83 cells transduced with either EGFP or EGFP-Flu construct were treated with proteasome inhibitor, with or without pulsed control peptide ("pol peptide") or flu peptide ("flu peptide"). Treated cells were monitored for their ability to activate IFN-γ expression by T cells (ELISPOT assay). Cells expressing EGFP alone failed to activate T cells, with or without proteasome inhibitor, while EGFP-transduced cells pulse loaded with flu peptide activated T cells efficiently. In contrast, cells expressing EGFP-flu activated T cells; this activation was inhibited by proteasome inhibitor, while flu peptide pulse loaded cells activated T cells even when treated with proteasome inhibitor. Thus, processing of EGFP-flu to present the flu antigen appears to be proteasome dependent.
Figure 11:
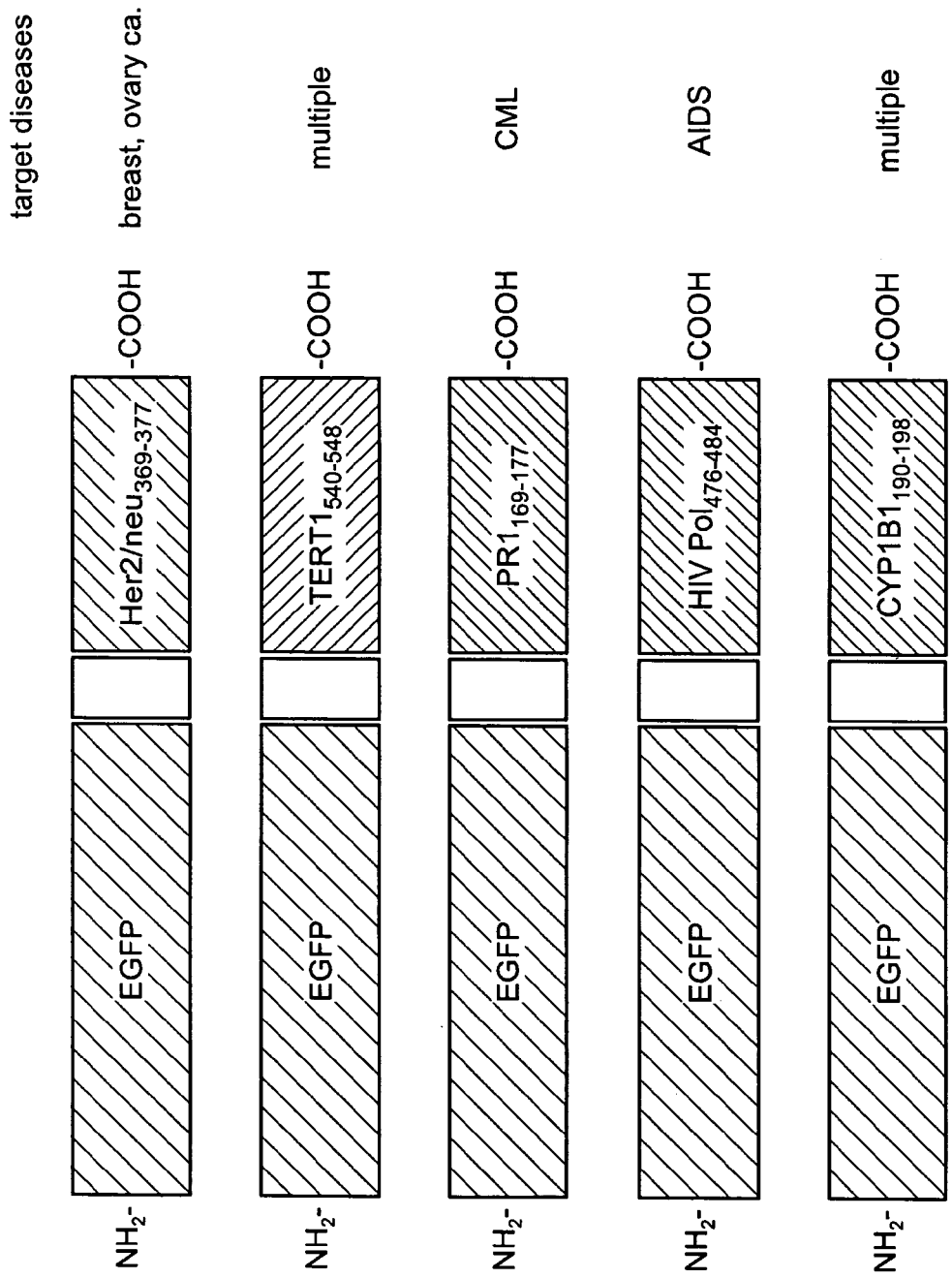
FIG. 11 shows schematic diagrams of additional antigen-heterologous fusion polypeptide constructs for antigen presentation. Antigens include Her2/neu$_{369-377}$ (for breast and ovarian cancer therapies), TERT1$_{540-548}$ (for multiple disease therapies), PR1$_{169-177}$ (for chronic myelogenous leukemia therapies), HIV polymerase$_{476-484}$ (for AIDS therapies), and CYPIB 1190-198 (for multiple disease therapies).

The present invention overcomes traditional problems associated with immunoregulatory reagents by coupling selected antigens and selected MHC molecule matching a specific subject in a modified antigen-presenting cell. The increased efficiency and specificity provided by the present invention can allow for a reduction in antigen dose provided in a vaccine, a more specific and consistent response and consistent avoidance of unwanted side effects caused by conventional antigen-presenting methods. In addition, the present invention allows quantitatively monitoring doses of antigen so that the amount of antigen delivered can be controlled according to specific clinical needs of a subject.

DEFINITIONS

The following definitions are provided for specific terms which are used in the following written description and claims.

As used herein, the term "antigen-presenting cells" or "APCs" refers to a class of cells capable of presenting antigen to cells of the immune system that are capable of recognizing antigen when it is associated with a major histocompatibility complex molecule. APCs mediate an immune response to a specific antigen by processing the antigen into a form that is capable of associating with a major histocompatibility complex molecule on the surface of the APC.

As used herein, an "antigen-presenting molecule" refers to a class I or class II molecule or any other molecule capable of binding to an antigen, presenting the antigen on the surface of a cell, and being recognized by cell(s) of the immune system as a complex of antigen and antigen-presenting molecule.

A "professional APC" (PAPC) functions physiologically to present antigen in a form that is recognized by specific T cell receptors so to trigger a T cell mediated immune response. PAPCs not only process and present antigens in the context of MHC, but also possess the additional immunoregulatory molecules required to complete T cell activation, rendering them critical to the development of a full T cell-directed immune response. A professional APC includes, but is not limited to, a macrophage, B lymphocyte, dendritic cell, mast cell, parenchymal cell and Kupffer cell. A non-professional APC is any animal cell that does not function physiologically as an APC. Nonprofessional APCs lack one or more of the immunoregulatory molecules required to complete the process of T cell activation.

As used herein, the term "antigen" includes peptides, nucleoproteins, nucleic acids, polysaccharides and analogues of these molecules. The term analogue includes the above-identified antigens which have been modified, e.g., by chemical agents or enzymatic cleavage, synthetic molecules containing all or part of the above-identified antigens, as well as hybrid molecules, e.g., molecules containing portions of at least two different antigens. Analogues are prepared using chemical or biochemical synthesis methods, e.g., by employing cloning techniques, according to methods within the ordinary skill of the art. In general, an antigen is any molecule which can elicit an immune system response. Thus, the term antigen includes autologous antigens, (e.g., such as circulating tissue antigens associated with an autoimmune disease) and cancer antigens that are present in autologous cancer cells but are not expressed in a non-neoplastic state, as well as exogenous antigens. Preferably, an antigen comprises the minimal amino acid sequence which associates with a Class I or Class II MHC molecule.

An antigen "presented at the cell surface" is an antigen present on the external surface of a cell in association with an antigen-presenting molecule. Thus, an antigen "presented at the cell surface" can encompasses any antigen presented in association with an antigen presenting molecule (e.g., a class I molecule), regardless of whether or not that antigen is normally part of a cell surface polypeptide.

As used herein, an "immunogenic peptide" or "antigenic peptide" is a peptide which will bind an MHC molecule to form an epitope recognized by a T cell, thereby inducing a CTL response upon presentation to the T cell. Thus, antigenic peptides are capable of binding to an appropriate MHC molecule and inducing a cytotoxic T cell response, e.g., cell lysis or specific cytokine release against the target cell which binds or expresses the antigen.

As used herein, a "tumor-specific antigen" refers to an antigen which is specific for a spontaneous tumor and is absent or present in a smaller amount in normal tissues, or an antigen encoded by nucleic acids associated with a causative agents of the tumor (e.g., such as an oncogenic virus).

The term "self antigen" or "autoantigen," means an antigen or a molecule capable of being recognized during an immune response as self (i.e., an antigen that is normally part of the subject which does not normally trigger an immune response in the subject). This is in contrast to antigens which are foreign, or exogenous, and which are thus not normally part of the subject's antigenic makeup.

As used herein, "recombinant" antigens refer to antigens produced by recombinant DNA techniques; i.e., produced from cells transformed by an exogenous DNA construct encoding the antigen. "Synthetic" antigens are those prepared by chemical synthesis. The term "recombinant" when used with reference to a cell indicates that the cell replicates or expresses a nucleic acid, or expresses a peptide or protein encoded by a nucleic acid, whose origin is exogenous to the cell. Recombinant cells can express genes that are not found within the native (non-recombinant) form of the cell.

As used herein, an "engineered" or "modified" APC is a professional or non-professional APC which is modified to function as a professional APC for one or more selected antigens. A modified APC according to the invention comprises a nucleic acid encoding a selected antigen fused in frame to a reporter polypeptide and a nucleic acid encoding an exogenous class I molecule. The modified APC can further comprise a nucleic acid encoding an exogenous immunoregulatory molecule. The MHC molecule or the immunoregulatory molecule also can be fused in frame to a reporter polypeptide.

A "modified APC", according to the invention, can also be a professional APC which is modified to have an enhanced antigen-presenting activity, e.g., capable of triggering an immune response which is at least 10%, 20%, 30% 40%, 50% 100% or more (e.g., 2-fold, 3-fold, 4-fold, 5-fold, 10-fold, or more) than that triggered by the unmodified professional APC (e.g., as measured by a T cell proliferation assay or a cytotoxic T lymphocyte (CTL) assay). In one aspect, a modified APC according to the invention is one which causes a specific cytotoxic response, killing at least 10% more cells comprising a target antigen ("target cells") than control cells (e.g., 60% killing of a target cells compared to 50% killing of a control target), or in another aspect, killing at least twice as many target cells as control cells (e.g., 7% killing of a target cell compared to 3.5% killing of control cells).

A "modified APC" according to the invention can also be a vesicle, e.g., liposome, having a lipid bilayer membrane resembling the lipid bilayer of a naturally occurring cell. The liposome further includes a nucleic acid encoding a selected antigen fused in frame to a reporter polypeptide, and a MHC class I molecule associated with the lipid bilayer and/or other immunoregulatory molecules to function as an APC. The MHC class I molecule or the immunoregulatory molecule can be fused in frame to a reporter polypeptide.

As used herein, "TAP protein" refers to any of the ATP-binding MHC-encoded polypeptides that translocates antigenic peptides, as described by Momburg et al., for example (Momburg, et al., 1994, Curr. Opin. Immunol., 6:32-37, hereby incorporated by reference). Preferably, the gene encoding the TAP protein has at least 80%, more preferably 90%, and most preferably 100%, sequence identity to the previously reported human or murine TAP-1 or TAP-2 genes (see, e.g., Trowsdale et al., 1990, Nature, 348: 741-748, GenBank Accession No. X57522).

An "immune response" to an antigen is the development in a subject of a humoral and/or a cellular immune response to the antigen of interest. A "cellular immune response" is one mediated by T cells and/or other white blood cells.

As used herein, the term "cytotoxic T cell" refers to a subset of T lymphocytes that can kill cells expressing a class I-presented antigen such as cells infected by viruses or transformed cancer cells. CTLs have specificity for peptide antigens that are presented in association with proteins encoded by the MHC class I genes and which are expressed on the surfaces of cells. CTLs help induce and promote the destruction of intracellular microbes (e.g., such as viruses), or the lysis of cells infected with such microbes.

As used herein, the term "helper T cell" refers to a subset of T cells that typically carry the CD4 marker and are essential for turning on antibody production, activating cytotoxic T cells, and initiating many other immune responses.

T cells, after being activated by an APC modified to present a selected antigenic peptide, recognize the antigenic peptides bound to the MHC class I molecule and kill a cell which expresses the selected antigenic peptide, either by cell lysis (e.g., "cytotoxic T cells"), or by recruiting other immune cells to the site of the target cell by releasing cytokines (e.g., "T helper cells"). The T cells which recognize the antigenic peptide-MHC molecule are induced to proliferate in response to APCs which express corresponding antigenic peptides on their cell-surface MHC molecules. The above activated T cells are referred to as being "against the selected antigen" or "specific for the selected antigen".

A "target protein" is a protein which comprises antigenic peptide subsequences. These subsequences are expressed on target cells in the context of MHC molecules. T cells recognize epitopes formed by the binding of an MHC molecule to these peptide subsequences and typically lyse the cell, or recruit other immune cells (e.g., macrophage) to the site of the target cell, thereby killing the target cell.

The term "major histocompatibility complex (MHC) molecule" refers to an antigen-presenting molecule on an APC that has the ability to associate with the antigen to form an antigen-associated APC. In a preferred embodiment, the major histocompatibility complex molecule is a class I or class II molecule.

The term "immune effector cell" refers to the cells of the immune system that mount responses to an antigen, see Fundamental Immunology, 1998, Third Edition, p. 181. Preferred effector cells of the invention are populations of cytotoxic T cells and T helper cells that mediate cellular immunity. In addition to antigen-specific effector T cells, the effector cell populations of the invention may include, but are not limited to, other cytotoxic immune cells against a selected antigen: lymphocytes, monocytes, macrophages, neutrophils, and eosinophils (Morton, et al., 1996, Critical Reviews in Immunology, 16:423; Morton, et al., 1996, Critical Reviews in Immunology, 16:423).

As used herein, the term "immunoregulatory molecules" refers to any molecule occurring naturally in animals that may regulate or directly influence immune responses including proteins involved in antigen processing and presentation such as TAP 1/TAP2 transporter proteins, proteosome molecules such as LMP2 and LMP7, heat shock proteins such as gp96, HSP70 and HSP90, and MHC or HLA molecules; factors that provide co-stimulation signals for T cell activation such as B7 molecules and CD40; accessory molecules such as CD83; chemokines; lymphokines and cytokines such as interferons $\alpha$, $\beta$ and $\gamma$, interleukins (e.g., IL-2, IL-7, IL-12, IL-15, IL-22, etc.), factors stimulating cell growth (e.g., GM-CSF), and other factors (e.g., tumor necrosis factors, DC-SIGN, MIP1$\alpha$, MIP1$\beta$, TGF-$\beta$ or TNF).

As used herein, the term "regulatory element" refers to a genetic element which controls the expression of nucleic acid sequences. For example, a promoter is a regulatory element which directs the transcription of an mRNA. Other regulatory elements include enhancers, splicing signals, polyadenylation signals, transcription termination signals, upstream regulatory domains, origins of replication, internal ribosome entry sites (IRES), etc. Not all of these control sequences need always be present so long as a selected coding sequence is capable of being replicated, transcribed and translated in an appropriate recipient cell.

As used herein, the term "promoter/enhancer" refers to a segment of DNA which contains sequences capable of providing both promoter and enhancer functions (i.e., the functions provided by a promoter element and an enhancer element). For example, the long terminal repeats of retroviruses contain both promoter and enhancer functions. The promoter/enhancer may be "endogenous" or "exogenous" or "heterologous."

An "endogenous" promoter/enhancer is one which is naturally linked with a given gene in the genome. An "exogenous" or "heterologous" promoter/enhancer is one which is placed in juxtaposition to a gene by means of genetic manipulation (i.e., molecular biological techniques) such that transcription of that gene is directed by the linked promoter/enhancer.

As used herein, the term "operably linked" refers to functional linkage between a nucleic acid regulatory element (such as a promoter, or array of transcription factor binding sites) and a second nucleic acid sequence (such as a nucleic acid encoding an exogenous protein), where the regulatory element directs transcription of the nucleic acid corresponding to the second sequence.

As used herein, the term "fusion protein" refers to two or more coding sequences obtained from different genes, that have been cloned together to maintain a single reading frame and that, after translation, act as a single polypeptide sequence.

As used herein, a "heterologous polypeptide fused in frame to an antigen" refers to an amino acid sequence fused in frame to the amino acid sequence of an antigen and which is not naturally part of the antigen or polypeptide or protein encoding the antigen in a cell. A heterologous polypeptide may be fused directly to the antigen or via a linking polypeptide. The N-terminus of the antigen amino acid sequence is fused to the C terminus of the heterologous polypeptide either directly or through the linker polypeptide. The linking polypeptide comprises at least one bond that is hydrolyzable by a cell-associated protease, but may also comprise non-natural amino acids (e.g., D-amino acids) or modified amino acids. As used herein, an "antigen-heterologous polypeptide fusion" encompasses both an antigen fused directly to a heterologous polypeptide and an antigen fused to a heterologous polypeptide via an intervening linker sequence. The latter type of fusion is more specifically referred to as an "antigen-linker-heterologous polypeptide fusion."

As used herein, the term "reporter molecule" refers to a nucleic acid (e.g., mRNA) or polypeptide product (referred as a "reporter polypeptide") that is detectable when expressed by a subject cell. Preferably, a reporter molecule (e.g., a reporter polypeptide) allows a quantitative measurement of the expression of a nucleic acid sequence. Reporter polypeptides may be proteins capable of emitting light such as Green Fluorescent Protein (GFP) (Chalfie, et al., 1994, Science 11;

263:802-805) or luciferase (Gould, et al., 1988, Anal. Biochem., 15; 175:5-13), or may be intracellular or cell surface proteins detectable by antibodies such as CD20 (Koh, et al., 1995, Nature, 375:506-510). Alternatively, reporter polypeptides can confer resistance to a selection medium such as hygromycin or neomycin resistance (Santerre, et al., 1984, Gene, 30: 147-156). In one aspect, the heterologous polypeptide is a reporter polypeptide which comprises at least the N-terminus of a reporter protein (e.g., such as Green Fluorescent Protein) and a functional domain of the reporter protein (e.g., a portion of the protein capable of emitting light or which otherwise enables it to be detected); i.e., the C-terminus of the reporter polypeptide is not necessarily the natural C-terminus of the reporter protein.

As used herein the term "GFP" refers to a member of a family of naturally occurring fluorescent proteins, whose fluorescence is primarily in the green region of the spectrum. The term includes mutant forms of the protein with altered or enhanced spectral properties. Some of these mutant forms are described in Cormack, et al., 1996, Gene, 173: 33-38 and Ormo, 1996, Science, 273:1392-1395, all of which hereby incorporated by reference. The term also includes polypeptide analogs, fragments or derivatives of GFP polypeptides which differ from naturally-occurring forms by the identity or location of one or more amino acid residues, for example, deletion, substitution and addition analogs, which share some or all of the properties of the naturally occurring forms so long as they generate detectable signals (e.g., fluorescence). Wild type GFP absorbs maximally at 395 nm and emits at 509 nm. High levels of GFP expression have been obtained in cells ranging from yeast to human cells. It is a robust, all-purpose reporter, whose expression in the cytoplasm can be measured quantitatively using instruments such as the FACS. The term also includes BFP, the coding sequence for which is described in Anderson, et al., 1996, Proc. Natl. Acad. Sci. (USA), 93:16, 8508-8511, incorporated herein by reference, and Enhanced GFP (available from Clontech).

As used herein, the term "selectable marker" refers to the use of a gene which encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Polypeptides encoded by selectable marker genes also can be used as heterologous polypeptides according to the invention.

As used herein, a "primary cell" is a cell isolated from a subject or a cell derived by differentiation of a cell taken from a subject. Generally, a primary cell has limited passaging capacity in culture.

As used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells.

As used herein, the term "transformation" or the term "transfection" refers to a variety of art-recognized techniques for introducing exogenous nucleic acid (e.g., DNA) into a cell. A cell is "transformed" or "transfected" when exogenous DNA has been introduced inside the cell membrane. The terms "transformation" and "transfection" and terms derived from each are used interchangeably.

As used herein, the terms "stable transfection" and "stably transfected" refers to the introduction and integration of foreign DNA into the genome of the transfected cell. The term "stable transfectant" refers to a cell which has stably integrated foreign DNA into the genomic DNA.

As used herein, the term "transient transfection" or "transiently transfected" refers to the introduction of foreign DNA into a cell where the foreign DNA does not integrate into the genome of the transfected cell. The foreign DNA persists in the nucleus of the transfected cell for several days. During this time the foreign DNA is subject to the regulatory controls that govern the expression of endogenous genes in the chromosomes.

The term "transient transfectant" refers to cells which have taken up foreign DNA but have failed to integrate this DNA.

As used herein, "isolated" or "biologically pure" refers to material (e.g., nucleic acids used for transfection) which is substantially or essentially free from components which normally accompany it as found in its naturally occurring environment. An isolated material optionally comprises material not found with the components in its natural environment.

As used herein, a "cell receptor ligand" is a biological molecule which binds to a cell receptor (which can be an extracellular receptor or an intracellular receptor), thereby activating the receptor.

The term "nucleic acid" refers to a deoxyribonucleotide or ribonucleotide polymer in either single- or double-stranded form, and unless otherwise limited, encompasses analogues of natural nucleotides that hybridize to nucleic acids in a manner similar to naturally occurring nucleotides. Unless otherwise indicated, a particular nucleic acid sequence optionally includes the complementary sequence thereof.

As used herein, the term "therapeutically effective amount" refers to that amount of an APC that is required to reduce the pathologic effects or symptoms in an animal, for example, at least by 10%, 20%, 45%, 60% or more, compared to an animal not treated with the APC or compared to the same animal before the APC treatment.

As used herein, "modulation" or "modulating" means that a desired/selected response is more efficient (e.g., at least 10%, 20%, 40%, 60% or more), more rapid (e.g., at least 10%, 20%, 40%, 60% or more), greater in magnitude (e.g., at least 10%, 20%, 40%, 60% or greater), and/or more easily induced (e.g., at least 10%, 20%, 40%, 60% or more) than if the antigen had been used alone.

A desired immune response can be stimulation/activation of a selected immune response, e.g., selective enhancement of an immune response to an antigen, or it can be inhibition of a selected immune response e.g., selective suppression, elimination, or attenuation of an immune response to an antigen, or a combination thereof.

As used herein, the term "subject" refers to any animal, while the term "animal subject" refers to any member of the subphylum Chordata. It is intended that the term encompass any member of this subphylum, including, but not limited to humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

As used herein, an "expression vector" refers to a recombinant expression cassette which has a nucleic acid which encodes a polypeptide (i.e., a protein) that can be transcribed and translated by a cell. The expression vector can be a plasmid, virus, or nucleic acid fragment.

A "recombinant expression cassette" is a nucleic acid construct, generated recombinantly or synthetically, with one or more nucleic acid elements which permit transcription of a particular nucleic acid in a target cell. Typically, the recombinant expression cassette portion of the expression vector includes a nucleic acid to be transcribed, and one or more regulatory elements. In some embodiments, the expression cassette also includes an origin of replication, and/or chromosome integration elements such as retroviral LTRs.

An "inducible" regulatory element or an "inducible" expression vector initiates or terminates the expression of a nucleic acid encoding a polypeptide in response to an extracellular stimulus.

The "heterologous polypeptide" may or may not be cleaved from the antigen which is expressed on the surface of the cell. Most preferably, the antigen is a peptide which comprises the minimal number of amino acids required to bind to an antigen-presenting molecule and elicit an immune response (i.e., a "minimal antigen sequence") and the C-terminus of the antigen-heterologous fusion is the C-terminus of the antigen.

As used herein, a "cell-associated protease" is a protease which is in sufficient proximity to a cell to cleave a heterologous polypeptide from the antigen portion of an antigen-heterologous polypeptide fusion (e.g., an antigen-linker-heterologous polypeptide fusion) prior to or after its expression at the cell surface. A cell-associated protease can be an intracellular protease or a protease which is expressed at an extracellular space. An "exogenous cell-associated protease" refers to a protease not naturally expressed in a given cell (for example, a *Bacillus subtillus* protease expressed in a mammalian cell).

As used herein, "matching" a modified APC to a subject or "matching the specificity of an antigen-presenting molecule to an antigen-presenting molecules of a subject" refers to providing a subject with modified APCs which stimulate the subject's T cells in an antigen-specific manner, such that the T cells will react with autologous cells (i.e., tumor or virus-infected host cells) that express the antigen.

Cells for Generating APCs

A variety of cells can be modified according to the invention to make APCs. Preferably, the cell is an animal cell, more preferably, a mammalian cell, such as a human or mouse cell. The cell can be a primary cell, or it can be a cell of an established cell line. It can be a professional APC or a non-professional APC. If desired, a combination of cells can be used in the invention.

Professional APCs ("PAPCs") for use in the invention include any animal cell that functions physiologically to present antigen to T cells and cause T cell activation. These cells include, but are not limited to, macrophages, B cells, monocytes, dendritic cells, and Langerhans cells.

Cells for use in the present invention also include cells that are not professional APCs, including cells of any animal species, whether or not they are known to function as professional APCs, such as activated T cells, fibroblasts, eosinophils, keratinocytes, astrocytes, microglial cells, thymic cortical epithelial cells, endothelial cells, Schwann cells, retinal pigment epithelial cells, myoblasts, vascular smooth muscle cells, chondrocytes, enterocytes, thymocytesi and kidney tubule cells.

The cells useful in the invention may be primary cells recently explanted from a subject and not extensively passaged in cell culture to form a cell line, or cell lines that are relatively homogeneous and capable of proliferating for many generations or indefinitely.

PAPCs can be collected from the blood or tissue of 1) an autologous donor; 2) a heterologous donor having a different MHC/HLA specificity then the subject to be treated; or 3) from a xenogeneic donor of a different species using standard procedures (Coligan, et. al., supra, sections 3 and 14, hereby incorporated by reference). The cells may be isolated from a normal subject or a disease subject having an infectious disease, cancer, autoimmune disease, or allergy.

For example, PAPCs may be obtained from the peripheral blood using leukopheresis and "Ficoll/hypaque" density gradient centrifugation (stepwise centrifugation through Ficoll and discontinuous Percoll density gradients), see for example, as described in Boyuwn, 1968, Scand. J. Clin. Lab. Invest., 21:21-29; Bucala, et al., 1994, Mol. Med., 1: 71-81; Markowicz, et al., 1990, J. Clin. Invest., 85:955. Procedures may be utilized which avoid the exposure of the PAPCs to antigens which could be internalized by the PAPCs, leading to activation of T cells not specific for the antigens of interest (see *Current Protocols in Immunology*, 2001, John Wiley & Sons, Inc., hereby incorporated by reference).

Cells that are not professional APCs are isolated from any tissue of 1) an autologous donor; 2) a heterologous donor or 3) a xenogeneic donor, where they reside using a variety of known separation methods (Darling, 1994, Animal Cells: Culture and Media. J. Wiley, New York; Freshney, 1987, Culture of Animal Cells, Alan R. Liss, Inc., New York, both hereby incorporated by references).

Non-autologous cells, e.g. heterologous or xenogeneic cells, are engineered ex vivo to express antigen-presenting molecules, such as MHC/HLA class I molecules that match known human HLA specificities. These cells can then be introduced into a human subject expressing antigen-presenting molecules matching the specificity of the antigen-presenting molecules of the engineered cells. The cells are preferably further engineered ex vivo to express one or more selected antigens and other molecules (e.g., immunoregulatory molecules such as costimulatory and/or accessory molecules).

Primary cells used in the invention may be engineered to become immortalized cells for use to make APCs. To immortalize the APCs, transforming genes such as oncogenes may be employed. For example the concomitant overexpression of c-myc and another oncogenei such as ras or abl results in a transformation of cells (see for example, Sinkovics, 1988, Crit. Rev. Immunol., 8:217-98; Paul, et al., 1989, Crit. Rev. Oncog., 1:307; hereby incorporated as references).

Cell lines for use in the present invention are obtained from a variety of sources (e.g., ATCC Catalogue of Cell Lines & Hybidomas, 1995, American Type Culture Collection, 8th edition), or are produced using standard methods (Freshney, 1996, Culture of Immortalized Cells, Wiley-Liss, New York, hereby incorporated by reference). Cells can be stored by freezing at −80° C. to −20° C. until they are needed for use.

Preferably, cells used as APCs have endogenous antigen-presenting molecules such as MHC class I molecules or HLA determinants expressed at relatively low levels so that the expression of cell endogenous antigen-presenting molecules (e.g., MHC or HLA molecules) do not interfere with the cell's ability to generate a desired immune response after modification, i.e., the cells remain capable of triggering an immune response which is at least 10%, 20%, 30% 40%, 50% 100% or more (e.g., 2-fold, 3-fold, 4-fold, 5-fold, 10-fold, or more) than that triggered by the unmodified professional APC (e.g., as measured by a T cell proliferation assay or a cytotoxic T lymphocyte (CTL) assay). More preferably, the cells used in the invention do not express MHC class I or HLA determinants (e.g., the determinants not detectable by standard Western blot analysis) or where exogenous class II molecules are introduced into the cells, the cells do not express class II determinants. However, in some aspects, the modified APCs comprise multiple different types of exogenous and/or endogenous antigen-presenting molecule determinants.

The cells do not have to be genotypically negative for antigen-presenting molecule determinants, but preferably do not express antigen-presenting molecules at a level which substantially interferes the binding of transfected antigen-presenting molecule (e.g., an MHC class I or class II molecule) to a selected antigen or the presenting of the selected antigen by the transfected molecule.

The engineered cells can be maintained in cell culture by standard cell culture methods (Darling, supra; Freshney, supra).

Selected Antigens

Antigens useful in the invention can be any type of biologic molecule including, for example, simple intermediary metabolites, sugars, lipids, and hormones as well as macromolecules such as complex carbohydrates, phospholipids, nucleic acids and peptides.

In preferred embodiments of the invention, nucleic acids encoding antigenic peptides are used. Preferably, the nucleic acids encode the minimal antigenic sequence which is required to bind to an antigen-presenting molecule.

Because CTL epitopes usually comprise 8-10 amino acid long (Townsend, et al., 1989, Annu. Rev. Immunol., 7:601-624; Monaco, 1992, Cell, 54:777-785; Yewdell, et al., 1992, Adv. in Immunol., 52:1-123), in one aspect nucleic acids are provided which encode 8-10 amino acids antigenic peptides. Preferably these are fused in frame to reporter polypeptides.

In practicing the invention, conventional methods can be used to predict, identify, and/or prepare antigenic peptides (i.e., antigens or CTL epitopes). Generally, a peptide of 5 to 40 amino acids, preferably 6 to 25 amino acids, more preferably 8 to 10 amino acids, in length is suitable as an antigen. Examples of antigens presented in various immune responses are described in more detail below and are generally known in the art (see, e.g., Engelhard, 1994, Current Opinion in Immunology, 6:13-23, hereby incorporated as reference). Presentation of any of these peptides on the surface of a cell allows the cell to be used to stimulate a CTL response in vitro or in vivo. In the examples described below, a synthetic nucleic acid encoding a peptide corresponding to amino acids 58-66 of flu MP1 antigen was used as the antigenic peptide.

Criteria for identifying and selecting effective antigenic peptides (e.g., minimal peptide sequences capable of eliciting an immune response) can be found in the art. For example, Apostolopoulos et al., 2000, Curr. Opin. Mol. Ther., 2:29-36, discusses the strategy for identifying minimal antigenic peptide sequences based on an understanding of the three-dimensional structure of an antigen-presenting molecule and its interaction with both an antigenic peptide and T-cell receptor. Shastri, 1996, Curr. Opin. Immunol., 8:271-7, disclose how to distinguish rare peptides that serve to activate T cells from the thousands peptides normally bound to MHC molecules.

Antigenic peptides can be purified from any source as described above (e.g., the cleft of an antigen-presenting molecule expressed on the surface of a tumor cell). The sequence of a purified antigenic peptide can be obtained by methods known in the art (e.g., by peptide sequencing, see Walker, 1994, Methods Mol. Biol., 32:329-34; Stults, 1990, Methods Biochem. Anal., 34: 145-201). Nucleic acid sequences can be deduced from the selected peptide and used in the invention.

Nucleic acid sequences encoding antigenic peptides can be obtained using recombinant methods, such as by screening cDNA and genomic libraries from cells expressing the antigen, or by deriving the sequence from a vector known to include the same. Furthermore, the desired sequence can be isolated directly from cells and tissues containing the same, using standard techniques, such as phenol extraction and PCR of cDNA or genomic DNA (See e.g., Sambrook et al., supra, for a description of techniques used to obtain and isolate DNA). Nucleotide sequences encoding an antigen of interest can also be produced synthetically, rather than cloned. Preferably, the nucleic acid sequence encoding the antigen does not encode sequences outside the sequence required for binding to the antigen-presenting molecule.

In one a preferred embodiment, a nucleic acid encoding the antigenic peptide is synthesized chemically. Preferably, the nucleic acid encoding the antigenic peptide is 24 to 30 nucleotides in length and encodes 8-10 amino acids. More preferably, the nucleic acid is linked to another nucleic acid encoding a reporter polypeptide to form a single translation product comprising the reporter polypeptide fused in frame to the antigen. Still more preferably, the reporter polypeptide is fused in frame with the antigen via a linking sequence which can be cleaved by a cell-associated protease.

Viral Antigens

It is contemplated that suitable viral antigens will be derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and HIV (e.g., GenBank Accession No. U18552).

Retroviral antigens derived from HIV include, but are not limited to, antigens such as gene products of the gag, pol, and env genes, the Nef protein, reverse transcriptase, and other HIV components. Hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Influenza viral antigens include, but are not limited to, antigens such as hemagglutinin and neuramimidase and other influenza viral components. Measles viral antigens include, but are not limited to, antigens such as the measles virus fusion protein and other measles virus components. Rubella viral antigens include, but are not limited to, antigens such as proteins E1 and E2 and other rubella virus components; rotaviral antigens such as VP7sc and other rotaviral components. Cytomegaloviral antigens include, but are not limited to, antigens such as envelope glycoprotein B and other cytomegaloviral antigen components. Respiratory syncytial viral antigens include, but are not limited to, antigens such as the RSV fusion protein, the M2 protein and other respiratory syncytial viral antigen components. Herpes simplex viral antigens include, but are not limited to, antigens such as immediate early proteins, glycoprotein D, and other herpes simplex viral antigen components. *Varicella zoster* viral antigens include, but are not limited to, antigens such as gpI, gpII, and other *varicella zoster* viral antigen components. Japanese encephalitis viral antigens include, but are not limited to, antigens such as proteins E, M-E, M-E-NS1, NS1, NS1-NS2A, 80% E, and other Japanese encephalitis viral antigen components. Rabies viral antigens include, but are not limited to, antigens such as rabies glycoprotein, rabies nucleoprotein and other rabies viral antigen components. See Fundamental Virology, Second Edition, eds. Fields, B. N. and Knipe, D. M., 1991, Raven Press, New York, for additional examples of viral antigens.

Bacterial and Other Parasitic Antigens

It is contemplated that suitable bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leishmaniasis, giardiasis (e.g., GenBank Accession No. M33641), amoebiasis, filariasis (e.g., GenBank Accession No. J03266), borreliosis, and trichinosis.

Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components, diptheria bacterial antigens such as diptheria toxin or toxoid and other diptheria bacterial antigen components, tetanus bacterial antigens such as tetanus toxin or toxoid and other tetanus bacterial antigen components, streptococcal bacterial antigens such as M proteins and other streptococcal bacterial antigen components, gram-negative *bacilli* bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components, *Helicobacter pylori* bacterial antigen components, pneumococcal bacterial antigens such as pneumolysin, pneumococcal capsular polysaccharides and other pneumococcal bacterial antigen components, *haemophilus influenza* bacterial antigens such as capsular polysaccharides and other *haemophilus influenza* bacterial antigen components, anthrax bacterial antigens such as anthrax protective antigen and other anthrax bacterial antigen components, rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Fungal antigens which can be used in the compositions and methods of the invention include, but are not limited to, candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fuingal antigens such as trichophytin and other coccidiodes fungal antigen components.

Examples of protozoal and other parasitic antigens include, but are not limited to, *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components, *toxoplasma* antigens such as SAG-1, p30 and other toxoplasmal antigen components, schistosomae antigens such as glutathione-S-transferase, paramyosin, and other schistosomal antigen components, *leishmania major* and other leishmaniae antigens such as gp63, lipophosphoglycan and its associated protein and other leishmanial antigen components, and *trypanosoma cruzi* antigens such as the 75-77 kDa antigen, the 56 kDa antigen and other trypanosomal antigen components.

Cancer Antigens

It is known that tumor-associated antigens are present on tumor cells and that in principle the immune system is able to recognize these antigens and attack the malignant cells (Seliger, et al., 2000, Immunol. Today, 21: 455-64; Gilboa, 1999, Immunity, 11:363-70; Ostrand-Rosenberg, 1994, Cur. Opin. Immunol., 6:722-7). Tumors have, however, developed certain strategies which enable them to escape the immune reaction. For example, this is possible by insufficient presentation of tumor associated antigens and/or insufficient activation of the tumor-specific T cells which are generally present (see e.g., Tortorella et al., 2000, Immunol. Invest., 29: 97-100).

Tumor-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUC1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris, et al., 1986 Mol. Cell. Biol., 6:4650-4656) and is deposited with GenBank under Accession No. M14694. Thus, the present invention can be used as immunotherapeutics for cancers including, but not limited to, cervical, breast, colorectal, prostate, lung cancers, and for melanomas.

Other exemplary cancer antigens include tumor antigens such as those described by P. Boon in "Toward a Genetic Analysis of Tumor Rejection Antigens", 1992, Adv. Cancer Res., 58:177-210. As disclosed in Boon, supra, exemplary tumor antigens (including the respective amino acid sequences for normal and mutated forms of the antigen, respectively) include: P91A isoleucine-serine-threonine-glutamine-asparagine-arginine-arginine-alanine-leucine-aspartic acid-valine-alanine, isoleucine-serine-threonine-glutamine-asparagine-histidine-arginine-alanine-leucine-aspartic acid-valine alanine), P35B (glycine-proline-histidine-serine-serine-asparagine-phenylalanine-glycine-tyrosine, glycine-proline-histidine-serine-asparagine-asparagine-phenylalanine-glycine-tyrosine), P198 (lysine-tyrosine-glutamine-alanine-valine-threonine-alanine-threonine-leucine-glutamic acid-glutamic acid, lysine-tyrosine-glutamine-alanine-valine-threonine-threonine-threonine-leucine-glutamic acid-glutamic acid), and P1A (glutamic acid-isoleucine-leucine-proline-leucine-glycine-tryptophan-leucine-valine-phenylalanine-alanine-valine-valine, glutamic acid-isoleucine-leucine proline-leucine-glycine-tryptophan-leucine-alanine-phenylalanine-alanine-valine-valine).

Self Antigens or Autoantigens

It is also contemplated that antigens useful in the treatment or prevention of autoimmune disorders include, but are not limited to, those derived from nucleosomes for the treatment of systemic lupus erythematosus (e.g., GenBank Accession No. D28394; Bruggen et al., 1996, Ann. Med. Interne (Paris), 147:485-489) and from the 44,000 M(r) peptide component of ocular tissue cross-reactive with *O. volvulus* antigen (McKechnie et al., 1993, Ann Trop. Med. Parasitol., 87:649-652) will also find use in the present invention.

Preferred antigens may be antigens of any of the autoimmune diseases or disorders including, but not limited to, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia greata, allergic responses due to arthropod bite reactions, Crohn's disease, ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

Preferred autoantigens of the present invention include, but are not limited to, at least a portion of a thyroid-stimulating hormone receptor, pancreatic β cell antigens, epidermal cadherin, acetyl choline receptor, platelet antigens, nucleic acids, nucleic acid protein complexes, myelin protein, thyroid antigens, joint antigens, antigens of the nervous system, salivary gland proteins, skin antigens, kidney antigens, heart antigens, lung antigens, eye antigens, erythrocyte antigens, liver antigens and stomach antigens.

Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of antigens involved in graft rejection include antigenic components of the graft to be transplanted into the graft recipient such as heart, lung, liver, pancreas, kidney, and neural graft components.

Toxins as Antigens

Preferred toxins of the present invention include, but are not limited to, staphylococcal enterotoxins, toxic shock syndrome toxin, retroviral antigens, streptococcal antigens, mycoplasma, mycobacterium, and herpes viruses. Retroviral antigens include antigens derived from human immunodeficiency virus. Even more preferred toxins include staphylococcal enterotoxin-A (SEA), staphylococcal enterotoxin-B (SEB), staphylococcal enterotoxin. sub. 1-3 (SE.sub. 1-3), staphylococcal enterotoxin-D (SED), and staphylococcal enterotoxin-E (SEE).

Allergens as Antigens

Preferred allergens of the present invention include, but are not limited to plant pollens, drugs, foods, venoms, insect excretions, molds, animal fluids, and animal hair and dander. Preferred plant pollens include, but are not limited to, ragweed, trees, grass, flowers and ferns. Preferred drugs include, but are not limited to, penicillin, sulfonamides, local anesthetics, salicylates, serum, and vaccines. Preferred foods include, but are not limited to, nuts, seafood, eggs, peas, beans and grain products. Preferred venoms include, but are not limited to, bee venom, wasp venom, ant venom, and snake venom. Preferred insect secretions comprise proteins released by an insect during feeding. Preferred animal excretions include, but are not limited to, urine and saliva.

Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs.

Suitable allergens include, but are not limited to, the major and cryptic epitopes of the Der p I allergen (Hoyne et al., 1994, Immunol., 83190-195), bee venom phospholipase A2 (PLA) (Akdis et al., 1996, J. Clin. Invest., 98:1676-1683), birch pollen allergen Bet v 1 (Bauer et al., 1997, Clin. Exp. Immunol., 107:536-541), and the multi-epitopic recombinant grass allergen rKBG8.3 (Cao et al., 1997, Immunol., 90:46-51).

Preferably the APCs of the invention are modified to express a selected antigen and/or one or more other nucleic acids encoding polypeptides for facilitating antigen presenting to a T cell.

Antigen-Presenting Molecules

One object of the invention is to provide APCs with enhanced specificity for a selected antigen. Another object of the invention is to make APCs with antigen-presenting molecules having determinants which match that of a selected subject or which match any known antigen-presenting molecule determinants. Both MHC/HLA class I and class II molecules may be used.

Class I transplantation antigens of the major histocompatibility complex (MHC) are cell surface glycoproteins which present antigens to cytotoxic T-cells. They are heterodimeric and composed of a polymorphic, MHC-encoded, approximately 45 KD heavy chain, which is non-covalently associated with an approximately 12 KD β-2 microglobulin (β-2m) light chain (Abbas et al., supra).

The extracellular portion of the MHC Class I heavy chain is divided into three domains, $\alpha$-1, $\alpha$-2, and $\alpha$-3, each approximately 90 amino acids long and encoded on separate exons. The $\alpha$-3 domain and β-2m are relatively conserved and show amino-acid sequence homology to immunoglobulin constant domains. The polymorphic $\alpha$-1 and $\alpha$-2 domains show no significant sequence homology to immunoglobulin constant or variable region, but do have weak sequence homology to each other. The membrane-distal polymorphic $\alpha$-1 (approximately 90 amino acids) and $\alpha$-2 (approximately 92 amino acids) domains each include four anti-parallel, β-pleated sheets bordered by one $\alpha$-helical regions, (the first from the $\alpha$-1 and the second from the $\alpha$-2 domain). The $\alpha$-2 domain is attached to the less-polymorphic, membrane-proximal $\alpha$-3 (approximately 92 amino acids) domain which is followed by a conserved transmembrane (25 amino acids) and an intra-cytoplasmic (approximately 30 amino acids) segment. The rat, mouse, and human Class I MHC molecules are believed to have similar structural characteristics based upon known nucleotide sequences of the various MHC Class I molecules.

For a review of the structure and function of the MHC Class I molecules, see, for example: Matsumura et al., 1992, Science, 257:927-934; Bjorkman and Parham, 1990, Annu. Rev. Biochem., 59:253-288; and Germain, 1994, Cell, 76:287-299, all of which incorporated by references.

Exemplary of the mammalian species from which the MHC determinants of the invention can be based are the species identified in Table 1.

TABLE 1

Examples of MHC Nomenclature of Mammalian Species

| Species | MHC designation |
|---|---|
| Chimpanzee | ChLA |
| Dog | DLA |
| Guinea pig | GPLA |
| Human | HLA |
| Mouse | H-2 |
| Pig | SLA |
| Rabbit | RLA |
| Rat | RT1 |
| Rhesus monkey | RhLA |

The classical class I gene family includes the highly polymorphic human class I molecules HLA-A, -B, and -C, and murine class I (i.e., H-2) molecules D, K, and L. A series of structural relatives (non-classical class I molecules) has been found in humans (e.g., HLA-E, -F, -G, -H, -I, and -J; and CD1) and mice (Q, T, M, and CD1) (Shawar et al., 1994, Annu. Rev. Immunol., 12:839-880). These molecules have the typical structure of an antigen-presenting molecule, where a polymorphic heavy chain is noncovalently associated with the conserved β2-M subunit.

In the case of human class I determinants, the determinant can be a polypeptide encoded by any of genetic loci identified in Table 2, as well as polypeptides encoded by genetic loci not listed and/or not yet discovered so long as these can present antigen on the surface of an APC.

TABLE 2

Examples of Human HLA Class I Genetic Loci.

| HLA-A | HLA-B | HLA-C |
|---|---|---|
| A1 | B7 | Cw1[b] |
| A2 | B7 | Cw2 |
| A3 | B13 | Cw3 |
| A11 | B18 | Cw4 |
| A23 | B27 | Cw5 |
| A24 | B35 | Cw6 |
| A25 | B37 | Cw7 |
| A26 | B38 | Cw8 |
| A28 | B39 | |
| A29 | Bw31 | |
| A30 | Bw42 | |
| A31 | B44 | |
| A32 | B45 | |
| AW33 | B49 | |
| | Bw50 | |
| | B51 | |
| | Bw52 | |
| | Bw53 | |
| | Bw54 | |
| | Bw55 | |
| | Bw57 | |
| | Bw58 | |
| | Bw60 | |
| | Bw61 | |
| | Bw62 | |
| | Bw63 | |
| | Bw64 | |
| | Bw65 | |

The "w" designates workshop specificity not yet given accepted status according to WHO nomenclature rules.

The polypeptide employed in this invention can be based on an MHC determinant from a non-human species. Thus, for example, the polypeptide can be encoded by any of the genetic loci described in Table 3, which identify MHC loci of the mouse.

TABLE 3

| MHC Loci in Mouse | | | | | | |
|---|---|---|---|---|---|---|
| Class I Products | II | II | II | II | I | I |
| | K | $A_\beta$ | $A_\alpha$ | $E_\beta$ | $E_\alpha$ | D | L |

The amino acid sequences of mammalian MHC class II alpha and beta chain proteins, as well as nucleic acids encoding these proteins, are also well known in the art and available from numerous sources including GenBank. Exemplary sequences are provided in Auffray et al., 1984, Nature 308 (5957):327-333 (human HLA DQ alpha.); Larhammar et al., 1983, Proc. Natl. Acad. Sci. USA. 80(23):7313-7317 (human LILA DQ beta.); Das et al., 1983, Proc. Natl. Acad. Sci. USA. 80 (12): 3543-3547 (human HLA DR.alpha.); Tonnelle et al., 1985, EMBO J. 4(11):2839-2847 (human HLA DR beta.); Lawrence et al., 1985, Nucleic Acids Res. 13(20):7515-7528 (human HLA DP alpha.); Kelly and Trowsdale, 1985, Nucl. Acids Res. 13(5):1607-1621 (human HLA DP beta); Syha et al., 1989, Nucl. Acids. Res. 17(10):3985 (rat RT.B alpha); Syha-Jedeihauser et al., 1991, Biochim. Biophys. Acta 1089: 414-416 (rat RT1B beta); Benoist et al., 1983, Proc. Natl. Acad. Sci. USA 80(2): 534-538 (mouse I-A alpha.); and Estess et al., 1986, Proc. Natl. Acad. Sci. USA 83(11):3594-3598 (mouse I-A beta.).

It will be understood that the invention encompasses equivalent determinants having substantially the same structural properties (e.g., have at least 50% or 60% or 70% or 80% or 90% or more sequence identity to the determinants encoded by genetic loci of Table 2 and Table 3). Thus, this invention is intended to cover variants of MHC determinants (e.g., as described in U.S. Pat. No. 6,153,408, thereby incorporated by reference).

Other Molecules Involved in MHC Class I Antigen-Presenting Pathway

Also encompassed in the invention are modified APCs comprising other immunoregulatory molecules that act to enhance the function of APCs including but not limited to transporters, proteases, costimulatory molecules, adhesion molecules, cytokines and chemokines, etc.

For example, the ABC transporter proteins, human TAP1 and TAP2, have been cloned as disclosed in Trowsdale et al., 1990, Nature, 348:741; and Powis et al., 1993, Immunogenetics, 37:373.

The presentation of antigen via the MHC class I pathway is mediated by several MHC class I pathway-associated proteins in addition to the TAP proteins. For example, the low molecular weight proteins LMP 2 and LMP 7 serve as subunits of the proteasome, a multicatalytic proteinase complex that is thought to degrade cellular proteins in order to generate the peptides that associate with MHC class I molecules. Once generated, the peptides associate with heat shock proteins ("HSPs"; e.g., gp 96, HSP 90, and HSP 70), which act as chaperones to help transport the peptides from proteasomes to the nascent MHC molecules.

Another group of useful nucleic acids which may be introduced into modified APCs include DNA sequences encoding costimulatory molecules, accessory molecules, and adhesion molecules, which are known and include, but are not limited to, B7-1 (Freeman et al., 1989, J. Immunol., 143:2714-2722); B7-2 (Azuma et al., 1993, Nature, 366:76-79) and B7-3 molecules; CD83 (Lohmann et al., 2000, Cancer Gene Ther., 7:

605-14; Zhou et al., 1995, J. Immunol., 154: 3821-35); 4.1 BB ligand (Goodwin et al., 1993, European J. Immunol., 23:2631; Alderson et al., 1994, Eur. J. Immunol., 24:2219); ICAM-1 (Simmons et al., 1988, Nature, 331:624-627; Swain, 1995, Immunol., 155:45; Damle, 1993, J. Immunol., 151: 2368); ICAM-2 (Springer, 1994, Cell, 76: 301-314; Dustin et al., 1999, in Guidebook to the Extracellular Matrix and Adhesion Proteins, eds. Kreis and Vale, Sambrook and Tooze, New York); ICAM-3 (Fawcett et al., 1992, Nature, 360: 481-4); LFA-3 (Wallner et al., 1987, Exp. Med., 166:923-932); Seed et al., 1987, Nature, 329:840-842), CD72 (NIH Genbank, Yng et al., 1995, J. Immunol., 154:2743; and see Molecular Immunology, 2nd edition, ed. Hames and Glover, IRL Press, New York, p. 263)); CD40 (Shamadzu et al., 1995, Biochim. Biophys. Acta, 126:67-72) and heat-stable antigen (hsa) (Liu, 1992, J. Exp. Med., 175:437-445).

Still other nucleic acids useful include DNA sequences encoding lymphokines including, but not limited to, interleukins, interferons and GM-CSF (Ladner et al., 1987, EMBO J., 6:2693-98); TNF (Shirai et al., Nature, 313:803-806; and Wang, 1985, Science, 228:149-154). Interleukins include, for example, IL-2 (Taniguchi et al., 1983, Nature, 302:305; Devos et al., 1983, Nucl. Acid. Res., 11:4307-23), IL-1 (Gubler et al., 1986, J. Immunol., 136:2492-97); Bensi et al., 1987, Gene, 52:95-101 and Nishida et al., 1987, Biochem. Biophys. Res. Comm., 143:345-352) and IL-12 (Wolf et al., 1991, J. Immunol., 146:3074-3081). Interferons ("IFN") include IFNα (Streuli et al., 1980, Science, 209:1343-47 and Henco et al, 1985, J. Mol. Biol., 185:227-260), IFNβ (Goeddel et al., 1980, Nucl. Acid. Res., 8:57-74) and IFNγ (Nishi et al., 1985, J. Biochem., 97:153-159; Gray and Goeddel, 1982, Nature, 298:859-863).

Coding sequences of these and other lymphokines can be found in the EMBL and NIH Genbank databases and See Webb and Goeddel, eds., 1982, Lymphokines, Vol. 13: Molecular Cloning and Analysis of Lymphokines, Academic Press, New York.

Additional useful nucleic acids include DNA sequences encoding chemokines such as MCP-1 (Yoshimura, et. al., 1989, FEBS Lett., 244 487-93; Rollins, et. al., 1989, Mol. Cell Biol., 9 4687-95) and RANTES (Schall, et. al., 1988, J. Immunol., 141 1018-25, and Nelson, et. al., 1993, J. Immunol., 151 2601-12) and others, which are published and are found in the EMBL and NIH Genbank databases.

Desired genes can be introduced into expression vectors and include those encoding selected antigens, selected class I and class II HLA molecules, costimulatory and other immunoregulatory molecules, adhesion molecules, ABC transporter proteins, including the TAP1 and TAP2 proteins, and any other molecules as described above, along with appropriate regulatory elements to drive expression of the recombinant coding sequences within recipient subject cells. Various combinations of coding sequences may be inserted in a suitable expression vector or vectors.

Sequences encoding molecules useful in the invention will include at least a portion of the coding sequence of the useful molecules sufficient to provide the engineered cell with the desired antigen presenting function. For example, in the case of a costimulatory molecule, a portion of the coding sequence that enables it to bind its ligand on T cells can be used (e.g., as described in Linsley et al., 1990, Proc. Natl. Acad. Sci. USA, 87:5031-5035). Sufficient portions of the coding sequences of other useful molecules and methods for determining them are known in the art (e.g., as described in references cited above).

Heterologous Polypeptides

An important aspect of the invention is the use of a heterologous polypeptide fused to the N-terminus of the antigen. The heterologous fusion polypeptide aids in the efficient presentation of the antigen at the cell surface in association with a class I molecule. Without wishing to be bound by any single mechanism, the antigen, in the context of the heterologous fusion polypeptide (i.e., fusion of the N-terminus of the antigen to the C-terminus of the heterologous polypeptide) can be processed by proteasomes, or can be presented at the cell surface via proteasome-independent processing reactions. It is possible that the heterologous polypeptide is processed by proteasomes but that the fused antigen itself escapes the proteasome. Alternatively, the proteasome may be involved in processing the antigen sequence itself.

In one aspect, the heterologous polypeptide is a reporter molecule for facilitating the selection and isolation of more effective APCs (e.g., such as APCs which highly express an antigen) from a population of modified cells.

According to one aspect of the invention, a nucleic acid encoding a reporter molecule (e.g. a reporter mRNA or a reporter polypeptide) may be fused to one or more of the useful nucleic acids as described above to create a fusion protein. Preferably, a nucleic acid encoding a reporter molecule is fused in frame with a selected useful nucleic acid. More preferably, a nucleic acid encoding a reporter molecule is fused with a selected antigen and/or a selected antigen-presenting molecule (e.g., MHC/HLA) determinant. When two or more nucleic acids used to construct an APC are fused with nucleic acids encoding reporter molecules, it is preferred that the reporter molecules selected generate distinct detectable signals.

In a preferred embodiment, a nucleic acid encoding a heterologous polypeptide is fused to a nucleic acid encoding an antigenic peptide through an intervening linker sequence. Preferably, the translated fusion protein (i.e., the antigen-linker-heterologous polypeptide fusion) comprises a C-terminus which corresponds to the C-terminus of the antigenic peptide (e.g., the C-terminus of the minimal antigen sequence that is necessary to bind to an antigen-presenting molecule such as a class I or class II molecule, and stimulate an immune response). A natural cell-associated protease can be used to cleave the antigenic peptide from the heterologous polypeptide at the linker sequence; however, in some aspects of the invention, nucleic acids encoding cell-associated proteases are introduced into the cell. The liberated peptide fragment then binds antigen-presenting molecules such as MHC molecules and is presented on the cell surface. This strategy engineers cells to efficiently present a specific antigenic peptide.

Preferably, the linker polypeptide comprises a protease cleavage site comprising a peptide bond which is hydrolyzable by a protease. The linker can comprise one or more additional amino acids on either side of the bond to which the catalytic site of the protease also binds (see, e.g., Schecter and Berger, 1967, Biochem. Biophys. Res. Commun. 27, 157-62). Alternatively, the cleavage site of the linker can be separate from the recognition site of the protease and the two cleavage site and recognition site can be separated by one or more (e.g., two to four) amino acids. In one aspect, the linker comprises at least 2, 3, 4, 5, 6, 7, 8, 9, 10, 20, 30, 40, 50 or more amino acids. More preferably the linker is between 5 and 25 amino acids in length, and most preferably, the linker is between 8 and 15 amino acids in length.

Some proteases useful according to the invention are discussed in the following references: V. Y. H. Hook, *Proteolytic and cellular mechanisms in prohormone and proprotein pro-* cessing, RG Landes Company, Austin, Tex., USA (1998); N. M. Hooper et al., 1997, Biochem. J. 321:265-279; Werb, 1997, Cell 91: 439-442; Wolfsberg et al., 1995, J. Cell Biol. 131: 275-278; Murakami and Etlinger, 1987, Biochem. Biophys. Res. Comm. 146: 1249-1259; Berg et al., 1995, Biochem. J. 307: 313-326; Smyth and Trapani, 1995, Immunology Today 16: 202-206; Talanian et al., 1997, J. Biol. Chem. 272: 9677-9682; and Thomberry et al., 1997, J. Biol. Chem. 272: 17907-17911. Suitable proteases include, but are not limited to, those listed in Table 4 below.

TABLE 4

Proteases and Their Cleavage Signals

| Protease | Cleavage Signal (Exemplary Linker Nucleic Acid Sequence) |
|---|---|
| subtilisin/kexin family (furin, PC1, PC2, PC4, PACE4, PC5, PC) | RXKR (SEQ ID NO: 8) (CGC XXX AAG CGC) (SEQ ID NO: 9) |
| MMP-2 | PLGLWA (SEQ ID NO: 10) (CCC CTG GGC CTG TGG GCC) (SEQ ID NO: 11) |
| MT1-MMP | PLGLWA (SEQ ID NO: 10) (CCC CTG GGC CTG TGG GCC) (SEQ ID NO: 11) |

| Protease | Cleavage Signal-Amino Acid Sequence (Exemplary Linker Nucleic Acid Sequence) |
|---|---|
| caspase-1 | YEVDGW (SEQ ID NO: 12) (TAC GAG GTG GAC GGC TGG) (SEQ ID NO: 13) |
| caspase-2 | VDVADGW (SEQ ID NO: 14) (GTG GAC GTG GCC GAC GGC TGG) (SEQ ID NO: 15) |
| caspase-3 | VDQMDGW (SEQ ID NO: 16) (GTG GAC CAG ATG GAC GGC TGG) (SEQ ID NO: 17) |
| caspase-4 | LEVDGW (SEQ ID NO: 18) (CTG GAG GTG GAC GGC TGG) (SEQ ID NO: 19) |
| caspase-6 | VQVDGW (SEQ ID NO: 20) (GTG CAG GTG GAC GGC TGG) (SEQ ID NO: 21) |
| caspase-7 | VDQVDGW (SEQ ID NO: 22) (GTG GAC CAG GTG GAC GGC TGG) (SEQ ID NO: 23) |
| caspase-8 | DXXD (SEQ ID NO: 24) (GAC XXX XXX GAC) (SEQ ID NO: 25) |
| caspase-9 | DXXD (SEQ ID NO: 24) (GAC XXX XXX GAC) (SEQ ID NO: 25) |
| alpha-secretase | amyloid precursor protein (APP) |
| proprotein convertase (subtilisin/kexin isozyme SKI-1) | RGLT (SEQ ID NO: 26) (CGC GGC CTG ACC) (SEQ ID NO: 27) |
| proprotein convertases | cleavage at hydrophobic residues (e.g., Leu, Phe, Val, or Met) or at small amino acid residues such as Ala or Thr |
| foot and mouth disease virus, protease 2A | NFDLLKLAGDVESNPGP (SEQ ID NO: 28) (AAC TTC GAC CTG CTG AAG CTG GCC GGC GAC GTG GAG AGC AAC CCC GGC CCC) (SEQ ID NO: 29) |
| signal peptidase | A-X-A-X (SEQ ID NO: 30) (GCC XXX GCC XXX) (SEQ ID NO: 31) |
| aminopeptiases (e.g., arginine aminopeptidase, lysine aminopeptidase, aminopeptidase B, trypsin) | LTK (CTG ACC AAG) |
| insulin degrading enzyme | GGFLRKVGQ (SEQ ID NO: 32) (GGC GGC TTC CTG CGC AAG GTG GGC CAG) (SEQ ID NO: 33) |

Additional linker polypeptides can be obtained from the substrates for proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); prolyl endopeptidase; and high molecular weight protease.

Cell surface proteases also can be used with cleavable linkers according to the invention and include, but are not limited to: Aminopeptidase N; Puromycin sensitive aminopeptidase; Angiotensin converting enzyme; Pyroglutamyl peptidase II; Dipeptidyl peptidase IV; N-arginine dibasic convertase; Endopeptidase 24.15; Endopeptidase 24.16; Amyloid precursor protein secretases alpha, beta and gamma; Angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; Urokinase plasminogen activator; Tissue plasminogen activator; Plasmin; Thrombin; BMP-1 (procollagen C-peptidase); ADAM 1, 2, 3, 4, 5, 6, 7, 8, 9, 10, and 11; and, Granzymes A, B, C, D, E, F, G, and H.

An alternative to relying on cell-associated proteases is to use a sequence encoding a self-cleaving linker. In one embodiment of the invention, the foot and mouth disease virus (FMDV) 2A protease is used as a linker. This is a short polypeptide of 17 amino acids that cleaves the polyprotein of FMDV at the 2A/2B junction. The sequence of the FMDV 2A propeptide is NFDLLKLAGDVESNPGP (SEQ ID NO: 24). Cleavage occurs at the C-terminus of the peptide at the final glycine-proline amino acid pair and is independent of the presence of other FMDV sequences and cleaves even in the presence of heterologous sequences.

Insertion of this sequence between two protein coding regions (i.e., between the antigen and the heterologous protein portion of a fusion protein according to the invention) results in the formation of a self-cleaving chimera which cleaves itself into a C-terminal fragment which carries the C-terminal proline of the 2A protease on its N-terminal end, and an N-terminal fragment that carries the rest of the 2A protease peptide on its C-terminus (see, e.g., P. deFelipe et al., Gene Therapy 6: 198-208 (1999)). Thus, instead of using a cleavage signal recognizable by a cell-associated protease, in this embodiment, the self-cleaving FMDV 2A protease sequence links the heterologous marker polypeptide to the antigen resulting in spontaneous release of the heterologous polypeptide from the antigen. Self-cleaving linkers and additional protease-linker combinations are described further in WO 0120989, the entirety of which is incorporated by reference herein.

Nucleic acids encoding linker sequences described above can be cloned from sequences encoding the natural substrates of an appropriate protease or can be chemically synthesized using methods routine in the art. The codons selected for such nucleic acids preferably those which are most frequently used in humans, such as those listed in Table 5 below. The exemplary nucleic acid sequences shown in Table 4 rely on codons which are most frequently used in humans.

TABLE 5

Preferred DNA Codons For Human Use

| Amino Acids | 3 Letter Code | 1 Letter Code | Codons Preferred in Human Genes |
|---|---|---|---|
| Alanine | Ala | A | GCC |
|  |  |  | GCT |
|  |  |  | GCA |
|  |  |  | GCG |

TABLE 5-continued

Preferred DNA Codons For Human Use

| Amino Acids | 3 Letter Code | 1 Letter Code | Codons Preferred in Human Genes |
|---|---|---|---|
| Cysteine | Cys | C | TGT |
| | | | TGT |
| Aspartic Acid | Asp | D | GAC |
| | | | GAT |
| Glutamic Acid | Glu | E | GAG |
| | | | GAA |
| Phenylalanine | Phe | F | TTC |
| | | | TTT |
| Glycine | Gly | G | GGC |
| | | | GGG |
| | | | GGA |
| | | | GGT |
| Histidine | His | H | CAC |
| | | | CAT |
| Isoleucine | Ile | I | ATC |
| | | | ATT |
| | | | ATA |
| Lysine | Lys | K | AAG |
| | | | AAA |
| Leucine | Leu | L | CTG |
| | | | TTG |
| | | | CTT |
| | | | CTA |
| | | | TTA |
| Methionine | Met | M | ATG |
| Asparagine | Asn | N | AAC |
| | | | AAT |
| Proline | Pro | P | CCC |
| | | | CCT |
| | | | CCA |
| | | | CCG |
| Glutamine | Gln | Q | CAG |
| | | | CAA |
| Arginine | Arg | R | CGC |
| | | | AGG |
| | | | CGG |
| | | | AGA |
| | | | CGA |
| | | | CGT |
| Serine | Ser | S | AGC |
| | | | TCC |
| | | | TCT |
| | | | AGT |
| | | | TCA |
| | | | TCG |
| Threonine | Thr | T | ACC |
| | | | ACA |
| | | | ACT |
| | | | ACG |
| Valine | Val | V | GTG |
| | | | GTC |
| | | | GTT |
| | | | GTA |
| Tryprophan | Trp | W | TGG |
| Tyrosine | Tyr | Y | TAC |
| | | | TAT |

The uppermost codons represent those most preferred for use in human genes. Underlined codons are almost never used in human genes and are therefore not preferred.

Cells expressing fusion proteins according to the invention can be detected and selected for in a variety of ways. In one aspect, the heterologous polypeptide is a reporter polypeptide detectable within the cell before and/or after cleavage of the heterologous polypeptide from the antigen. As described above, preferably, the reporter polypeptide used in the invention is an autofluorescent protein (e.g., GFP, EGFP). Autofluorescent proteins provide a ready assay for identification of expression of a nucleic acid of interest. Because the activity of the polypeptide (and by inference its expression level) can be monitored quantitatively using a flow sorter, it is simple to assay many independent transfectants either sequentially or in bulk population. The best APCs can then be screened for or selected from the population based on the expression levels of the critical molecules. Quantitative parameters such as mean fluorescence intensity and variance can be determined from the fluorescence intensity profile of the cell population (Shapiro, H., 1995, Practical Flow Cytometry, 217-228).

A flow sorter can be used not only as a screen to examine the expression of nucleic acid of interest in transfected cells, but also as a tool to manipulate and bias the cell populations in potentially useful ways. For example, in certain cases it may be helpful to select cells expressing high level of a first nucleic acid, in other cases it may be helpful to select cells expressing high level of a second nucleic acid, but low level of the first nucleic acid. Alternatively, it may be desirable simply to exclude cells that do not express a nucleic acid at a desired level above the background. The flow sorter permits such selections to be carried out with extraordinary efficiency because cells can be sorted at a rate of ten to one hundred million per hour (Shapiro H., 1995, In *Practical Flow Cytometry*, 217-228).

In some aspects, when there are two or more nucleic acids used to transfect cells (e.g., antigen encoding nucleic acid molecules and nucleic acid encoding antigen-presenting molecules or immunomodulatory molecules), it is preferred that a reporter molecule fused to each nucleic acid generates different detectable signals so the expression of each nucleic acid may be distinguished.

In another aspect, the heterologous polypeptide can provide a function to the cell which can be selected for, e.g., such as the ability to survive in a selection medium. Survival can conferred by providing a heterologous polypeptide which confers antibiotic resistance or which can render a toxic agent in a medium non-toxic to a cell in which it is expressed.

In a further aspect, the heterologous polypeptide is bindable to an antibody which can be used to identify, sort, and purify cells containing the heterologous polypeptide. For example, the heterologous polypeptide can be a cell surface polypeptide which can be expressed on the cell surface independently of the antigen. Expression of the heterologous polypeptide can be confirmed by an immunoassay such as an ELISA (enzyme-linked immunoabsorbent assay) (see e.g., U.S. Pat. No. 5,962,320; U.S. Pat. No. 6,187,307; U.S. Pat. No. 6,194,205), by FACS (Fluorescent Activated Cell Sorting), or by other methods routine in the art, and cells expressing the heterologous polypeptide can be isolated from other cells to obtain substantially pure cell populations.

As described above, in one embodiment, constructs encoding fusion proteins are generated which include a linker polypeptide sequence between a nucleic acid encoding the heterologous polypeptide and the nucleic acid encoding an antigen. The linker sequence preferably maintains the correct reading frame of the selected antigen and does not interfere with its function (e.g., allows the antigen to be presented by the antigen-presenting molecule). In one aspect, the construct comprises a nucleic acid sequence encoding more than one antigen.

In another embodiment, a nucleic acid encoding a heterologous polypeptide is fused to a nucleic acid encoding an antigenic peptide/polypeptide without an intervening linker sequence to liberate the antigenic peptide/polypeptide sequence from the reporter polypeptide sequence (i.e., no protease cleavage site is inserted between the antigenic peptide/polypeptide sequence and the reporter polypeptide sequence).

The presence of the heterologous polypeptide can be detected by detecting the transcript of the fusion protein (e.g., by hybridization analysis), by measuring the activity of the polypeptide, or by detecting the polypeptide itself (i.e., in an immunoassay such as a Western or Eliza). In one aspect, the heterologous polypeptide is a reporter polypeptide which produces a detectable signal when it is expressed in the cell. Reporter polypeptides should not be endogenous to the subject cell, or at least should not be detectable in the subject cell in an amount that renders detection of its detection over an endogenous product impossible. Non-limiting examples of reporter molecules useful in the invention include luciferase (from firefly or other species), chloramphenicol acetyltransferase, P-galactosidase, green fluorescent protein (GFP), enhanced green fluorescent protein (EGFP), and dsRed. In order to be useful according to the invention, the background expression of a nucleic acid encoding a reporter molecule (i.e., the detectable expression of the reporter polypeptide in the absence of a signal that activates the regulatory pathway to which the reporter polypeptide is responsive) must be low. Reporter molecule background may be said to be low if an induction of 5 fold, or 10-fold, preferably 20 fold, 30 fold, or up to 50 to 100 fold or more is detectable within the linear range of the detection assay.

In a preferred embodiment, a nucleic acid encoding EGFP reporter polypeptide (Clontech, Palo Alto, Calif.) is fused to a nucleic acid encoding an antigenic peptide.

In a more preferred embodiment, the nucleic acid encoding EGFP reporter polypeptide or a functional portion thereof is fused to the N-terminal of the nucleic acid encoding the antigenic peptide.

In another embodiment, dsRed2 is used as the reporter polypeptide.

In still another embodiment, the heterologous polypeptide is a polypeptide which allows a cell to survive in a particular selection medium. For example, the heterologous polypeptide can comprise an antibiotic resistance gene or an enzyme which catalyzes the conversion of a toxic product to a non-toxic product. In this way the heterologous polypeptide allows cells which comprises the antigen: heterologous polypeptide fusion proteins to be identified by virtue of their survival in selection medium.

In a further aspect, the heterologous polypeptide is bindable to a binding partner such as an antibody and can be used to select cells expressing the antigen:heterologous polypeptide fusion using standard affinity-based purification techniques (e.g., flow sorting, magnetic sorting, panning, affinity column purification, and the like). Such techniques are routine in the art. Preferably, the heterologous polypeptide is a cell surface molecule In one aspect, cells comprising cell surface molecule:antigen fusions are sorted by flow sorting.

However, there is no requirement that the heterologous polypeptide be a detectable molecule such as a reporter polypeptide or a molecule which confers survival in selection medium (e.g., a polypeptide encoded by a selection marker gene) so long as the polypeptide minimally serves the function of effecting the efficient presentation of the antigen at the cell surface in association with a class I molecule. In this aspect, cells comprising the fusion can be selected by identifying cells which are capable of acting as professional APCs, i.e., generating an antigen-specific immune response. With regard to the structure of the heterologous polypeptide necessary for it to aid in the efficient presentation of antigen, rather than a single type of structure conferring the property of efficient presentation, any number of polypeptide sequences or structures can serve the purpose, but an important element of the structure is that the fusion polypeptide be fused to the N-terminus of the antigen, either directly or via a linker. That is, it is important that the fusion be between the C-terminus of the heterologous polypeptide and the N-terminus of the antigen or between the C-terminus of the heterologous polypeptide and the N terminus of the linker (which is joined at its C-terminus to the antigen).

In one aspect, a population of cells is identified which comprises at least one modified APC and which mediates a desired level of an immune response (e.g., 10% more killing or at least two-fold more killing than a control cell population). The population of cells can comprise one or more cells which do not express the nucleic acid encoding the antigen: heterologous polypeptide fusion, although preferably, at least 50% of cells in the population do express the fusion. In one aspect, nucleic acids encoding the antigen-heterologous polypeptide fusion proteins can be introduced into the cell by exposing the cell to a high number of viral particles comprising the nucleic acids so as to generate populations wherein at least 50% of the cells express the fusion protein and can serve as professional APCs.

Expression Vectors

Techniques for nucleic acid manipulation are well known. (See, e.g., Sambrook et al., 1989; Ausubel et al. 1987 and in Annual Reviews of Biochemistry, 1992, 61:131-156). Reagents useful in applying such techniques, such as restriction enzymes and the like, are widely known in the art and commercially available from a number of vendors.

Nucleic acid sequences for use in the present invention may also be produced in part or in total by chemical synthesis, e.g. by the phosphoramidite method described by Beaucage, et al., 1981, Tetra. Letts., 22:1859-1862, or the triester method (Matteucci et al., 1981, J. Am. Chem. Soc., 103: 3185), which may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

Natural or synthetic nucleic acid fragments coding for a desired sequence may be incorporated into vectors capable of introduction into and replication in a prokaryotic or eukaryotic cell. Usually the vectors are suitable for replication in a unicellular subject, such as cultured mammalian or other animal cell lines, with and without integration within the genome.

Useful nucleic acid molecules for constructing the APCs of the present invention (e.g., selected antigens, MHC molecules, adhesion molecules, costimulatory molecules, etc.) may be cloned into a vector before they are introduced into an appropriate cell and may be passage in cells other than APCs to generate useable quantities of these nucleic acids.

Suitable vectors for the invention may be plasmid or viral vectors, including baculoviruses, adenoviruses, poxviruses, adenoassociated viruses (AAV), and retrovirus vectors (Price et al, 1987, Proc. Natl. Acad. Sci. USA, 84:156-160) such as the MMLV based replication incompetent vector pMV-7 (Kirschmeier et al., 1988, DNA, 7:219-225), as well as human and yeast modified chromosomes (HACs and YACs). Plasmid expression vectors include plasmids including pBR322, pUC or Bluescript.™. (Stratagene, San Diego, Calif.).

The expression vectors may comprise one or more regulatory elements to drive and/or enhance expression of upstream or downstream nucleic acids. These regulatory sequences are selected on the basis of the cells (e.g., types of APCs) to be used for expression, and are operatively linked to a nucleic acid sequence to be expressed. The term "regulatory elements" is intended to include promoters, enhancers and other expression control elements (e.g., polyadenylation signals). Such regulatory elements are described, for example, in Goeddel; 1990, *Gene Expression Technology: Methods in Enzymology* 185, Academic Press, San Diego, Calif.

Regulatory elements include those which direct expression of a nucleotide sequence in many types of subject cells as well as those which direct expression of the nucleotide sequence only in certain subject cells (e.g., tissue-specific regulatory sequences).

Regulatory elements also include those which direct constitutive expression of an operatively linked nucleic acid sequence and those which direct inducible expression of the nucleic acid sequence. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad range of cells in which they can activate and/or modulate transcription while others are functional only in a limited subset of cell types (See e.g., Voss et al., 1986, Trends Biochem. Sci., 11:287; and Maniatis et al., supra, for reviews). For example, the SV40 early gene enhancer is very active in a wide variety of cell types from many mammalian species and has been widely used for the expression of proteins in mammalian cells (Dijkema et al., 1985, EMBO J. 4:761). Two other examples of promoter/enhancer elements active in a broad range of mammalian cell types are those from the human elongation factor 1α gene (Uetsuki et al., 1989, J. Biol. Chem., 264:5791; Kim et al., 1990, Gene, 91:217; and Mizushima, et al., 1990, Nagata, Nuc. Acids. Res., 18:5322) and the long terminal repeats of the Rous sarcoma virus (Gorman et al., 1982, Proc. Natl. Acad. Sci. USA, 79:6777) and the human cytomegalovirus (Boshart et al., 1985, Cell, 41:521).

Suitable promoters which may be employed include, but are not limited to, TRAP promoters, adenoviral promoters, such as the adenoviral major late promoter; the cytomegalovirus (CMV) promoter; the respiratory syncytial virus (RSV) promoter; inducible promoters, such as the MMT promoter, the metallothionein promoter, heat shock promoters; the albumin promoter; the ApoAI promoter; human globin promoters; viral thymidine kinase promoters, such as the Herpes Simplex thymidine kinase promoter; retroviral LTRs; ITRs; the β-actin promoter; and human growth hormone promoters. The promoter also may be the native promoter that controls the nucleic acid encoding the polypeptide and the sequences of native promoters may be found in the art (see Agrawal et al., 2000, J. Hematother. Stem Cell Res., 795-812; Cournoyer et al., 1993, Annu. Rev. Immunol., 11:297-329; van de Stolpe et al., 1996, J. Mol. Med., 74:13-33; Herrmann, 1995, J. Mol. Med., 73:157-63)

A variety of enhancer sequences can be used in the instant invention including but not limited to: Immunoglobulin Heavy Chain enhancer; Immunoglobulin Light Chain enhancer; T-Cell Receptor enhancer; HLA DQ α and DQ β enhancers; β-Interferon enhancer; interleukin-2 enhancer; Interleukin-2 Receptor enhancer; MHC Class II $5_4^k$ enhancer; MHC Class II HLA-DRα enhancer; β-Actin enhancer; Muscle Creatine Kinase enhancer; Prealbumin (Transthyretin) enhancer; Elastase I enhancer; Metallothionein enhancer; Collagenase enhancer; Albumin Gene enhancer; α-Fetoprotein enhancer; β-Globin enhancer; c-fos enhancer; c-HA-ras enhancer; Insulin enhancer; Neural Cell Adhesion Molecule (NCAM) enhancer; $α_1$-Antitrypsin enhancer; H2B (TH2B) Histone enhancer; Mouse or Type I Collagen enhancer; Glucose-Regulated Proteins (GRP94 and GRP78) enhancer; Rat Growth Hormone enhancer; Human Serum Amyloid A (SAA) enhancer; Troponin I (TN I) enhancer; Platelet-Derived Growth Factor enhancer; Duchenne Muscular Dystrophy enhancer; SV40 Polyoma enhancer; Retrovirusal enhancer; Papilloma Virus enhancer; Hepatitis B Virus enhancer; Human Immunodeficiency enhancer; Cytomegalovirus enhancer; and Gibbon Ape Leukemia Virus enhancer.

Exemplary inducible promoter/enhancer sequences and their inducers are listed below.

TABLE 6

Useful Inducible Promoters/Enhancers

| Element | Inducer |
|---|---|
| MTII | PhorbolEster(TFA) |
|  | Heavymetals |
| MMTV (mouse mammary tumor virus) | Glucocorticoids |
| β-Interferon | poly(rI) X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TFA) |
| Murine MX Gene | Interferon, Newcastle Disease Virus |
| GRP78 Gene | A23187 |
| α-2-Macroglobulin | IL-6 |
| Vimentin | Serum |
| MHC ClassI Gene H-2kB | Interferon |
| HSP70 | Ela, SV40 Large T Antigen |
| Proliferin | Phorbol Ester (TPA) |
| Tumor Necrosis Factor | FMA |
| Thyroid Stimulating Hormone α Gene | Thyroid Hormone |

Additional regulatory sequences may be obtained from the Eukaryotic Promoter Data Base EPDB) also can be used to drive expression of a nucleic acid.

In certain embodiments of the invention, the delivery of a vector in a cell may be identified in vitro or in vivo by including a selection marker in the expression construct. The marker would result in an identifiable change to the modified cell permitting easy identification of expression. Usually the inclusion of a drug selection marker aids in cloning and in the selection of transformants. Genes which can be used as selectable markers are known in the art and include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene.

Alternatively, genes encoding enzymes, such as herpes simplex virus thymidine kinase (tk) (eukaryotic) or chloramphenicol acetyltransferase (CAT) (prokaryotic) may be employed to provide selectable markers. Immunologic markers also can be employed. The exact type selectable marker employed is not believed to be important, so long as it is capable of being expressed simultaneously with the nucleic acid encoding a polypeptide of interest. Further examples of selectable markers are well known to one of skill in the art.

Where a cDNA insert is employed, e.g., to express class I molecules, costimulatory molecules, adhesion molecules, cytokines, and other molecules as described above, one typically will desire to include a polyadenylation signal to effect proper polyadenylation of the nucleic acid transcript. The nature of the polyadenylation signal is not believed to be crucial to the successful practice of the invention, and any such sequence may be employed. These elements can serve to enhance message levels and to minimize read through from the expression cassette into other sequences.

Constructing Modified APCs

In accordance with the invention, the modified APCs expressing one or more selected antigens and expressing additional selected molecules, including immunoregulatory molecules, are produced ex vivo by the insertion of one or more recombinant or synthetic nucleic acid sequences (genes) encoding these molecules, such that the molecules are expressed in effective amounts in the recipient subject cell. By "effective amount" is meant that expression is sufficient to enable the recipient cell to provoke the desired immune response in vivo where the immune response stimulated or suppressed by the APCs is at least 20%, 40%, 60%, 80% or 100% or greater, when compared to the immune response stimulated or suppressed by the unmodified cells used to make the APCs. Assays for measuring an immune response (e.g., CTL assay, Cell proliferation assay) are well known in the art, for example, can be found in Coligan et al., 1994, supra, incorporated by reference.

Nucleic acid sequences encoding selected antigens, ABC transporter proteins, immunoregulatory molecules including costimulatory molecules, lymphokines, and chemokines, and/or the functional domains of these molecules, are described above and are known, and/or obtainable using methods known in the art. The nucleic acid sequences can be cloned into one or more expression vectors as described above or according to other methods known in the art.

The expression construct(s) must be introduced into a cell in order to generate the modified APCs of the invention. This delivery may be accomplished in vitro, such as by transfecting or transforming cells.

Several non-viral methods for the transfer of expression constructs into cultured mammalian cells also are contemplated by the present invention. These include calcium phosphate precipitation (Graham, et al., 1973; Chen, et al., 1987; Rippe, et al., 1990) DEAE-dextran (Gopal, 1985), electroporation (Tur-Kaspa et al., 1986; Potter et al., 1984), direct microinjection (Harland, et al., 1985), DNA-loaded liposomes (Nicolau, et al., 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu, et al., 1987; Wu, et al., 1988). Some of these techniques may be successfully adapted for in vivo or ex vivo use.

Once the expression construct has been delivered into the cell, the nucleic acid encoding a polypeptide of interest may be positioned and expressed at different sites. In certain embodiments, the nucleic acid encoding a polypeptide may be stably integrated into the genome of the cell. This integration may be via homologous recombination (gene replacement) or it may be integrated in a random, non-specific location (gene augmentation), see Holmes-Son et al., 2001, Adv. Genet. 43: 33-69. In yet further embodiments, the nucleic acid may be stably maintained in the cell as a separate, episomal segment of DNA. Such nucleic acid segments or "episomes" encode sequences sufficient to permit maintenance and replication independent of or in synchronization with the subject cell cycle. How the expression construct is delivered to a cell and where in the cell the nucleic acid remains is well known in the art and is dependent on the type of expression construct employed.

Preparing Cells for Nucleic Acid Transfer

Cell cultures may be prepared in various ways for gene transfer in vitro. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

During in vitro culture conditions the expression construct may express a nucleic acid encoding a selected polypeptide in the cells. The primary cells modified as APCs may be reintroduced into the original animal, or administered into a different animal, in a pharmaceutically acceptable form by any of the means described below. Thus, providing an ex vivo method of treating a mammal with a pathologic condition is within the scope of the invention.

Introduction of Naked Nucleic Acid into Cells In Vitro or Ex Vivo

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well.

Transfection Mediated by $CaPO_4$

Naked nucleic acid can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in *Current Protocols in Molecular Biology*, Ausubel, F. M. et al. (eds.), 1989, Greene Publishing Associates, Section 9.1 and in *Molecular Cloning: A Laboratory Manual, 2nd Edition*, Sambrook et al., 1989, Cold Spring Harbor Laboratory Press, Sections 16.32-16.40 or other standard laboratory manuals.

Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. Thus nucleic acids encoding a polypeptide of interest may also be transferred in a similar manner in vivo to express on polypeptides described above.

Transfection Mediated by DEAE-Dextran

Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce nucleic acid transiently into cells but is not preferred for creating stably transfected cells. Thus, this method can be used for short term production of a gene product but is not a method of choice for long-term production of a gene product. Protocols for DEAE-dextran-mediated transfection can be found in *Current Protocols in Molecular Biology*, Ausubel, F. M. et al. (eds.), 1989, Greene Publishing Associates, Section 9.2 and in *Molecular Cloning: A Laboratory Manual, 2nd Edition*, Sambrook et al., 1989, Cold Spring Harbor Laboratory Press, Sections 16.41-16.46 or other standard laboratory manuals.

Electroporation

Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the nucleic acid and the ionic composition of the media. Electroporation can be used to stably (or transiently) transfect a wide variety of cell types. Protocols for electroporating cells can be found in Ausubel, F. M. et al. (eds.), supra, Section 9.3 and in Sambrook et al., supra, Sections 16.54-16.55 or other standard laboratory manuals.

Liposome-Mediated Transfection ("Lipofection")

Naked nucleic acid also can be introduced into cells by mixing the nucleic acid with a liposome suspension containing cationic lipids. The nucleic acid/liposome complex is then incubated with cells. Liposome mediated transfection can be used to stably (or transiently) transfect cells in culture in vitro. Protocols can be found in Ausubel, F. M. et al. (eds.), supra, Section 9.4 and other standard laboratory manuals. Additionally, gene delivery in vivo has been accomplished using liposomes. See for example Nicolau et al., 1987, *Meth. Enz.,* 149:157-176; Wang, et al., 1987, *Proc. Natl. Acad. Sci. USA,* 84:7851-7855; Brigham et al., 1989, *Am. J. Med. Sci.,* 298: 278; and Gould-Fogerite et al., 1989, *Gene,* 84:429-438.

Direct Injection

Naked nucleic acid can be introduced into cells by directly injecting the nucleic acid into the cells. For an in vitro culture of cells, nucleic acid can be introduced by microinjection. Since each cell is microinjected individually, this approach is very labor intensive when modifying large numbers of cells. However, a situation where microinjection is a method of choice is in the production of transgenic animals (discussed in greater detail below). In this situation, the nucleic acid is stably introduced into a fertilized oocyte which is then allowed to develop into an animal. The resultant animal contains cells carrying the nucleic acid introduced into the oocyte. Direct injection has also been used to introduce naked nucleic acid into cells in vivo (see e.g., Acsadi et al., 1991, *Nature,* 332: 815-818; Wolff et al., 1990, *Science,* 247:1465-1468). A delivery apparatus (e.g., a "gene gun") for injecting DNA into cells in vivo can be used. Such an apparatus is commercially available (e.g., from BioRad).

Receptor-Mediated DNA Uptake

Naked nucleic acid also can be introduced into cells by complexing the nucleic acid to a cation, such as polylysine, which is coupled to a ligand for a cell-surface receptor (see for example Wu, et al., 1988, *J. Biol. Chem.,* 263:14621; Wilson et al., 1992, *J. Biol. Chem.,* 267:963-967; and U.S. Pat. No. 5,166,320). Binding of the nucleic acid-ligand complex to the receptor facilitates uptake of the nucleic acid by receptor-mediated endocytosis. Receptors to which a nucleic acid-ligand complex have targeted include the transferrin receptor and the asialoglycoprotein receptor. A nucleic acid-ligand complex linked to adenovirus capsids which naturally disrupt endosomes, thereby releasing material into the cytoplasm can be used to avoid degradation of the complex by intracellular lysosomes (see for example Curiel et al., 1991, *Proc. Natl. Acad. Sci. USA,* 88:8850; Cristiano et al., 1993, *Proc. Natl. Acad. Sci. USA,* 90:2122-2126). Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest.

Ex Vivo Gene Transfer

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

Generally, when naked nucleic acid is introduced into cells in culture (e.g., by one of the transfection techniques described above) only a small fraction of cells (about 1 out of $10^5$) typically integrate the transfected nucleic acid into their genomes (i.e., the nucleic acid is maintained in the cell episomally). Thus, in order to identify cells which have taken up exogenous nucleic acid, it is advantageous to transfect nucleic acid encoding a selectable marker into the cell along with the nucleic acid(s) of interest. Preferred selectable markers include those which confer resistance to drugs such as G418, hygromycin and methotrexate. Selectable markers may be introduced on the same plasmid as the gene(s) of interest or may be introduced on a separate plasmid. Selectable markers may be "dominant"; a dominant selectable marker encodes an enzymatic activity which can be detected in any eukaryotic cell line.

Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., 1989, Molecular Cloning: A Laboratory Manual, 2nd ed., Cold Spring Harbor Laboratory Press, New York pp. 16.9-16.15.

Viral-Mediated Gene Transfer

A preferred approach for introducing nucleic acid encoding a gene product into a cell is by use of a viral vector containing nucleic acid, e.g., a cDNA, encoding the gene product. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

Nonreplicating viral vectors can be produced in packaging cell lines which produce virus particles which are infectious but replication-defective, rendering them useful vectors for introduction of nucleic acid into a cell lacking complementary genetic information enabling encapsidation (Mann et al., 1983, cell, 33:153; Miller and Buttimore, Mol. Cell. Biol., 1986, 6:2895 (PA317, ATCC CRL9078). Packaging cell lines which contain amphotrophic packaging genes able to transform cells of human and other species origin are preferred.

Retroviruses

The retroviruses are a group of single-stranded RNA viruses characterized by an ability to convert their RNA to double-stranded DNA in infected cells by a process of reverse-transcription (Coffin, 1990, in Fields et al., Ceds, *Virology*, Raven Press, New York, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, functions as a signal for packaging of the genome into virions. Two long terminal repeat (LTR) sequences are present at the 5' and 3' ends of the viral genome. These contain strong promoter and enhancer sequences and are also required for integration in the subject cell genome (Coffin, supra).

Defective retroviruses are well characterized for use in gene transfer for gene therapy purposes (for a review see Miller, 1990, Blood 76:271).

Protocols for producing recombinant retroviruses and for infecting cells in vitro or in vivo with such viruses can be found in *Current Protocols in Molecular Biology*, Ausubel, F. M. et al. (eds.), 1989, Greene Publishing Associates, Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al., 1985, Science, 230:1395-1398; Danos, et al., 1988, Proc. Natl. Acad. Sci. USA, 85:6460-6464; Wilson et al., 1988, Proc. Natl. Acad. Sci. USA, 85:3014-3018; Armentano et al., 1990, Proc. Natl. Acad. Sci. USA, 87:6141-6145; Huber et al., 1991, Proc. Natl. Acad. Sci. USA, 88:8039-8043; Ferry et al., 1991, Proc. Natl. Acad. Sci. USA, 88:8377-8381; Chowdhury et al., 1991, Science, 254:1802-1805; van Beusechem et al., 1992, Proc. Natl. Acad. Sci. USA, 89:7640-7644; Kay et al., 1992, Human Gene Therapy, 3:641-647; Dai et al., 1992, Proc. Natl. Acad. Sci. USA, 89:10892-10895; Hwu et al., 1993, J. Immunol., 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the subject genome to stably introduce nucleic acid into the cell. Thus, it may be necessary to stimulate replication of the target cell.

There are certain limitations to the use of retrovirus vectors in all aspects of the present invention. For example, retrovirus vectors usually integrate into random sites in the cell genome. This can lead to insertional mutagenesis through the interruption of subject genes or through the insertion of viral regulatory sequences that can interfere with the function of flanking genes (Varmus et al., 1981, Cell, 25: 23-36). Another concern with the use of defective retrovirus vectors is the potential appearance of wild-type replication-competent virus in the packaging cells. This can result from recombination events in which the recombinant virus inserts upstream from the gag, pol, env sequence integrated in the subject cell genome. However, new packaging cell lines are now available that should greatly decrease the likelihood of recombination (Markowitz et al., 1988, J. Virol., 62:1120-1124; Hersdorffer et al., 1990, DNA Cell Biol., 9:713-723).

Adenovirus

Knowledge of the genetic organization of adenovirus, a 36 kB, linear and double-stranded DNA virus, allows substitution of a large piece of adenoviral DNA with foreign sequences up to 7 kB (Grunhaus, et al., 1992, Seminar in Virology, 3:237-252). In contrast to retrovirus, the infection of adenoviral DNA into subject cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target-cell range, and high infectivity. Both ends of the viral genome contain 100-200 base pair (bp) inverted terminal repeats (ITR), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5' tripartite leader (TL) sequence which makes them preferred mRNAs for translation.

The genome of an adenovirus can be manipulated such that it encodes and expresses a gene product of interest but is inactivated in terms of its ability to replicate in a normal lytic viral life cycle. See for example Berkner, et al., 1988, Bio-Techniques, 6:616; Rosenfeld, et al., 1991, Science, 252:431-434; and Rosenfeld, et al., 1992, Cell, 68:143-155. Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses are advantageous in that they do not require dividing cells to be effective gene delivery vehicles and can be used to infect a wide variety of cell types, including airway epithelium (Rosenfeld, et al., 1992, cited supra), endothelial cells (Lemarchand, et al., 1992, Proc. Natl. Acad. Sci. USA, 89:6482-6486), hepatocytes (Herz, et al., 1993, Proc. Natl. Acad. Sci. USA, 90:2812-2816) and muscle cells (Quantin, et al., 1992, Proc. Natl. Acad. Sci. USA, 89:2581-2584). Additionally, introduced adenoviral nucleic acid (and foreign DNA contained therein) is not integrated into the genome of a subject cell but remains episomal, thereby avoiding potential problems that can occur as a result of insertional mutagenesis in situations where introduced nucleic acid becomes integrated into the subject genome (e.g., retroviral DNA). Moreover, the carrying capacity of the adenoviral genome for foreign DNA is large (up to 8 kilobases) relative to other gene delivery vectors (Berkner, et al. cited supra; Haj-Ahmand, et al., 1986, J. Virol., 57:267). Most replication-defective adenoviral vectors currently in use are deleted for all or parts of the viral E1 and E3 genes but retain as much as 80% of the adenoviral genetic material.

Recombinant adenovirus may be generated by methods known in the art, e.g., as described in U.S. Pat. No. 6,194,191, incorporated herein by reference.

Generation and propagation of the adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones, et al., 1978), the current adenovirus vectors, with the help of 293 cells, carry foreign DNA in either the E1, the E3 or both regions (Graham, et al., 1991). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication-defective and will not have an adenovirus E1 region. Thus, it will be most convenient to introduce the nucleic acid encoding a polypeptide of interest at the position from which the E1 coding sequences have been removed. However, the position of insertion of the coding region of a selected nucleic acid within the adenovirus sequences is not critical to the present invention.

Adenovirus is easy to grow and manipulate and exhibits broad subject range in vitro and in vivo. This group of viruses can be obtained in high titers, e.g., $10^9$-$10^{11}$ plaque-forming unit (PFU)/ml, and they are highly infective. The life cycle of adenovirus does not require integration into the subject cell genome.

Adenovirus vectors have been used in eukaryotic gene expression (Levrero, et al., 1991, Gene, 101:195-202; Gomez-Foix, et al., 1992, J. Biol. Chem., 267:25129-25134) and vaccine development (Grunhaus, et al., 1992, Seminar in Virology, 3:237-252; Graham, et al., 1992, Biotechnology, 20:363-390). Recently, animal studies suggested that recombinant adenovirus could be used for gene therapy (Stratford-Perricaudet, et al., 1991, in: Human Gene Transfer, O. Cohen-Haguenauer, Ceds), John Libbey Eurotext, France; Stratford-Perricaudet, et al., 1990, Hum. Gene Ther., 1:241-256; Rich, et al., 1993, Nature, 361:647-650). Experiments in administering recombinant adenovirus to different tissues include trachea instillation (Rosenfeld, et al., 1991, Science, 252: 431-434; Rosenfeld, et al., 1992, Cell, 68:143-155), muscle injection (Ragot, et al., 1993, Nature, 361:647-650), peripheral intravenous injection (Herz, et al., 1993, Proc. Nat'l. Acad. Sci. USA 90:2812-2816), and stereotactic inoculation into the brain (Le Gal La Salle et al., 1993, Science, 259:988-990).

Other Viral Vectors as Expression Constructs

Other viral vectors may be employed as expression constructs in the present invention. Vectors derived from viruses such as vaccinia virus (Ridgeway, 1988, in: Rodriguez R L, Denhardt D T, ed. *Vectors: A Survey of Molecular Cloning Vectors and Their Uses*. Stoneham: Butterworth, pp. 467-492; Baichwal, et al., 1986 In: Kucherlapati R, ed. Gene Transfer. New York: Plenum Press, pp. 117-148; Coupar, et al., 1988, Gene, 68: 1-10), adeno-associated virus (AAV) (Baichwal, et al., 1986, supra; Hermonat, et al., 1984, Proc. Natl. Acad. Sci. USA, 81:6466-6470) and herpes viruses may be employed. They offer several attractive features for various mammalian cells (Friedmann, 1989, Science, 244:1275-1281; Baichwal, et al., 1986, supra; Coupar, et al., 1988, supra; Horwich, et al., 1990, J. Virol., 64:642-650).

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al., 1992, Curr. Topics in Micro. and Immunol., 158:97-129). It is also one of the few viruses that may integrate its DNA into non-dividing cells, and exhibits a high frequency of stable integration (see, for example, Flotte et al., 1992, Am. J. Respir. Cell. Mol. Biol., 7:349-356; Samulski et al., 1989, J. Virol., 63:3822-3828; and McLaughlin et al., 1989, J. Virol., 62:1963-1973). Vectors containing as little as 300 base pairs of AAV can be packaged and can integrate. Space for exogenous nucleic acid is limited to about 4.5 kb. An AAV vector such as that described in Tratschin et al., 1985, Mol. Cell. Biol., 5:3251-3260 can be used to introduce nucleic acid into cells. A variety of nucleic acids have been introduced into different cell types using AAV vectors (see for example Hermonat, et al., 1984, Proc. Natl. Acad. Sci. USA, 81:6466-6470; Tratschin, et al., 1985, Mol. Cell. Biol., 4:2072-2081; Wondisford, et al., 1988, Mol. Endocrinol., 2:32-39; Tratschin, et al., 1984, J. Virol., 51:611-619; and Flotte, et al., 1993, J. Biol. Chem., 268:3781-3790).

The efficacy of a particular expression vector system and method of introducing nucleic acid into a cell can be assessed by standard approaches routinely used in the art. For example, nucleic acid introduced into a cell can be detected by a filter hybridization technique (e.g., Southern blotting) and RNA produced by transcription of introduced nucleic acid can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a separate gene product which is easily detectable and, thus, can be used to evaluate the efficacy of the system. Standard reporter genes used in the art include genes encoding β-galactosidase, chloramphenicol acetyl transferase, luciferase, human growth hormone, GF, EGFP and the like.

The methods described above to transfer nucleic acid into cells are merely for purposes of illustration and are typical of those that might be used. However, other procedures may also be employed to obtain expression of selected molecules in cells, as is understood in the art.

Antigen Pulsing

In a preferred embodiment of the invention, an alternative to the antigen expression scheme described above is utilized. It is well known in the art that antigen presenting cells can be pulsed with antigen as an alternative to expression of the antigen from within the antigen presenting cell. A description of the general methodology of antigen pulsing can be found, for example, in WO 94/02156; U.S. Pat. No. 6,737,062; and U.S. Pat. No. 6,689,757, and the techniques involved are well understood by those skilled in the art. More specifically, APC pulsing protocols useful in the present invention comprising pulsing APC cells with peptide antigen at a concentration of 10 μg/ml in serum free media for 6-10 hours at room temperature. It will be readily appreciated by one of ordinary skill in the art, that the specific parameters for antigen pulsing may vary according to, for example, the specific cell type or peptide antigen of interest.

Selection of Modified APCs

As discussed above, in one aspect, the invention provides fusion proteins comprising a heterologous polypeptide fused in frame to a selected antigen at the N-terminus of the antigen. The fusion of the heterologous polypeptide to the N-terminus of the antigen shields the antigen from the proteolytic activities of cellular proteosomes. Preferably, the heterologous polypeptide is cleaved from the antigen portion of the fusion by a cell-associated protease which cleaves a linker polypeptide inserted between the heterologous polypeptide and the antigen. The antigen is released from the heterologous polypeptide and transported to the cell surface, preferably bound to an antigen-presenting molecule (which can be endogenous or exogenous) where the antigen and antigen-presenting molecule can be recognized by one or more cells of the immune system. Most preferably, the C-terminus of the antigen-heterologous polypeptide fusion is the C-terminus of a minimal antigen sequence (e.g., the smallest antigenic peptide sequence which can bind to an antigen-presenting molecule and elicit an immune response).

Cells expressing fusion proteins according to the invention can be detected and selected for in a variety of ways. In one aspect, the heterologous polypeptide is a reporter polypeptide detectable within the cell before and/or after cleavage of the heterologous polypeptide from the antigen. As described above, preferably, the reporter polypeptide used in the invention is an autofluorescent protein (e.g., GFP, EGFP). Autofluorescent proteins provide a ready assay for identification of expression of a nucleic acid of interest. Because the activity of the polypeptide (and by inference its expression level) can be monitored quantitatively using a flow sorter, it is simple to assay many independent transfectants either sequentially or in bulk population. The best APCs can then be screened for or selected from the population based on the expression levels of the critical molecules. Quantitative parameters such as mean fluorescence intensity and variance can be determined from the fluorescence intensity profile of the cell population (Shapiro, H., 1995, Practical Flow Cytometry, 217-228).

A flow sorter can be used not only as a screen to examine the expression of nucleic acid of interest in transfected cells, but also as a tool to manipulate and bias the cell populations in potentially useful ways. For example, in certain cases it may be helpful to select cells expressing high level of a first nucleic acid, in other cases it may be helpful to select cells expressing high level of a second nucleic acid, but low level of the first nucleic acid. Alternatively, it may be desirable simply to exclude cells that do not express a nucleic acid at a desired level above the background. The flow sorter permits such selections to be carried out with extraordinary efficiency because cells can be sorted at a rate of ten to one hundred million per hour (Shapiro H., 1995, Practical Flow Cytometry, 217-228).

In some aspects, when there are two or more nucleic acids used to transfect cells (e.g., antigen encoding nucleic acid molecules and nucleic acid encoding antigen-presenting molecules or immunomodulatory molecules), it is preferred that a reporter molecule fused to each nucleic acid generates different detectable signals so the expression of each nucleic acid may be distinguished.

In another aspect, the heterologous polypeptide can provide a function to the cell which can be selected for, e.g., such as the ability to survive in a selection medium. Survival can conferred by providing a heterologous polypeptide which confers antibiotic resistance or which can render a toxic agent in a medium non-toxic to a cell in which it is expressed.

In a further aspect, the heterologous polypeptide is bindable to an antibody which can be used to identify, sort, and purify cells containing the heterologous polypeptide. For example, the heterologous polypeptide can be a cell surface polypeptide which can be expressed on the cell surface independently of the antigen. Expression of the heterologous polypeptide can be confirmed by an immunoassay such as an ELISA (enzyme-linked immunoabsorbent assay) (see e.g., U.S. Pat. No. 5,962,320; U.S. Pat. No. 6,187,307; U.S. Pat. No. 6,194,205), by FACS (Fluorescent Activated Cell Sorting), or by other methods routine in the art, and cells expressing the heterologous polypeptide can be purified from cells not expressing the polypeptide by affinity-based techniques such as magnetic sorting, panning, and affinity column purification assays.

However, in some aspects, the heterologous polypeptide is not cleaved from the antigen and the antigen:heterologous polypeptide fusion is presented on the surface of the cell. Preferably, the heterologous polypeptide retains its function as a reporter molecule or molecule which confers survival on a cell, and/or provides one or more epitopes which can be recognized by a binding partner such as an antibody which can be alternatively, or additionally, used to select cells comprising the fusion protein as described above. The heterologous polypeptide portion of the fusion also can be processed to some extent by cellular proteosomes. Preferably, less than 50% of the heterologous polypeptide is processed.

As discussed above, selection of modified APCs also may be based on the ability of the cells to generate an antigen-specific immune response (e.g., such as a CTL response). In this aspect, the heterologous polypeptide need not function as a reporter polypeptide or a polypeptide which confers survival on a cell and need not comprise an epitope recognizable by an antibody or other binding partner so long as the heterologous polypeptide minimally functions to shield the antigen portion of the fusion from proteolytic processing by cellular proteosomes. Such a cell also need not be purified from other non-modified APCs, so long as sufficient numbers of modified APCs can be obtained (e.g., to obtain a therapeutic effect, as discussed further below).

Determining the Antigen-Presenting Activity of the APCs

Biological activity of the modified cells can be verified, for example, in vitro assays and in animal models such as mice or non-human primates prior to testing in humans. The ability of the modified cells of the invention to function as desired, e.g. to process and present antigen for enhancing or suppressing an immune response, may be tested using in vitro and/or in vivo assays.

CTL lysis of target cells depends on presentation of foreign antigen peptides bound to class I MHC molecules. Thus, efficacy of the APCs of the invention will be determined in part by the ability of the introduced selected antigens to form peptide/MHC complexes on the surface of the modified APCs.

To determine activity of the modified APCs, the following can be determined by methods well known in the art (e.g., as described in Coligan et al., supra): expression of the introduced selected antigen (e.g., by western analysis); binding of the antigen or fragment to class I MHC molecules on the APC surface (e.g., by immunoassays and mass spectroscopy); and stimulation of CTL lysis of subject cells bearing the selected antigen (e.g., by CTL and cell proliferation assays). To determine expression of the introduced selected antigen, antibodies which recognize the antigen may be labeled and binding to the APCs determined using conventional techniques, such as an ELISA or Western blotting.

To determine if the expressed selected antigen will become bound to the class I MHC (and thus transported to the surface of the modified APC), procedures such as mass spectrometric analysis of transfected APCs may be used. Alternatively, binding to class I MHC molecules can be confirmed using an in vitro antigen-specific T cell activity assays in response to stimulation by MHC antigens, such as described by Coligan, et al. supra, Unit 3.11.

T cell activation may be detected by various known methods, including measuring changes in the proliferation of T cells, killing of target cells and secretion of certain regulatory factors, such as lymphokines, expression of mRNA of certain immunoregulatory molecules, or a combination of these. The effects of the modified cells on T cell activation may then be determined using in vitro assays, or by introducing the modified cells into an animal model, such as a mouse, and subsequently measuring the immune response of the mouse to the selected antigen with controls in which no engineered cells or differently engineered cells were introduced. For example, the APCs may be introduced into an animal model, such as a mouse or non-human primate, to determine whether the APCs of the invention can stimulate CTL responses against selected antigens. One such model for determining antigen-specific CTL activity uses mice lacking endogenous active T lymphocytes, such as nude or irradiated mice. Adoptive transfer of selected antigen primed CTLs into such mice in which cells bearing the selected antigen (e.g., cancer cells) have also been introduced permits in vivo assessment of the lytic ability of the transferred CTLs against the introduced cells (see protocols for adoptive transfer, CTL depletion and in vivo T cell activity assays, in Coligan, et al., supra at Unit 4.1; and Shastri, et al., 1993, J. Immunol. 150:2724-2736).

Similarly, selective induction of a $T_h$ 1 or $T_h$ 2 immune response, can be determined by, for example, introducing the cells of the invention into an animal model, e.g., a mouse, and measuring the production of specific lymphokines or the expression of their RNAs in spleen cells. In addition, production of IgG 2A antibodies (serological markers for a $T_h$ 1 response) as compared to production of IgG 1 antibodies (markers for a $T_h$ 2 response) can be measured using standard methods, such as an ELISA.

Immune effector cell (e.g., T cell) activation induced by an APC of the present invention can be compared to the activation induced by a control cell (e.g., the unmodified cell used to construct the APC). A change (e.g., an increase of activation of at least 20%, or 40% or 60% or 80%, or 100% or greater, such as 2 fold, 4 fold, or at least 10 fold, 20 fold, 50 fold or 100 fold or greater) would indicate a useful APC generated.

Where populations of cells are selected which comprise modified APCs, preferably, at least 50% of the cells of such a population are capable of generating an antigen specific immune response such that the population can be used to effect a 10% greater or at least two-fold greater immune response than a control population not comprising any modified APCs.

Assays for Determining Immune Response Modulation

The APCs of the invention are useful in modulating an immune response in an animal, preferably a mammalian, more preferably a human, to an antigen or antigens.

An "immune response" refers to stimulation/activation of a selected response involving the immune system, or suppression, elimination, or attenuation of a selected response. Thus, a modulation in an immune response means a change of a desired response in its efficacy, rapidness, and/or magnitude caused by a modified APC of the invention when compared to a control cell in an identical fashion, where the change is at least 20%, or 40% or 60% or 80%, or 100% or greater, such as 2 fold, 4 fold, or at least 10 fold, 20 fold, 50 fold or 100 fold or greater.

The following in vitro and in vivo assays are useful examples for determining whether an immune response is modulated according to the invention. The assays described in detail below measure stimulation or suppression of cellular or humoral immune responses to an antigen. The antigens referred to in the following assays are representative and non-limiting. It will be apparent to one of skill in the art that an immune response to a selected antigen useful according to the invention may be measured using one or more of the following assays by adapting the assay to that antigen.

Amplification of the immune response usually involves proliferation of particular subpopulations of lymphoid cells that are normally in the resting state.

T cell proliferation assays can be used to measure the stimulation of immune response by an antigen presenting cell. One way of performing proliferation assay is to measure incorporation of [$^3$H]thymidine into DNA, which usually correlates well with cell growth as measured by changes in cell number (e.g., see Coligan et al., supra).

An APC cell of the present invention may be used to stimulate the proliferation of a population of T cells as described in Coligan et al., supra. An immune modulation is achieved by the APC cell if a change in T cell proliferation rate stimulated by the modified APC is at least 20%, or 40% or 60% or 80%, or 100% or greater, such as 2-fold, 4-fold, or at least 10-fold, 20-fold, 50-fold or 100-fold or greater, when compared to a control cell (e.g., the unmodified cell used to construct the modified APC) in an identical fashion.

Immune response may also be measured by lymphokine production from T cells as described in Coligan et al., supra. An immune modulation is achieved by the APC cell if a change in T cell lymphokine production stimulated by the modified APC is at least 20%, or 40% or 60% or 80%, or 100% or greater, such as 2 fold, 4 fold, or at least 10 fold, 20 fold, 50 fold or 100 fold or greater, when compared to a control cell (e.g., the unmodified cell used to construct the modified APC) in an identical fashion.

The ability of APCs to stimulate a specific CTL response can be used to measure the activation of T cells by an APC cell. APCs of the invention can be injected into an animal model (e.g., a mouse). T cells can be isolated from the mouse following the injection (usually two or more days after the injection) for CTL assays (e.g., a chromium release assay, see Coligan et al., supra). T cells can be purified from other cells by methods known in the art. For example, negative selection can be used to remove unwanted cells such as B cells or monocytes by using antibodies which recognize markers on these cells and removing cell:antibody complexes. Positive selection also can be used in which an antibody specific for a T cell marker is used to select for T cells.

Immune modulation is achieved by an APC cell if a change in CTL activity of T cells stimulated by the modified APC is at least 20%, or 40% or 60% or 80%, or 100% or greater, such as 2-fold, 4-fold, or at least 10-fold, 20-fold, 50-fold or 100-fold or greater, when compared to a control cell (e.g., the unmodified cell used to construct the modified APC) in an identical fashion.

The ability of the APCs according to the invention to modulate immune responses can be illustrated by their effect in the delayed type hypersensitivity (DTH) test in mice. The DTH test is used to illustrate immunomodulation, the protocol for which is described, for example, by Carlsten, et al, 1986, Int. Arch. Allergy Appl. Immunol., 81:322, herein incorporated by reference. An immune modulation is achieved by the APC cell if a change in DTH stimulated by the modified APC is at least 20%, or 40% or 60% or 80%, or 100% or greater, such as 2 fold, 4 fold, or at least 10 fold, 20 fold, 50 fold or 100 fold or greater, when compared to a control cell (e.g., the unmodified cell used to construct the modified APC) in an identical fashion.

It should be obvious to those of skill in the art that such assays can also be used to identify populations of professional APCs as described above which are capable of mediating a desired level of an immune response. Such populations can comprise one or more cells that are not professional APCs although preferably, at least 50% of the cells are professional APCs.

Methods of Using Modified APCs

The APCs described herein which are modified to present antigens can be used in a cell-based therapeutic vaccine to direct the immune response to treat infectious diseases, cancer, and unwanted immune responses, such as autoimmune disease, transplant rejection and allergic reactions by selecting and using cells expressing an antigen-presenting molecule such as an MHC/HLA antigen matched to the MHC/HLA specificity of the patient to be treated.

The MHC/HLA compatibility permits the modified cells to present antigens that are properly recognized by T cells in the subject into which the cells are introduced. The cells express antigens and molecules selected to enhance or suppress the immune response, as described above and are administered in a therapeutically effective dose to the patient.

Modified APCs according to the invention also can be used as a protective cell-based vaccine to induce immunity that prevents new infection in uninfected subjects. The cells express antigen-presenting molecules such as MHC/HLA molecules matching those of the subject to be immunized and selected antigens. However, an exact match is not necessary so long as the APCs are able to stimulate T cells in an antigen specific manner such that the T cell can react with an autologous cell (e.g., a tumor or virus-infected host cell) that expresses the antigen.

The modified cells described herein can also be used as target cells to assay antigen-specific cytotoxic activity of T lymphocytes of a MHC/HLA compatible subject.

Advantages of the invention include the fact that non-autologous cells may be used to treat subjects, making a source of cells more readily available. For example, a "bank" of universal APCs may be prepared as described herein consisting of a plurality of different cells each expressing a different antigen-presenting molecule determinant such as a different HLA type, including the most common MHC/HLA types. In addition, cells expressing each MHC/HLA type are further modified to express one or more selected antigens for therapeutic or protective immunization, or to suppress an unwanted immune response. The modified cells can be propagated in cell culture to generate large numbers of cells and the cells can be stored, e.g. in liquid nitrogen, for convenient recovery for therapeutic use, or for use as target cells for assays of antigen-specific CTLs in a subject.

Pharmaceutical Preparation of Modified APCs

The APCs of the invention expressing one or more selected antigens or active portions thereof, and antigen-presenting molecules having the specificity of the subject to be treated, are grown in cell culture using standard methods (see, e.g. Darling, 1994, "Animal Cells: Culture and Media", J. Wiley, New York; and Freshney, 1987, "Culture of Animal Cells". Alan R. Liss, Inc., New York). The cells may also express other immunoregulatory molecules such as costimulatory molecules and cytokines.

The modified cells are suspended in any known physiologically compatible pharmaceutical carrier, such as cell culture medium, physiological saline, phosphate-buffered saline, cell culture medium, or the like, to form a physiologically acceptable, aqueous pharmaceutical composition. Parenteral vehicles include sodium chloride solution, Ringer's dextrose, dextrose and sodium chloride, lactated Ringer's. Other substances may be added as desired such as antimicrobials.

As used herein, a "carrier" refers to any substance suitable as a vehicle for delivering an APC to a suitable in vitro or in vivo site of action. As such, carriers can act as an excipient for formulation of a therapeutic or experimental reagent containing an APC. Preferred carriers are capable of maintaining an APC in a form that is capable of interacting with a T cell. Examples of such carriers include, but are not limited to water, phosphate buffered saline, saline, Ringer's solution, dextrose solution, serum-containing solutions, Hank's solution and other aqueous physiologically balanced solutions or cell culture medium. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer.

In Vitro/Ex Vivo Applications

The modified APCs of the invention can be used in assays to assess the activity of a subject's antigen-specific CTLs, or to stimulate immune effector cells for ex vivo therapy.

Cell preparations containing immune effector cells (e.g., T lymphocytes) can be isolated from a selected subject.

T lymphocytes and monocytes can be prepared by apheresis from blood samples. "FICOLL HYPAQUE" gradient centrifugation (Boyuwn, supra) followed by four-layer "PERCOLL" (Pharmacia, Uppsala, Sweden) discontinuous centrifugation (Markowicz and Engleman, supra) can be used. Monocytes can be removed from the interface over the "PERCOLL" 50.5% layer, whereas T lymphocytes can be collected from the high buoyant density (HD) fraction, or interface between 75% and 50.5% layers. The cells may be propagated in cell culture in the presence of IL-2 and the antigen to which an antigen specific CTL response or proliferation is to be assayed.

Other ways to isolate T cells include negative or positive selections using cell-specific antibodies. In negative selection, unwanted cells (e.g., B cells, monocytes) can be removed from blood samples using antibodies against these unwanted cells. In positive selection, antibodies specifically recognizing T cells are used to purify T cells from the blood samples. Antibodies against specific cells are commercially available (e.g., from BD Biosciences, San Jose, Calif.).

CTL Assays

Cytotoxic activity can be measured, for example, by $^{51}$Cr release from $^{51}$Cr labeled target cells in a standard CTL assay format. For example, an APC cell prepared according to the methods of the invention and having a matched HLA antigen specificity to a patient's T lymphocytes can be labeled with $^{51}$Cr and used as the target cell for the cytotoxicity assays.

Target cells can be incubated with $^{51}$Cr (NEN DuPont, Wilmington, Del.) for 2 hours at 37° C. Excess unlabeled 51 Cr in the supernatant is then washed off by sequential centrifugal washing steps in AB Culture Medium. Radiolabeled target cells are then suspended in cell culture medium and a number such as 2000 target cells are added to each well of a 96-well microtiter plate. Different numbers of cells of the T cell-containing preparations (effector cells) can be added to different wells to make a series of effector cell:target cell ratios of 1:1 to 100:1. Following incubation, the plates are centrifuged to pellet the cells, and aliquots of the supernatant from each well are assayed for $^{51}$Cr in a gamma counter. Controls for spontaneous release of $^{51}$Cr (in the absence of subject immune cells or with unmodified cells used as target cells), and for maximal $^{51}$Cr by adding detergent Triton X-100 (Sigma Chemical Co., St. Louis, Mo.) to target cells are carried out in parallel.

The percentage specific release is calculated as:

(experimental release–spontaneous release)/(total release–spontaneous release)×100

In one embodiment, APCs are isolated from a human patient, treated and returned to the patient in the form of modified APCs (e.g., in ex vivo somatic therapy, in vivo implantable devices and ex vivo extracorporeal devices).

Proliferation Assays

Generally, effector cells are cultured with irradiated modified APCs. Peripheral blood mononuclear cells (PBMCs) or peripheral blood lymphocytes (PBLs) from a selected subject can be added to the modified APCs, e.g., at a ratio of from 1:5 to 100:1, preferably 40:1. In a specific embodiment, the PBMCs are added to modified APCs. In another embodiment, the PBMCs are added to unmodified cells. The modified APCs stimulate proliferation of antigen- or virus-specific effector cells; non-specific effector cells (CD4 and CD8 T cells) do not proliferate. Thus, the methods of the invention enrich for a population of effector cells consisting of modified APCs.

Although PBMCs or PBLs are readily obtained and very easy to use as the source of effector cells, selection or isolation techniques can be used to enrich the effector population further (see Coligan, supra). For example, the cells can be depleted of CD56-positive lymphocytes. Alternatively, CD3-positive cells, α, β-T cell receptor-positive cells, or even γ, δ-T cell receptor positive cells can be selected (or depleted), e.g., by FACS or panning. B cells present in PBMCs or PBLs can be depleted, e.g., by panning or anti-Ig plus complement. T lymphocytes can be selected by nylon wool passage as well.

The effector cells are generally co-cultured with the irradiated APCs for about 7 to 14 days, and preferably about 10 days. Preferably, the effector cells are harvested and restimulated with fresh APCs. At least two cycles of stimulation are necessary to get a highly enriched population of antigen-specific effector cells. Additional stimulation cycles will result in maintenance of a highly specific population of effector cells, but will not provide significantly greater specificity.

As discussed above, the effector cells generated according to the invention are useful for immunotherapy for active and latent viral infections. CTL immunotherapy may also prove useful for the treatment of adult malignant tumor; for recipients of heart, heart-lung or bowel transplant and for other transplant recipients since transplant patients are often at risk for various viral infection. Papilloma virus, which causes laryngeal papillomatosis in infants, as well as certain head, neck and cervical cancers in adults also may be treatable with CTL immunotherapy. AIDS patients, who are severely immunocompromised and susceptible to opportunistic infections including herpes virus and CMV, represent another group who may be treated with CTL immunotherapy.

As discussed above, either the transfected APCs of the invention can be used to generate a population of effector cells specific for more than one pathogen. Ideally, multi-pathogen effector cells are given prophylactically, after bone marrow transplantation, immunosuppressive therapy for organ transplantation, or chemotherapy.

Modified APCs of the present invention also can be employed in the screening of or testing of antigenicity and immunogenicity of peptide epitopes from tumor- and microbe-specific antigens.

In certain cases, it may be advantageous to use cells obtained from one subject to treat a condition in a second subject. For example, HIV-infected subjects with AIDS are often not able to mount anti-viral T-cell responses. In such cases, CTL can be isolated from healthy HLA-matched subjects, such as siblings, be stimulated or primed with APCs of the invention in vitro, expanded, and administered back to the HIV-infected subjects.

In Vivo Immunotherapy Using the Modified APCs of the Invention

The cell(s) of the invention can be administered to a mammal, e.g., in a method of treating or preventing a pathogen (e.g., a microbe such as a bacterium infection virus or a cancer in a mammal). Such cell(s), when combined with a pharmaceutically acceptable excipient, provide a vaccine against a protein (e.g., a toxin of a microbe) containing the antigen with which the cell was contacted. Accordingly, such a vaccine can be used in treating or preventing cancer or a pathogen infection (e.g., an intracellular pathogen infection).

One aspect of the invention provides a method to regulate an immune response by administering to an animal an effective amount of APCs of the invention. Subject dose size, number of doses, frequency of dose administration, and mode of administration can be determined and optimized using methods known in the art (see, e.g., Hardman et al., Ceds 1995, Goodman & Gilman's *The Pharmacological Basis of Therapeutics*, Ninth Edition, McGraw-Hill).

The manner of administration of a therapeutic reagent of the present invention can depend upon the particular purpose for the delivery (e.g., treatment of disease or delivery of an imaging reagent), the overall health and condition of the patient and the judgement of the physician or technician administering the target vehicle. A therapeutic reagent of the present invention (e.g., modified APCs) can be administered to an animal using a variety of methods. Such delivery methods can include parenteral, topical, oral or local administration, such as intradermally. A therapeutic reagent can be administered in a variety of unit dosage forms depending upon the method of administration. Preferred delivery methods for a therapeutic reagent of the present invention include intravenous administration, local administration (e.g., intratumoral) by, for example, injection, intradermal injection, intramuscular injection, intraperitoneal injection and inhalation. For particular modes of delivery, a therapeutic reagent of the present invention can be formulated in an excipient of the present invention. A therapeutic reagent of the present invention can be administered to any animal, preferably to mammals, and more preferably to humans.

The modified APCs may be irradiated prior to administration to control their growth in the patient.

The invention further provides a method for specifically modifying the immune system response of an animal to an antigen. The method involves administering the above-described pharmaceutical composition to the mammal. In a preferred embodiment, the APCs are stored in aliquots containing an amount of APCs sufficient to boost the immune response of the mammal as determining from previous tests. As described above, determination of the amount of cells necessary to stimulate the patient's immune response is within the ordinary skill of the art. Preferably, an amount of cells ranging from a minimum of about 25,000 to about $200 \times 10^6$ APCs is sufficient to boost the immune response of the patient. The amount of cells used will, in part, be dependent upon whether the APCs are efficient, e.g., their ability to trigger a specific CTL response.

After immunization, the efficacy of the therapy is assessed by a number of methods, such as assays that measure T cell proliferation, T cell cytotoxicity, antibody production or reduction in the number of antigen positive cells or tissues and/or clinical response. Therapeutic efficiency may also be measured by the increase of antigen specific cells by methods such as Tetramer staining or ELISPOT (see Skinner et al., 2000, J. Immunol. 165:613-7; Czerkinsky et al., 1983, J Immunol Methods 65:109-21). An increase (e.g., at least 20%, 30%, 40%, 50%, 60%, 70%, 80% or more, such as 2 fold, 3 fold, 4 fold, 5 fold, 10 fold or more) in the production of antibodies or immune cells recognizing the selected antigen will indicate an enhanced immune response.

Similarly, an increase in specific lytic activity or specific cytokine production by the subject's immune cells (e.g., detectable by methods known in the art), or tumor regression (e.g., at least 10%, or 20%, or 40%, or 60% or 80% or more of tumor size reduction or decrease in numbers of tumor cells) will indicate efficacy. Efficacy may also be indicated by reduction in the amount or elimination of a virus or other infectious agent (e.g., at least 10%, 20%, 30%, 40%, 60%, 80% or more reduction at titer), or improvement in or resolution of the disease (pathologic effects as measured by observing fewer or less severe symptoms), associated with the reduction or disappearance of the unwanted immune response, or improvement in or resolution of the disease (pathologic effects) associated with the unwanted immune response (e.g. autoimmune disease) allergic reaction or transplant rejection as determined by a medical practitioner.

The therapeutic effects of the invention result from stimulation, or enhancement, or suppression of an antigen-specific immune response by the introduced modified APC cells.

Animal Models

The therapeutic effects of the modified APCs may be tested in various animal models.

Mouse models for infectious disease, tumor and immunodeficiency disorders are known in the art and can be found, for example, on Jackson laboratory mouse database (Jackson Labs, Bar Harbor, Me.). For example, tumor mouse models include those used for the study of Chronic Myelogenous Leukemia (CML), defects in cell cdhesion molecules, genes regulating growth and proliferation, growth factors/receptors/cytokines, increased tumor incidence, oncogenes, toxicology and tumor suppressor genes. Mouse models for immunology and inflammation diseases include those made for the study of CD antigens, antigen receptors, and histocompatibility markers, growth factors/receptors/cytokines, immunodeficiency and autoimmunity, inflammation, intracellular signaling molecules, lymphoid tissue defects, mechanisms of HIV infection, rearranged antigen-specific t cell receptor transgenes, T cell receptor signaling defects, and vaccine development. Mouse models of other human diseases are available also through Jackson Labs (Bar Harbor, Me.). A listing of the mouse models of human disease useful in the present invention may be found on the World Wide Web, at jax.org.

Alternatively, viruses or live tumor cells can be injected into mice to create disease models for the testing.

Mice with different haplotypes may be used in practicing the invention. For example, BALB/c mice provide an $H-2^d$ background, and CBA mice provide an $H-2^k$ background.

The practice of the present invention employs conventional techniques of molecular biology, microbiology, recombinant DNA and immunology, within the skill of these arts. Such techniques are found in the scientific literature. (See, e.g., Brock, 1997, *Biology of Microorganisms*, Eighth Ed., (Madigan et al., eds.), Prentice Hall, Upper Saddle River, N.J.; Sambrook, et al., 1989, *Molecular Cloning: A Laboratory Manual*, Second Ed.; M. J. Gait Ed., 1984, *Oligonucleotide Synthesis, Animal Cell Culture*, Freshney, ed., 1987; *Methods In Enzymology*, series, Academic Press, Inc.; Miller, et al., Eds., 1987, *Gene Transfer Vectors for Mammalian Cells*; Weir, et al., Eds., 1987, *Handbook of Experimental Immunology, Current Protocols in Molecular Biology*, Ausubel et al., Eds., and Coligan, et al., Eds., 1991, *Current Protocols in Immunology*).

EXAMPLES

Using the compositions and methods described above, the present invention provides the following example of the generation of modified antigen presenting cells of the invention, and their use in the preparation of cytotoxic T lymphocyte cell lines.

Characterization of K562

The human erythroleukemia tumor cell line, K562, was characterized for cytokine production and cell surface phenotype. Cytokine expression profile (Table 1) was determined by protein ELISA assays per manufacturer's recommendations (R&D Systems for all cytokines except IL-7, Cell Sciences). K562 was also analyzed for the surface expression by FACS Beckman Coulter). To generate the molecularly engineered APC, MEA1, we transduced the genes encoding for HLA-A*0201, CD80 and CD83 using a retroviral vector. Cell lines were sorted to purity (FIG. 1) by multiple rounds of FACS staining and cell sorting using the EPICs Elite and Altra 2000 cell sorters (Beckman Coulter).

As shown in Tables 7 and 8, the K536 cell line endogenously expresses some adhesion molecules and cytokines, but it does not secrete IL2, IL7, IL 10, IL15, or γ-Interferon. While K562 expresses important adhesion molecules such as CD54 and CD58, it lacks expression of HLA class I or 11, CD83 or high expression of CD80. In order to generate the Molecularly Engineered APC (MEA1), HLA-A2*0201, CD80 and CD83 were introduced using a retroviral system. FIG. 12 demonstrates the high expression of transduced molecules expressed by the MEA1 cell line following multiple rounds of FACS sorting.

TABLE 7

Profile of Cytokines Produced by K562

| Cytokines | Conditioned Media (pg/ml) |
|---|---|
| IFN-γ | — |
| IL-2 | — |
| IL-2 sRα | — |
| IL-3 | — |
| IL-4 | — |
| IL-4 sR | — |
| IL-5 | — |
| IL-6 | 28 |
| IL-6 sR | 26.7 |
| IL-7 | — |
| IL-8 | 454 |
| IL-10 | — |
| IL-12 | — |
| IL-12 p40 | — |
| IL-15 | — |
| GM-CSF | — |
| MCP-1 | 318 |
| MIP-1α | 18* |
| MIP-1β | — |
| RANTES | 19 |
| TGF-β1 | 1330* |
| TNF-α | — |

One million MEA1 Cells were incubated in RPMI media supplemented with FCS at 37° C. Supernatant was harvested at 24 hours. Cytokine levels were determined by ELISA according to the manufacturer's instruction with the exception of MIP-1α, MIP-1β, RANTES, IL-2sα, where standard curves were extended to include lower concentrations.
*Levels were not detected in media alone with the exception of TGF-β1 = 826 pg/ml, MIP-1α = 13.9 pg/ml.

TABLE 8

Cell Surface Staining as Measured by FACS

| K562 | Expression Level |
|---|---|
| Class I | -- |
| Class II | -- |
| B7-H1 (PD-L1) | -- |
| B7-H2 (ICOS-L) | -- |
| B7-H3 | ++ |
| PD-L2 | -- |
| CD80 (B7-1) | +/- |
| CD86 (B7-2) | -- |
| CD40 | -- |
| CD154 (CD40L) | -- |
| CD209 (DC-Sign/Sign 2) | -- |
| CD27 | -- |
| CD70 | -- |
| CD83 | -- |
| CD95 (FAS) | -- |
| CDw137L (4-1BB Ligand) | -- |
| CD54 (ICAM-1) | ++ |
| CD58 (LFA-3) | ++ |
| CD64 (FCγRI) | -- |
| CD32 (FCγRII) | ++ |
| CD16 (FCγRIII) | -- |
| CD206 | -- |

CTL Line Generation

To establish antigen specific T cell lines, MEA 1 cells were pulsed with peptide at 10 μg/ml in serum free media for 8-10 hours at room temperature. For stimulations with peptide pulsed MEA1 and for assays using peptide pulsed T2 cells, the following peptides were used: MART-1, M27 (EAAGIGILTV); SEQ ID NO: 1; S9C, NY-ESO-1, (SLLMWITQC); SEQ ID NO: 2; Htert, 1540 (ILAKFLHWL); SEQ ID NO: 3; Her2/neu, E75 (KIFGSLAFL); SEQ ID NO: 4; HIV, pol (ILKEPVHGV); SEQ ID NO: 5; and influenza, MP58 (GILGFVFTL); SEQ ID NO: 6. Peptide-HLA-A2 multimers were synthesized around the same peptides with the exception of MART-1 where multimers with synthesized around the MART-1 heteroclytic peptide, A27L (ELAGIGILTV); SEQ ID NO: 7. MEA1 cells were then radiated with 20,000 Rads, washed, and added to purified CD8 T cells at a ratio of 1:20 in 24 well plates in RPMI supplemented with human AB sera. Purified CD8 T cells were obtained by positive selection (CD8 Positive Isolation Kit, Dynal) of PBMC obtained from normal donors. Cultures were supplemented with IL2 (5-10 IU/ml) and IL15 (5-10 ng/ml) every 3-4 days. Repeat stimulations were performed every 7-14 days.

FIG. 13, shows a scheme for CTL generation using MEA1. Here, antigen specific CTL lines are readily established from donor PBMC when highly purified CD8 T cells (>95%) are co-cultured with irradiated, peptide pulsed MEA1 and grown in the presence of IL2 (5-10 IU/ml) and IL15 (5-10 ng/ml). Since this strategy can be applied to any HLA molecule that could be introduced into MEA1, CTLs recognizing any HLA restricted epitope can be generated using this system.

To demonstrate that we are able to generate large numbers of antigen specific CTLs using this approach, we purified CD8 T cells from normal donors which we subsequently stimulated with peptide pulsed MEA1. Each antigenic epitope was chosen in order to demonstrate CTL generation against a recall antigen (influenza, MP58) or a naïve antigen (MART-1, M27).

Characterization of CTL Lines

Percentage of antigen specific CD8 T cells in generated lines was determined by staining with flurochrome labeled multimers, which were synthesized around the appropriate peptide. Absolute numbers of generated T cells were determined by multiplying the percentage of multimer staining cells by the total number of generated T cells. Effector function of antigen specific T cells was determined by a standard chromium release assay and a γ-Interferon ELISPOT (Mabtech) using peptide pulsed T2 cells as targets. T cell phenotype was determined by FACS (monoclonal antibodies were obtained from Caltag, with the exception of anti-CD25 (Coulter) anti-CD69 (BD Pharmingen) and anti-CCR7 (R&D). TCR Vβ typing was performed using the IOTest Beat Mark TCR Vβ Repertoire Kit (Beckman Coulter).

In the case of both influenza MP58 or naïve antigen MART-1, M27, large numbers of antigen specific T cells were generated. As shown in FIGS. 14 and 15, within 3-4 weekly stimulations, the absolute number of antigen specific T cells can be expanded at least several thousand fold, and large numbers of antigen specific CTLs can be produced from a limited number of lymphocytes within 1-2 months. Also, MEA1 generated CTLs are fully functional, possessing potent cytotoxicity against targets as measured by the chromium release assay (FIG. 16) and secreting the proinflammatory cytokine, γ-Interferon, as measured by ELISPOT (FIG. 17). Finally, as shown for "young" MART-1 specific CTLs in FIG. 18, these CTLs, which have an effector function, display a "central memory" phenotype.

As Table 9 shows, MEA1 has been consistently successful in generating CTL lines from a wide array of HLA-A2 restricted peptide epitopes derived from antigens such a Her-2/neu, NY-ESO-1, telomerase, MART-1, HIV. Furthermore, unlike other strategies, MEA1 stimulated T cell lines can be cultured for extended periods of time obviating the need to establish CTL clones. For example, FIG. 19 displays multimer staining and cytotoxicity of two CTL lines maintained in vitro for over one year (NY-ESO-I) or six months (Her-2/neu). Vβ subtyping demonstrates that for the NY-ESO-1 long lived cell line, all multimer staining CTLs also costain with a single Vβ subtype (Vβ 17; FIG. 20). Vβ subtyping a "younger" CTL lines demonstrates costaining of multimers with several different Vβ subtypes (data not shown). Finally, as shown in FIG. 21, despite prolonged in vitro culture, antigen specific CTLs display an "effector memory" phenotype. These cells are not terminally differentiated as shown by the lack of CD45RA expression.

TABLE 9

High Success Rate in the Generation of CTL Lines

| Antigen | Success Rate |
|---|---|
| E75 (Her-2/neu) | 2/2 |
| S9C (NY-ESO-1) | 2/3 |
| I540 (Telomerase) | 6/7 |

TABLE 9-continued

High Success Rate in the Generation of CTL Lines

| Antigen | Success Rate |
|---|---|
| M27 (MART-1) | 12/12 |
| HIV-Pol (HIV) | 3/6 |

Variations, modifications, and other implementations of what is described herein will occur to those of ordinary skill in the art without departing from the spirit and scope of the invention.

All of the references identified hereinabove, are hereby expressly incorporated herein by reference.

The invention claimed is:

1. An isolated mammalian cell comprising a recombinant nucleic acid encoding full-length CD83, a recombinant nucleic acid encoding CD80, and a recombinant nucleic acid encoding an antigen, wherein said antigen is presented on the surface of said cell in association with MHC class I, and wherein said cell functions as a professional antigen presenting cell.

2. The mammalian cell of claim 1 wherein said antigen is a tumor-specific antigen.

3. The mammalian cell of claim 1 wherein said cell is a human cell.

4. The mammalian cell of claim 1 wherein said cell is selected from the group consisting of a dendritic cell, a macrophage, a B cell, a mast cell, a parenchymal cell, a kupffer cell, or a fibroblast cell.

5. The mammalian cell of claim 1 wherein said cell is an immortalized cell.

6. The mammalian cell of claim 1 wherein said antigen is expressed as a fusion polypeptide with a heterologous reporter polypeptide.

7. The mammalian cell of claim 6 wherein said antigen is fused in frame at its N-terminus to said heterologous reporter polypeptide.

8. The mammalian cell of claim 6 wherein said antigen is located at the C terminus of said fusion polypeptide.

9. The mammalian cell of claim 6 wherein said heterologous reporter polypeptide comprises a selectable marker that permits the selection and purification of cells comprising said nucleic acid encoding an antigen.

10. The mammalian cell of claim 6 wherein said heterologous reporter polypeptide comprises a Green Fluorescent Protein.

11. The mammalian cell of claim 6 wherein said antigen expressed as a fusion polypeptide with a heterologous polypeptide is 8 to 10 amino acids in length.

12. The mammalian cell of claim 6 wherein said heterologous reporter polypeptide comprises a portion of a cell surface protein that is expressed on the surface of a cell.

13. The mammalian cell of claim 12 wherein said cell surface protein that is expressed on the surface of a cell permits the selection of cells expressing said reporter polypeptide by binding to an antibody specific for said cell surface protein.

14. The mammalian cell of claim 12 wherein said heterologous reporter polypeptide comprises a polypeptide which permits said cell to survive in selective medium.

15. The mammalian cell of claim 6 wherein said antigen is fused to said heterologous reporter polypeptide through a linker polypeptide.

16. The mammalian cell of claim 15 wherein said linker encodes said protease.

17. The mammalian cell of claim 15 wherein said linker is cleavable by a cell-associated protease.

18. The mammalian cell of claim 17 wherein said cell-associated protease is an endogenous protease.

19. The mammalian cell of claim 17 wherein said cell-associated protease is an exogenous protease expressed by an exogenous nucleic acid encoding said protease.

20. An isolated vertebrate cell comprising a recombinant nucleic acid encoding full-length CD83, a recombinant nucleic acid encoding CD80, and a recombinant nucleic acid encoding an antigen, wherein said antigen is presented on the surface of said cell in association with MHC class I, and wherein said cell functions as a professional antigen presenting cell, said vertebrate cell further comprising a recombinant nucleic acid encoding an MHC class I molecule.

21. The vertebrate cell of claim 20 wherein said class I molecule is an HLA molecule.

22. The vertebrate cell of claim 20 wherein said class I molecule is an H-2 molecule.

23. An isolated vertebrate cell comprising an exogenous antigen, a recombinant nucleic acid encoding an MHC class I molecule, a recombinant nucleic acid encoding full-length CD83, and a recombinant nucleic acid encoding CD80, wherein said antigen is presented on the surface of said cell in association with MHC class I, and wherein said cell functions as a professional antigen presenting cell.

24. The vertebrate cell of claim 23, wherein said class I molecule is an HLA molecule.

25. The vertebrate cell of claim 23, wherein said class I molecule is an H-2 molecule.

26. The vertebrate cell of claim 23, wherein said antigen is a tumor-specific antigen.

27. The vertebrate cell of claim 23, wherein said cell is a human cell.

28. The vertebrate cell of claim 23, wherein said cell is selected from the group consisting of a dendritic cell, a macrophage, a B cell, a mast cell, a parenchymal cell, a kupffer cell, or a fibroblast cell.

29. The vertebrate cell of claim 23, wherein said cell is an immortalized cell.

30. A method of making an artificial antigen presenting cell, said method comprising:
   a) contacting a population of isolated vertebrate cells with a recombinant nucleic acid encoding an MHC class I molecule, a recombinant nucleic acid encoding an full-length CD83, and a recombinant nucleic acid encoding CD80;
   b) contacting said population of vertebrate cells with an exogenous antigen; and
   c) selecting a cell that comprises said recombinant nucleic acid encoding said MHC class I molecule, said recombinant nucleic acid encoding full-length CD83, and said recombinant nucleic acid encoding CD80, and which presents said antigen at the cell surface bound to said MHC class I molecule, wherein said vertebrate cell functions as a professional antigen presenting cell.

31. The method of claim 30 wherein said population of vertebrate cells does not express an endogenous class I molecule that binds antigen.

32. The method of claim 30 wherein said class I molecule is an HLA molecule.

33. The method of claim 30 wherein said class I molecule is an H-2 molecule.

* * * * *